United States Patent
Speake et al.

(10) Patent No.: US 10,807,992 B2
(45) Date of Patent: Oct. 20, 2020

(54) SINGLE ENANTIOMER ANTIPARASITIC COMPOUNDS

(71) Applicant: Avista Pharma Solutions, Inc., Durham, NC (US)

(72) Inventors: Jason D. Speake, Winston-Salem, NC (US); Bakela Nare, Cary, NC (US); Joe B. Perales, Durham, NC (US); Keqiang Li, Cary, NC (US); Cisco Bee, Wake Forest, NC (US); Jeffrey A. Adams, Chapel Hill, NC (US); Kurt S. Van Horn, Durham, NC (US); Brian H. Heasley, Wake Forest, NC (US)

(73) Assignee: Avista Pharma Solutions, Inc., Durham, NC (US)

( * ) Notice: Subject to any disclaimer, the term of this patent is extended or adjusted under 35 U.S.C. 154(b) by 0 days.

(21) Appl. No.: 16/192,103

(22) Filed: Nov. 15, 2018

(65) Prior Publication Data

US 2019/0152983 A1    May 23, 2019

Related U.S. Application Data

(60) Provisional application No. 62/587,132, filed on Nov. 16, 2017.

(51) Int. Cl.
*C07D 491/107* (2006.01)
*A01N 43/90* (2006.01)

(52) U.S. Cl.
CPC ......... *C07D 491/107* (2013.01); *A01N 43/90* (2013.01)

(58) Field of Classification Search
CPC .................................................. C07D 491/107
See application file for complete search history.

(56) References Cited

U.S. PATENT DOCUMENTS

| | | | |
|---|---|---|---|
| 2012/0232026 A1 | 9/2012 | Curtis et al. | |
| 2014/0206633 A1 | 7/2014 | Mulholland et al. | |
| 2014/0378415 A1 | 12/2014 | Cassayre et al. | |
| 2015/0183795 A1 | 7/2015 | Billen et al. | |

FOREIGN PATENT DOCUMENTS

| | | |
|---|---|---|
| WO | 2007075459 A2 | 7/2007 |
| WO | 2007105814 A1 | 9/2007 |
| WO | 2008096746 A1 | 8/2008 |
| WO | 2008122375 A2 | 10/2008 |
| WO | 2009035004 A1 | 3/2009 |
| WO | 2009063910 A1 | 5/2009 |
| WO | 2009112275 A1 | 9/2009 |
| WO | 2010025998 A1 | 3/2010 |
| WO | 2010032437 A1 | 3/2010 |
| WO | 2010084067 A2 | 7/2010 |
| WO | 2011104089 A1 | 9/2011 |
| WO | 2012017359 A1 | 2/2012 |
| WO | 2012120399 A1 | 9/2012 |
| WO | 2014001120 A1 | 1/2014 |
| WO | 2014001121 A1 | 1/2014 |
| WO | 2014039489 A1 | 3/2014 |
| WO | 2014079935 A1 | 5/2014 |
| WO | 2014079941 A1 | 5/2014 |
| WO | 2014206911 A1 | 12/2014 |
| WO | 2016115315 A1 | 7/2016 |
| WO | 2017153218 A1 | 9/2017 |
| WO | 2017176948 A1 | 10/2017 |
| WO | 2017201134 A1 | 11/2017 |

OTHER PUBLICATIONS

International Search Report for PCT/US2018/061279, dated Mar. 14, 2019.

*Primary Examiner* — Susanna Moore
(74) *Attorney, Agent, or Firm* — Barnes & Thornburg LLP

(57) ABSTRACT

The present invention relates to single enantiomer isothiazoline compounds of formula (I):

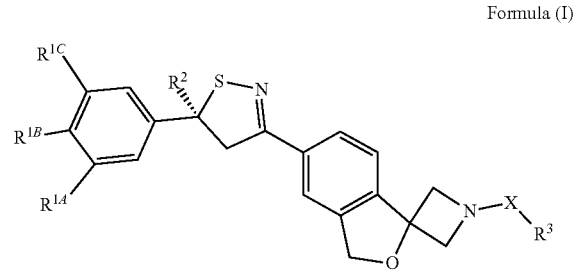

Formula (I)

and methods of synthesizing the compounds. The compounds are useful for combating or controlling invertebrate pests, in particular arthropod pests and nematodes. The invention also relates to a method for controlling invertebrate pests by using these compounds and to veterinary compositions comprising said compounds.

33 Claims, 24 Drawing Sheets

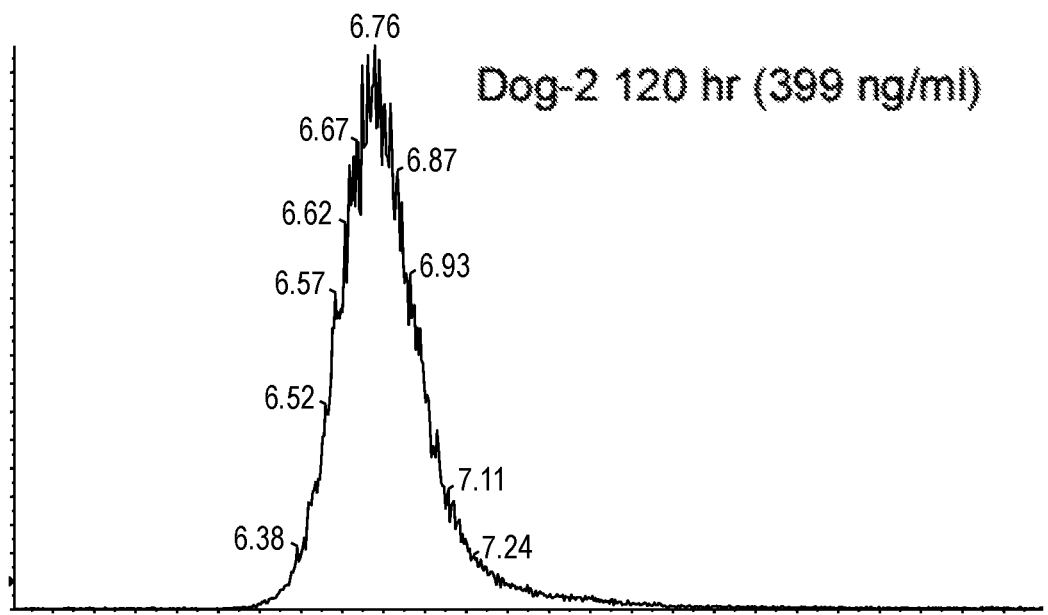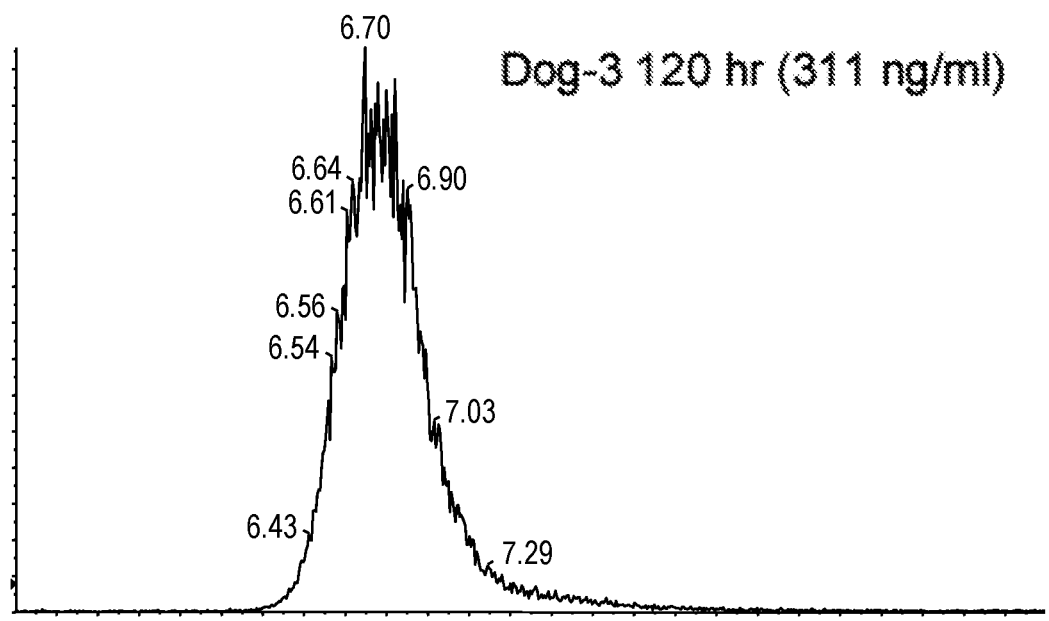
Figure 6

Figure 8
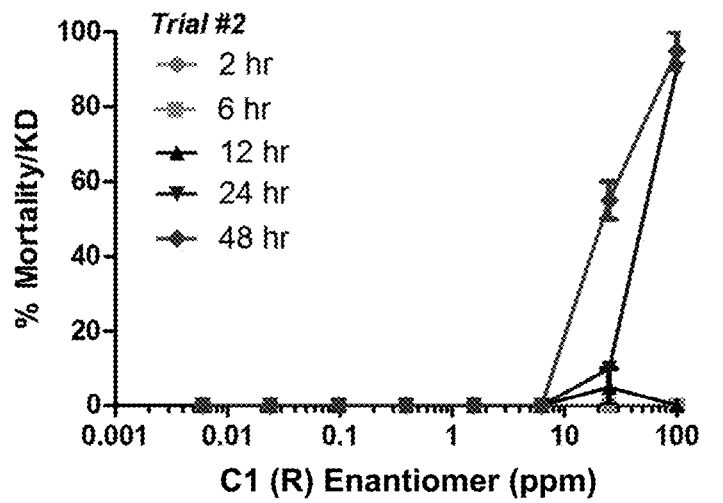
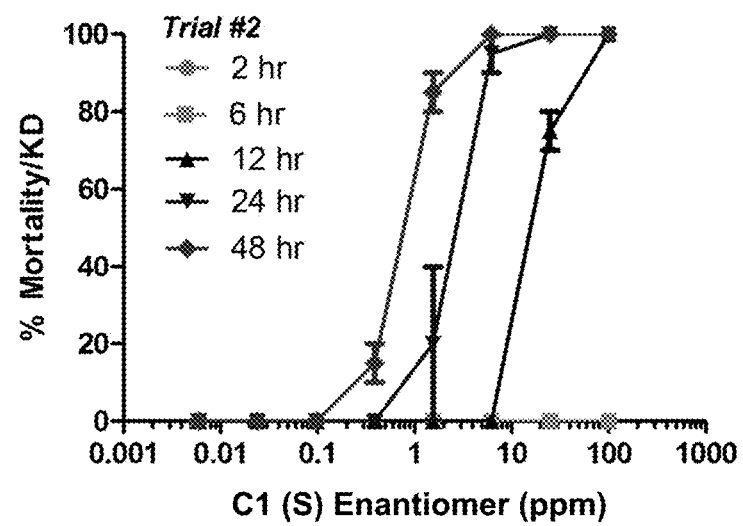
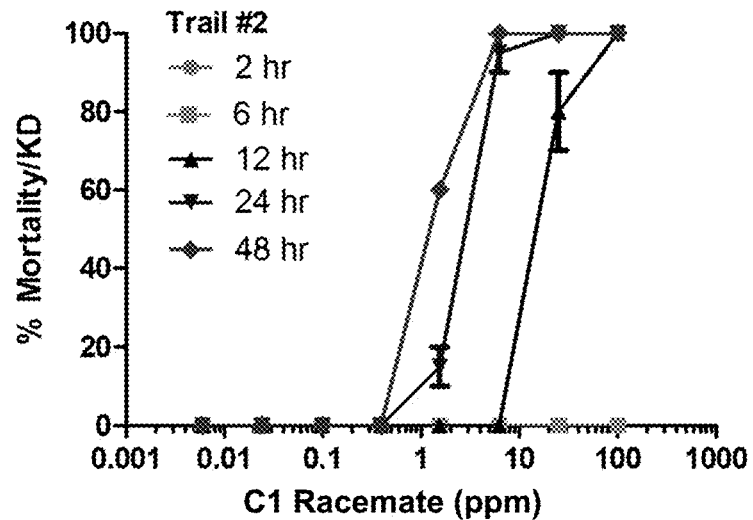

Figure 9
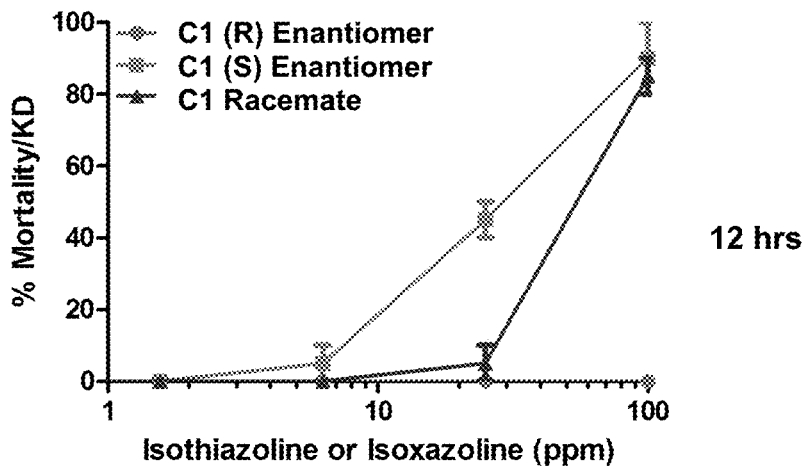
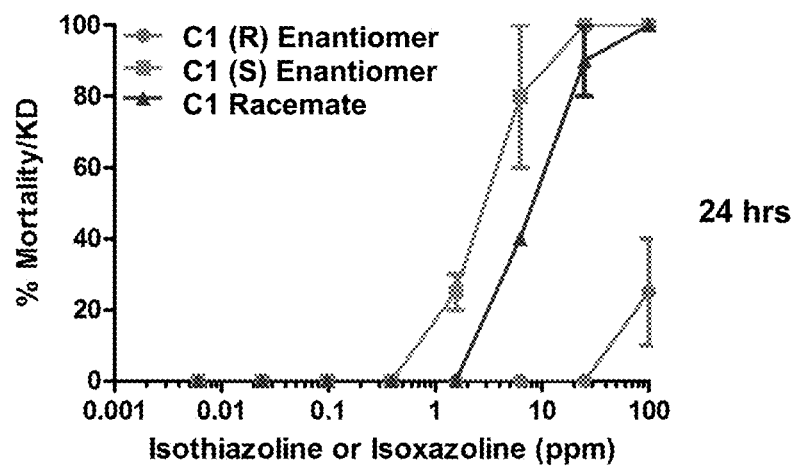
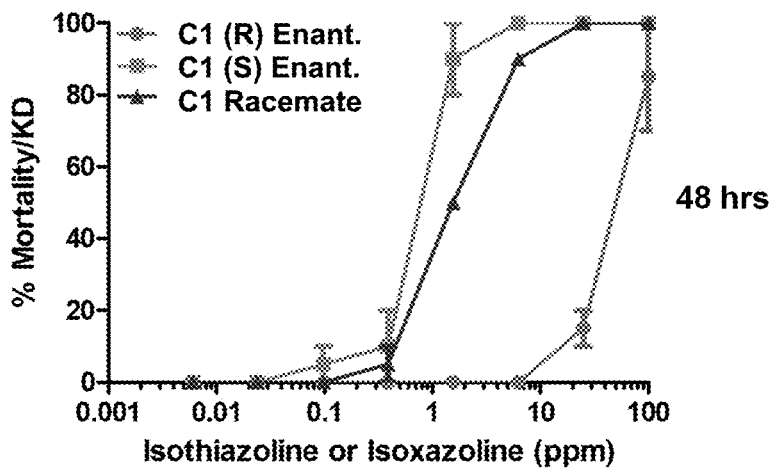

Figure 11
**Trial #1 Activity Against *D. variabilis* Contact**
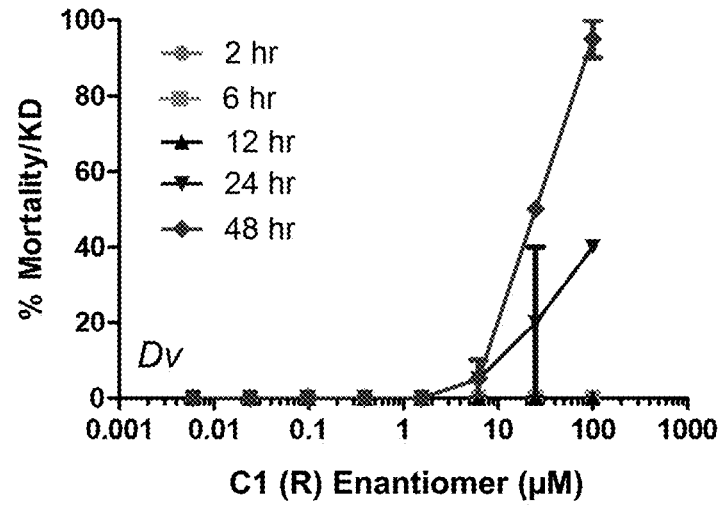
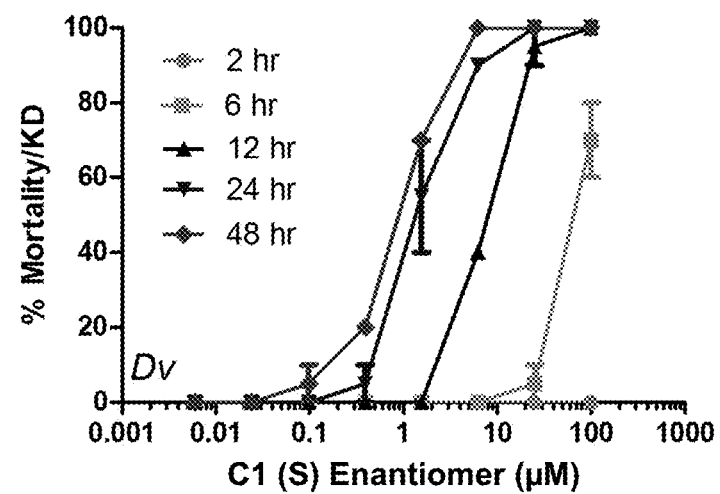
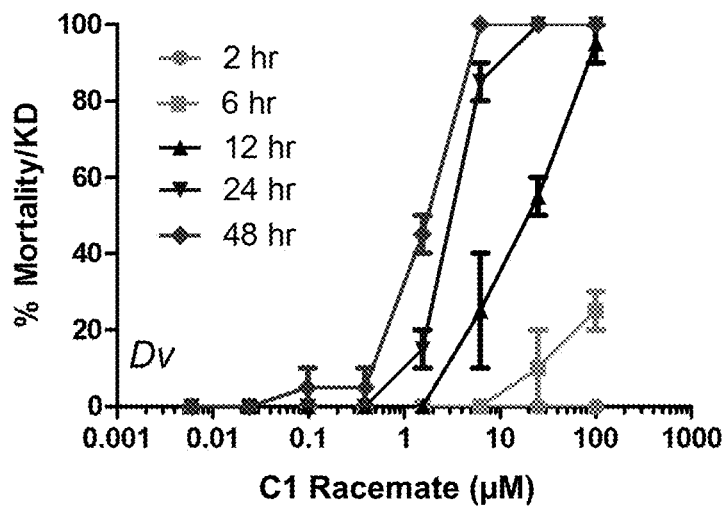

Figure 12
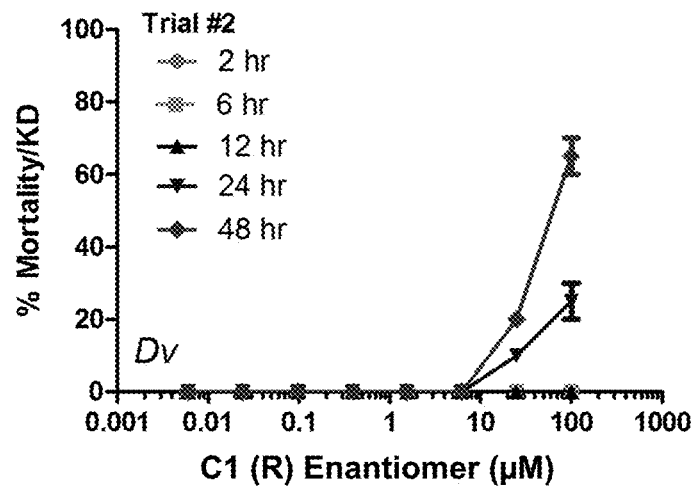
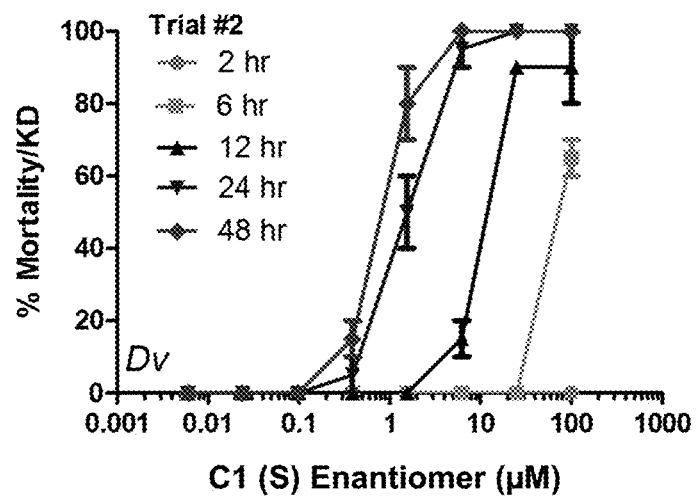
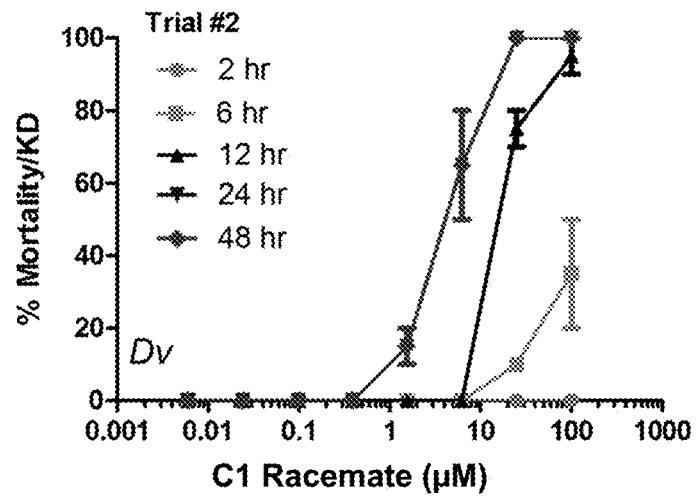

Figure 15
Trial #1 Activity Against *A. americanum* Contact
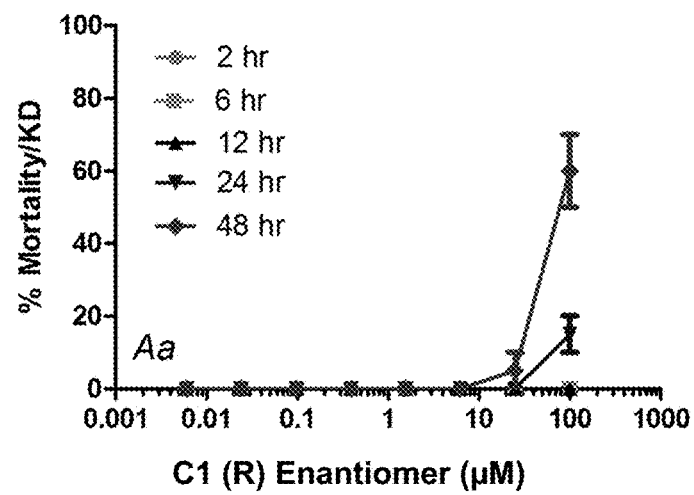
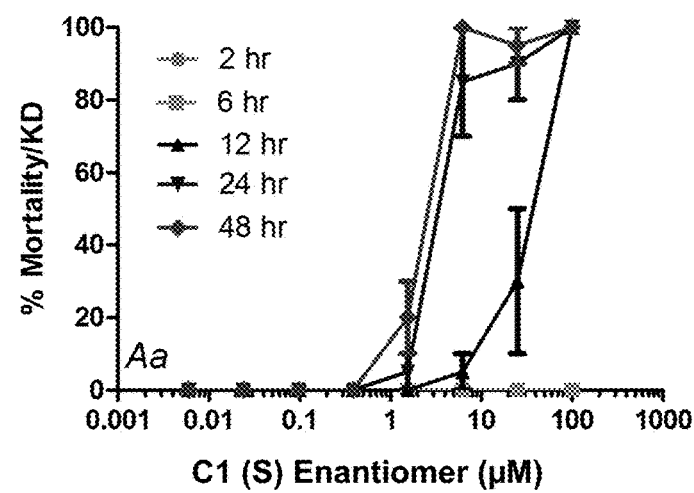
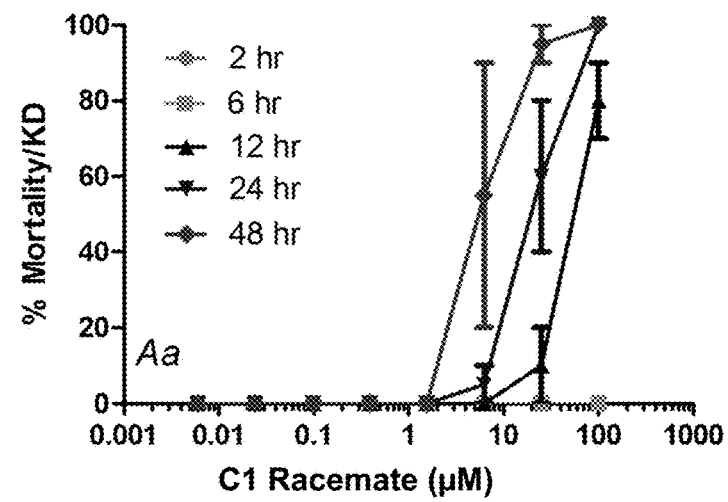

Figure 16
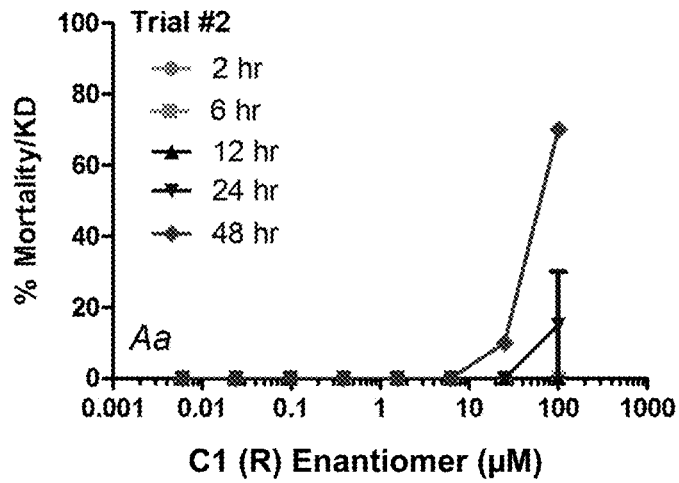
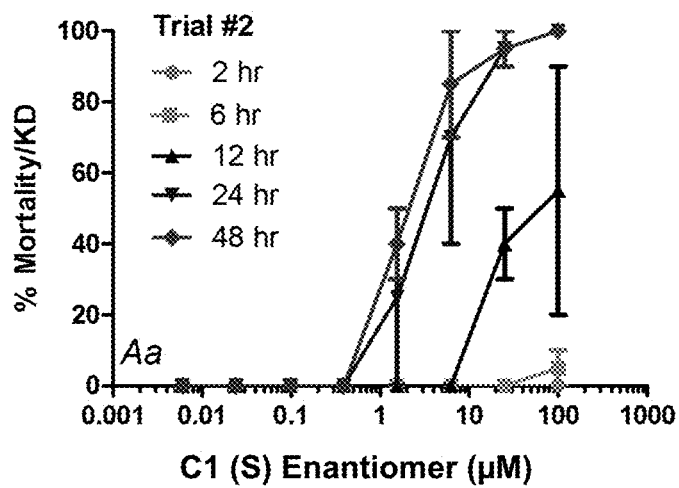
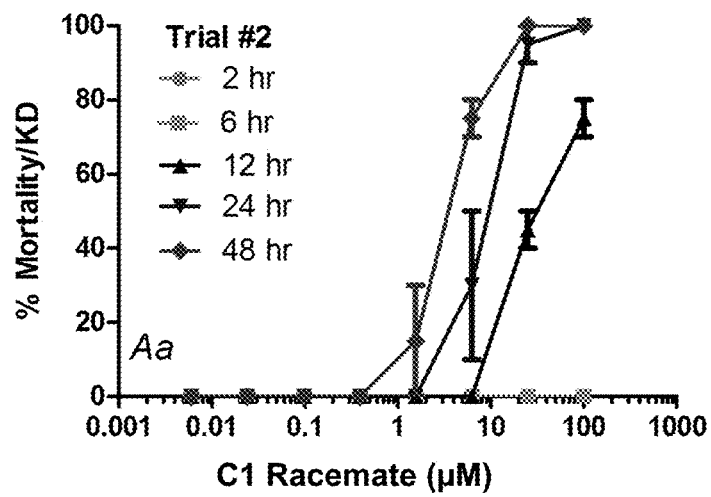

Figure 17
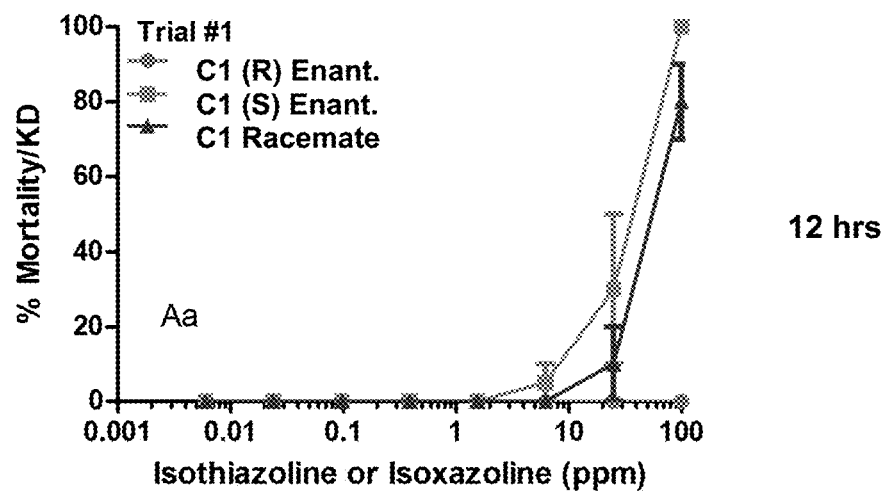
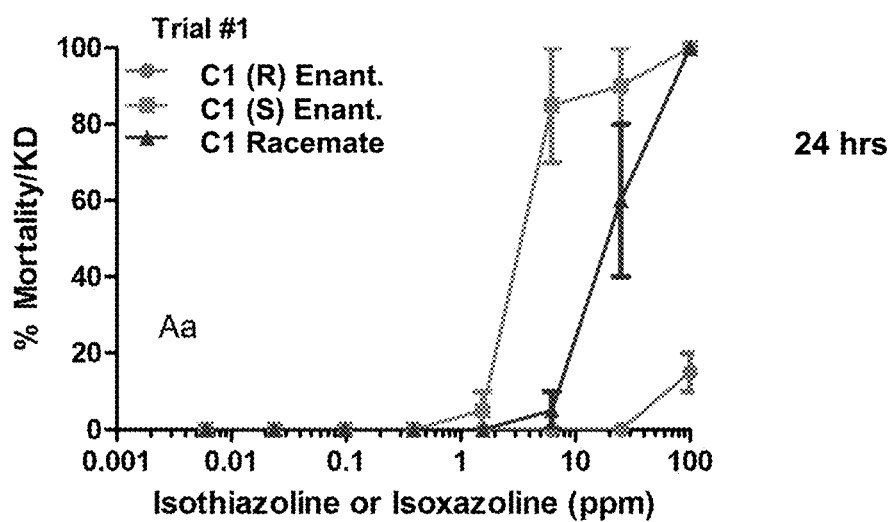
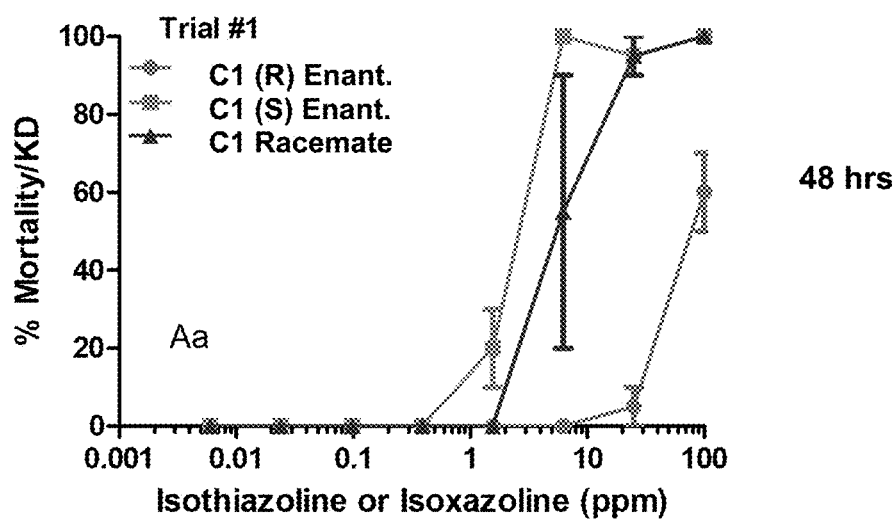

Figure 18
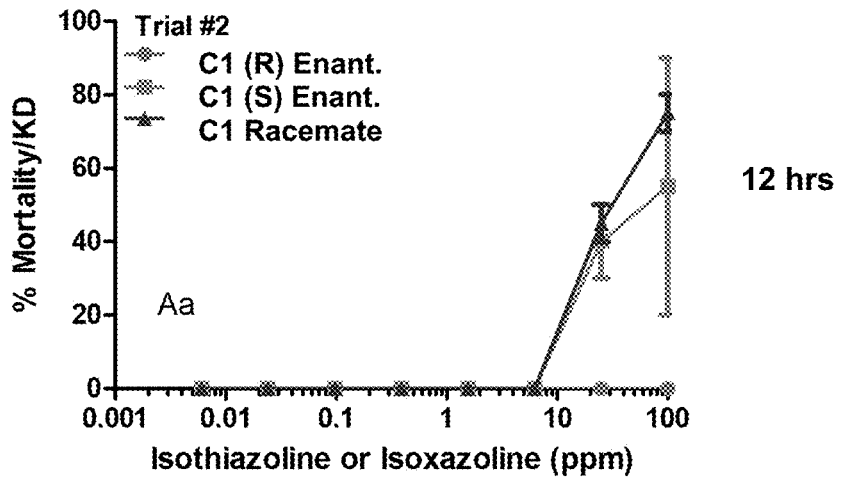
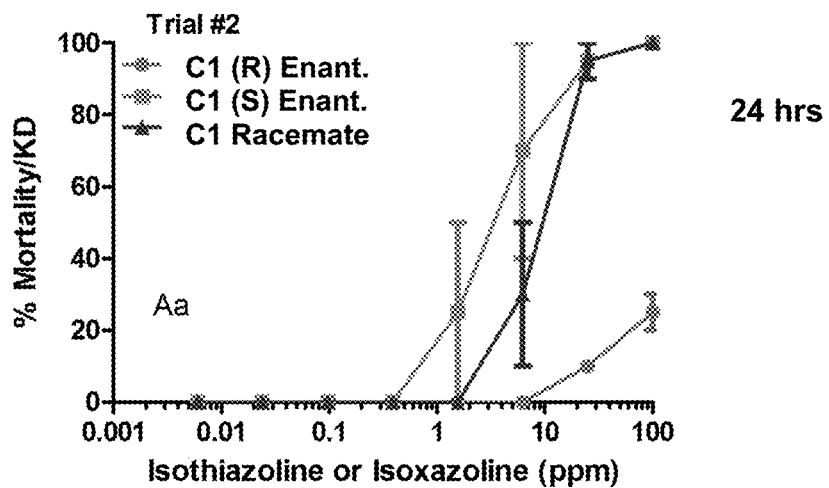
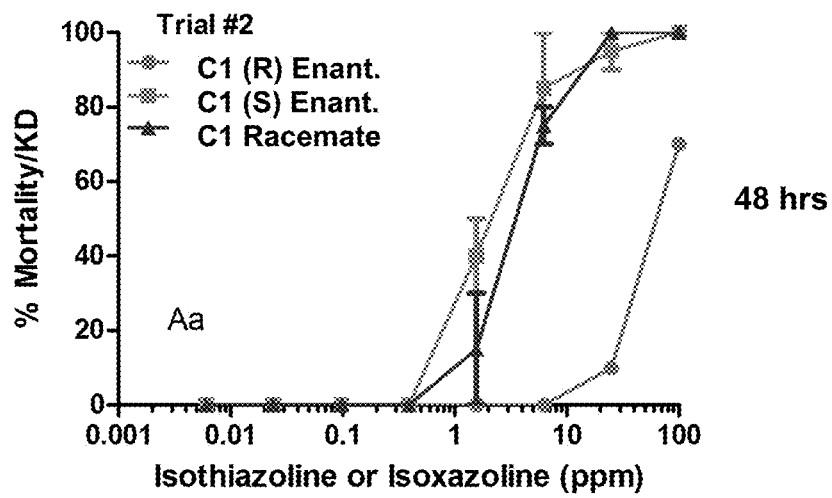

Figure 20
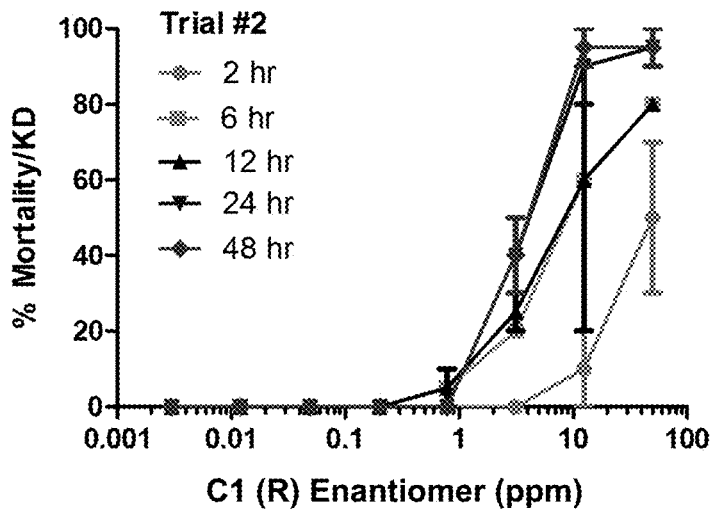
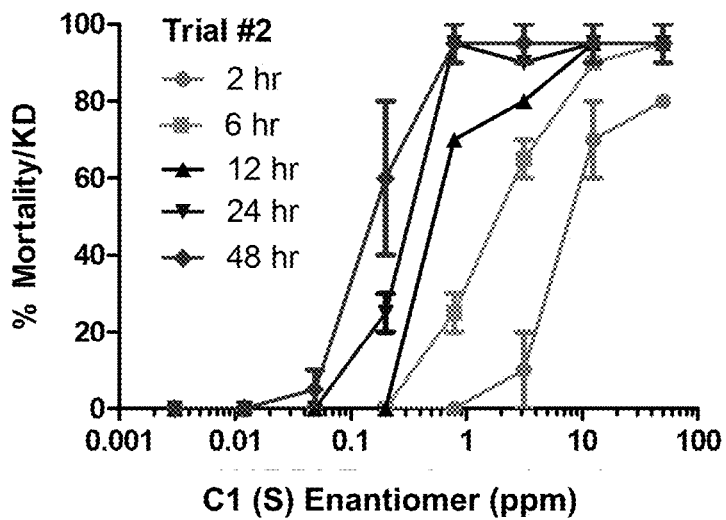
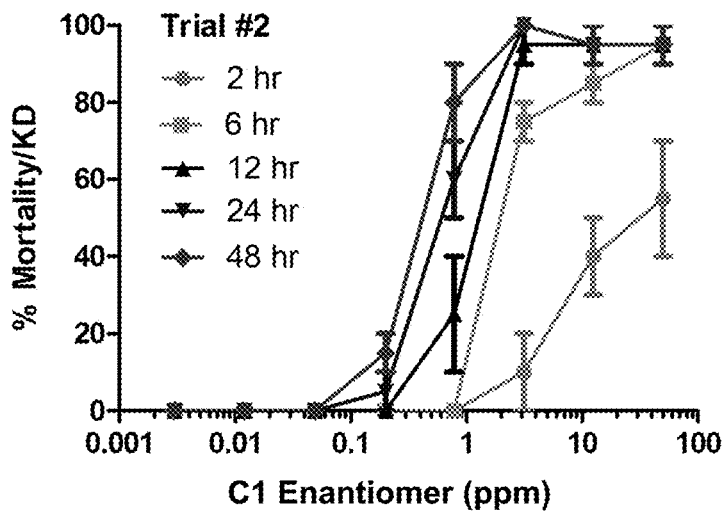

Figure 21
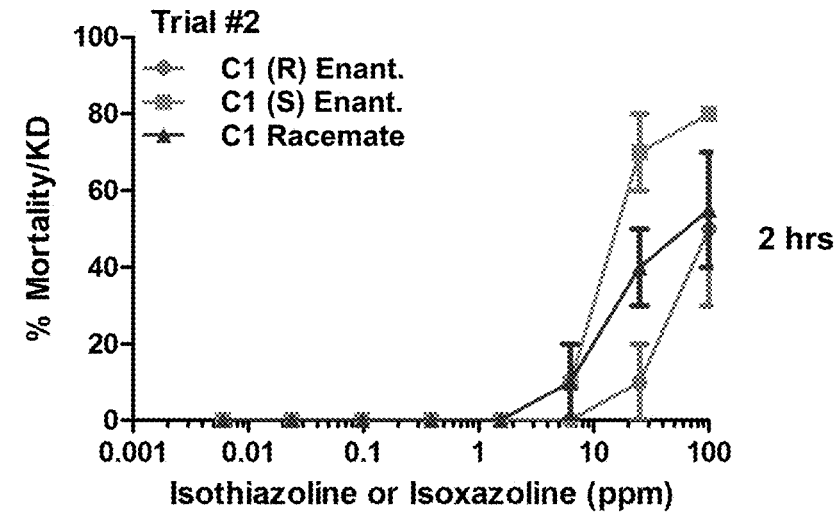
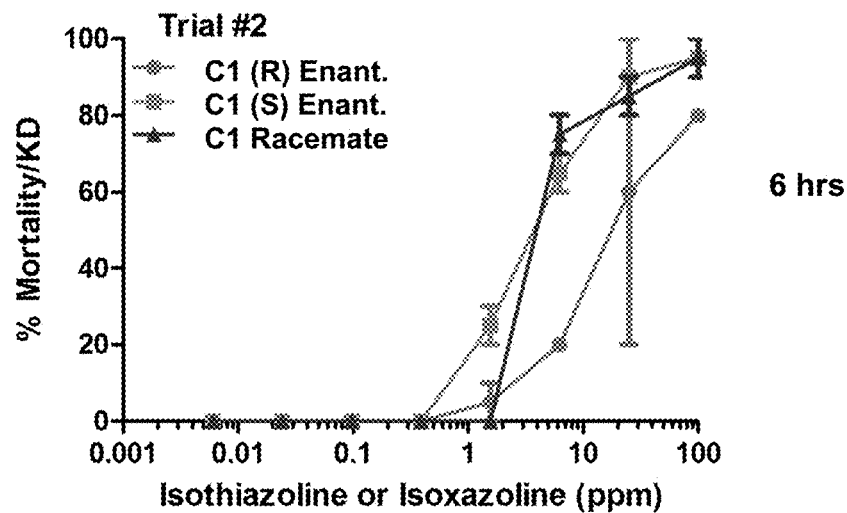
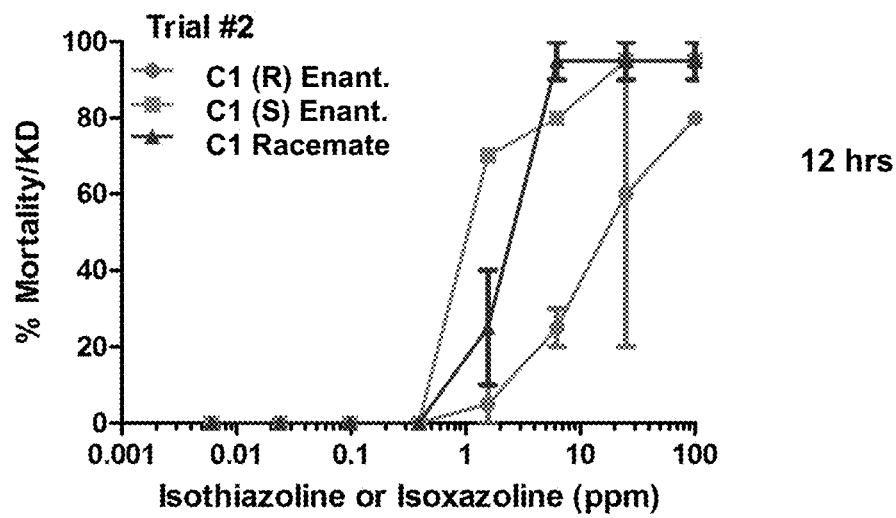

Figure 24
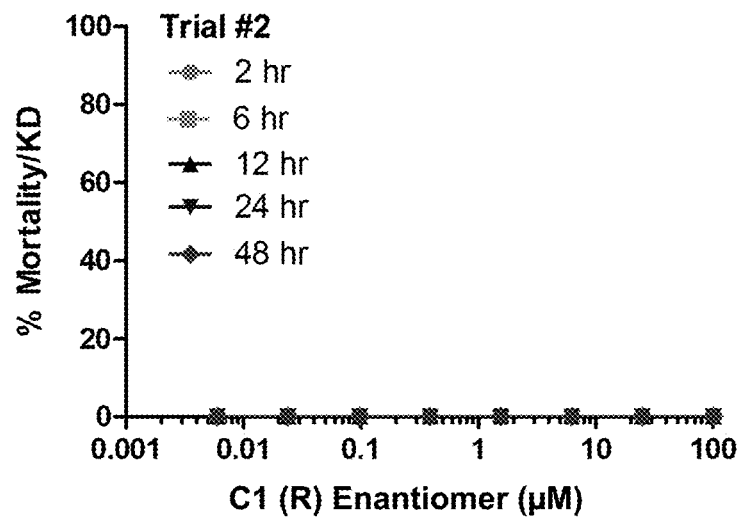
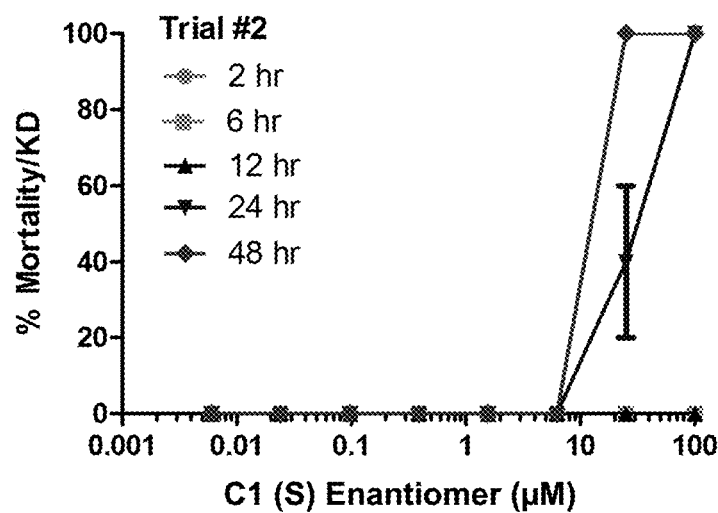
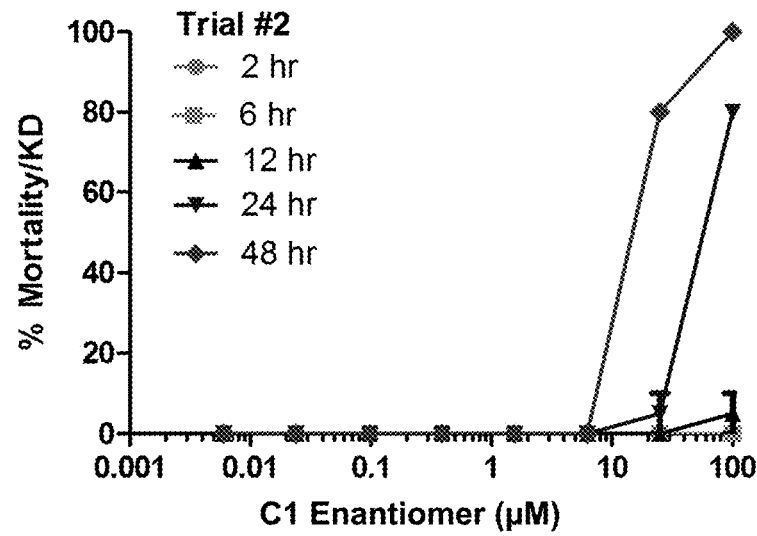

SINGLE ENANTIOMER ANTIPARASITIC COMPOUNDS

CROSS-REFERENCE TO RELATED APPLICATIONS

The present application claims priority to U.S. Provisional Application No. 62/587,132, filed Nov. 16, 2017, which is incorporated herein in its entirety.

FIELD OF THE INVENTION

The present invention includes spirocyclic derivatives having parasiticidal activity. In particular described herein are single enantiomer spirocyclic derivatives. The present invention preferably includes spirocyclic azetidenyl-isobenzofuran derivatives having an isothiazoline moiety. The present invention also includes processes of making the single enantiomer spirocyclic derivatives, compositions comprising the spirocyclic derivatives, and methods of use thereof.

BACKGROUND

There is a need for improved antiparasitics, and in particular there is a need for improved insecticides and acaricides, particularly for use in animal health. Furthermore, there is a need for improved topical and oral products with convenient administration. Still further, there is a need for improved compositions which contains one or more active antiparasitics, which can be used to effectively treat against parasites. Such improvements would be particularly useful for the treatment of animals including: birds (e.g., chickens and turkeys), fish, companion animals (e.g., cats, dogs, llamas, and horses), and livestock (e.g., cattle, bison, swine, sheep, deer, elk, and goats).

Currently available insecticidal and acaricidal treatments for animals do not always demonstrate good activity, good speed of action, or a long duration of action. Most treatments contain hazardous chemicals that can have serious consequences, including neurotoxicity and lethality from accidental ingestion. Persons applying these agents are generally advised to limit their exposure. Pet collars and tags have been utilized to overcome some problems, but these are susceptible to chewing, ingestion, and subsequent toxicological effects to the animal. Thus, current treatments achieve varying degrees of success, which depend partly on toxicity, method of administration, and efficacy. Additionally, some currently available agents are becoming ineffective due to parasitic resistance.

Despite the availability of effective, broad spectrum antiparasitics, there remains a need for safer and more convenient, efficacious, and environmentally friendly products that will overcome the ever-present threat of resistance development. The present invention includes a new enantiomer of isothiazoline spiroazetidinyl-isobenzofuran derivatives, which demonstrate such properties.

SUMMARY

The present invention includes single (S) enantiomer compounds according to Formula (I), including pesticidal, veterinary, or pharmaceutically acceptable salts thereof:

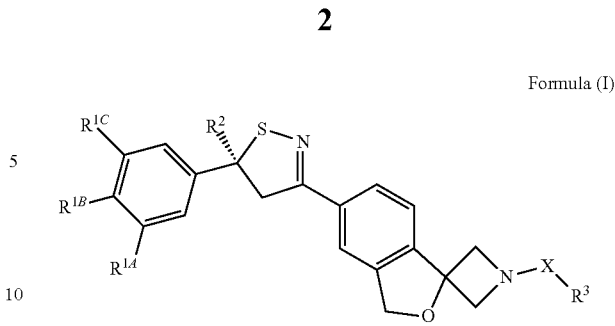

Formula (I)

wherein
each $R^{1A}$, $R^{1B}$, and $R^{1C}$ individually is hydrogen, alkyl, halogen, or haloalkyl;
$R^2$ is haloalkyl;
X is bond, C(O), $SO_2$, or C(O)NH;
$R^3$ is hydrogen, optionally substituted alkyl, optionally substituted haloalkyl, optionally substituted cycloalkyl, optionally substituted heterocyclyl, optionally substituted aryl, and optionally substituted heteroaryl,
or a pesticidal, veterinary, or pharmaceutically acceptable salt thereof, wherein the compound is stereochemically pure.
In one embodiment, the invention includes compounds of Formula (I) wherein:
each $R^{1A}$, $R^{1B}$, and $R^{1C}$ individually is halogen, haloalkyl, or alkyl;
$R^2$ is haloalkyl;
X is a bond, C(O), $SO_2$, or C(O)NH; and
$R^3$ is alkyl, haloalkyl, or aryl.
In one embodiment, the invention includes compounds of Formula (I) wherein:
each $R^{1A}$, $R^{1B}$, and $R^{1C}$ individually is halogen;
$R^2$ is perfluoroalkyl;
X is —C(O)—, —$SO_2$—, or —C(O)NH—; and
$R^3$ is haloalkyl.
In one embodiment, the invention includes compounds of Formula (I) wherein:
each $R^{1A}$ and $R^{1C}$ is a halogen and $R^{1B}$ is a different halogen;
$R^2$ is haloalkyl, preferably —$CF_3$;
X is —C(O)—; and
$R^3$ is haloalkyl, preferably —$CH_2CF_3$.
In one embodiment, the invention includes compounds of Formula (I) wherein:
each $R^{1A}$ and $R^{1C}$ is —Cl and $R^{1B}$ is —F;
$R^2$ is —$CF_3$;
X is —C(O)—; and
$R^3$ is haloalkyl, preferably —$CH_2CF_3$.
In one embodiment, the invention includes compounds of Formula (I) wherein:
each $R^{1A}$ and $R^{1C}$ is —Cl and $R^{1B}$ is —F;
$R^2$ is —$CF_3$;
X is a bond, C(O), $SO_2$, or C(O)NH; and
$R^3$ is hydrogen, optionally substituted alkyl, optionally substituted haloalkyl, optionally substituted cycloalkyl, optionally substituted heterocyclyl, optionally substituted aryl, and optionally substituted heteroaryl.
In one or more embodiments, $R^3$ is alkyl; alkyl substituted with one or more alkoxy, alkylsulfonyl, cyano, or aryl; haloalkyl; cycloalkyl; cycloalkyl substituted with one or more alkyl, alkenyl, haloalkyl, haloalkenyl, alkoxy, or carbonyl; heterocyclyl; aryl; aryl substituted with one or more halogen; or heteroaryl.

One embodiment of the invention includes compositions comprising a compound of formula (I) along with a pesticidally acceptable carrier. The compositions of the invention can also be in a variety of forms which include, but are not limited to, oral formulations, injectable formulations, and topical, dermal, or subdermal formulations. The formulations are intended to be administered to an animal, which includes, but is not limited to, mammals, birds, and fish. Examples of mammals include, but are not limited to, humans, cattle, sheep, goats, llamas, alpacas, pigs, horses, donkeys, dogs, cats, and other livestock or domestic mammals. Examples of birds include turkeys, chickens, ostriches, and other livestock or domestic birds.

The present invention includes compositions comprising a compound of formula (I) suitable for treatment of a locus that may be infected with parasites, such as a plant or animal such as a mammal, or for the prevention of infection or infestation of a locus with parasites.

Another embodiment of the present invention includes combination therapy, whereby one or more compounds of formula (I) can be employed as such or in the form of their preparations or formulations as combinations with one or more other pesticidally active substances, such as, for example, insecticides, attractants, sterilants, nematicides, acaricides, fungicides, herbicides, and with safeners, fertilizers, or growth regulators. The combinations may be part of the same formulation, or may be administered separately or sequentially to the locus.

Another embodiment of the present invention includes a compound of formula (I), or a composition comprising a compound of formula (I), for use in treating or preventing parasitic infection or infestation.

Another embodiment of the present invention includes the use of a compound of formula (I) for the manufacture of a medicament for use in treating or preventing parasitic infection or infestation.

Another embodiment of the present invention includes a method of treating or preventing a parasitic infection comprising the administration of an effective amount of a compound of formula (I), or a composition comprising a compound of formula (I) to a locus.

One embodiment of the present invention is a compound of the present invention selected from:

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one;

(S)-6-[5-(3,5-dichloro-4-fluoro-phenyl)-5-(trifluoromethyl)-4H-isothiazol-3-yl]-N-(2,2,2-trifluoroethyl)spiro[1H-isobenzofuran-3,3'-azetidine]-1'-carboxamide;

(S)-6-[5-(3,5-dichloro-4-fluoro-phenyl)-5-(trifluoromethyl)-4H-isothiazol-3-yl]-1'-(4-fluorophenyl)sulfonyl-spiro[1H-isobenzofuran-3,3'-azetidine];

(S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-phenyl-methanone;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methylsulfonyl-ethanone;

(S)-6-[5-(3,5-dichloro-4-fluoro-phenyl)-5-(trifluoromethyl)-4H-isothiazol-3-yl]spiro[1H-isobenzofuran-3,3'-azetidine];

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3-dimethyl-butan-1-one;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]butan-1-one;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-phenyl-ethanone;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-4,4,4-trifluoro-butan-1-one;

(S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-(1-naphthyl)methanone;

(S)-[(3Z,4Z)-4-allylidene-3-ethylidene-cyclohexa-1,5-dien-1-yl]-[6-[5-(3,5-dichloro-4-fluoro-phenyl)-5-(trifluoromethyl)-4H-isothiazol-3-yl]spiro[1H-isobenzofuran-3,3'-azetidine]-1'-yl]methanone;

(S)-[6-[5-(3,5-dichloro-4-fluoro-phenyl)-5-(trifluoromethyl)-4H-isothiazol-3-yl]spiro[1 H-isobenzofuran-3,3'-azetidine]-1'-yl]-(4-morpholinophenyl)methanone;

(S)-6-[5-(3,5-dichloro-4-fluoro-phenyl)-5-(trifluoromethyl)-4H-isothiazol-3-yl]-1'-propylsulfonyl-spiro[1H-isobenzofuran-3,3'-azetidine];

(S)-6-[5-(3,5-dichloro-4-fluoro-phenyl)-5-(trifluoromethyl)-4H-isothiazol-3-yl]-1'-(3,3,3-trifluoropropylsulfonyl)spiro[1H-isobenzofuran-3,3'-azetidine];

(S)-6-[5-(3,5-dichloro-4-fluoro-phenyl)-5-(trifluoromethyl)-4H-isothiazol-3-yl]-N-ethyl-spiro[1H-isobenzofuran-3,3'-azetidine]-1'-carboxamide;

(S)-6-[5-(3,5-dichloro-4-fluoro-phenyl)-5-(trifluoromethyl)-4H-isothiazol-3-yl]-N-phenyl-spiro[1H-isobenzofuran-3,3'-azetidine]-1'-carboxamide;

(S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-[3-(2,2-dichlorovinyl)-2,2-dimethyl-cyclopropyl]methanone;

(S)-[6-[5-(3,5-dichloro-4-fluoro-phenyl)-5-(trifluoromethyl)-4H-isothiazol-3-yl]spiro[1H-isobenzofuran-3,3-azetidine]-1'yl]-tetrahydropyran-4-yl-methanone;

(S)-1'-butyl-6-[5-(3,5-dichloro-4-fluoro-phenyl)-5-(trifluoromethyl)-4H-isothiazol-3-yl]spiro[1H-isobenzofuran-3,3'-azetidine];

(S)-6-[5-(3,5-dichloro-4-fluoro-phenyl)-5-(trifluoromethyl)-4H-isothiazol-3-yl]-1'-(3,3-dimethylbutyl)spiro[1H-isobenzofuran-3,3'-azetidine];

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methoxy-ethanone;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-isopropoxy-ethanone;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-ethoxy-ethanone;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methyl-propan-1-one;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]propan-1-one;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]ethanone;

(S)-3-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-4-ethoxy-cyclobut-3-ene-1,2-dione;

(S)-3-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3-oxo-propanenitrile;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2,2,3,3,3-pentafluoro-propan-1-one;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2,2-difluoro-propan-1-one;

(S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-[1-(trifluoromethyl)cyclopropyl]methanone;

(S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-[1-(trifluoromethyl)cyclobutyl]methanone;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-2,2-dimethyl-propan-1-one;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]pentan-1-one;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]hexan-1-one;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]heptan-1-one;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]octan-1-one;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]nonan-1-one;

(S)-6-[5-(3,5-dichloro-4-fluoro-phenyl)-5-(trifluoromethyl)-4H-isothiazol-3-yl]-1'-pyrimidin-2-yl-spiro[1H-isobenzofuran-3,3'-azetidine]; and (S)-6-[5-(3,5-dichloro-4-fluoro-phenyl)-5-(trifluoromethyl)-4H-isothiazol-3-yl]-N-methyl-spiro[1H-isobenzofuran-3,3'-azetidine]-1'-carboxamide, or a pesticidal, veterinary, or pharmaceutically acceptable salt thereof, wherein the compound is stereochemically pure.

One embodiment of the present invention is a composition comprising a compound of the present invention and a pesticidally acceptable carrier. Another embodiment of the present invention is a combination comprising a compound of the present invention and one or more other pesticidally active substances. Another embodiment of the present invention is a method for controlling parasites at a locus comprising applying to the locus an effective amount of a compound of the present invention. Another embodiment of the present invention is a method of treating or preventing parasitic infection or infestation in a subject comprising administering to the subject an effective amount of a compound of the present invention. In one aspect, the parasite is a flea or tick. In one aspect, the parasite is *Ctenocephalides felis, R. sanguineus, D. variablis, A. americanum*, or *I. scapularis*. In one aspect, the parasite is a helminth. In one aspect, the parasite is *Dirofilaria immitis*. Another embodiment of the present invention is a compound of the present invention for use in treating or preventing parasitic infection or infestation. Another embodiment is a compound of the present invention for use in medicine.

One embodiment of the present invention is a compound (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one according to the following structure:

In some embodiments described herein, the (S) enantiomer compounds are a pesticidal, veterinary, or pharmaceutically acceptable salt thereof. In some embodiments, the (S) enantiomer compounds described herein are stereochemically pure.

Another embodiment is a composition comprising a single (S) enantiomer compound (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof and one or more pesticidal, veterinary, or pharmaceutically acceptable carrier, wherein the compound is stereochemically pure and the composition is substantially free of a compound (R)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3, 3-trifluoro-propan-1-one.

Another embodiment of the present invention is a combination comprising a single (S) enantiomer compound (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof and one or more other pesticidally active substances, wherein the compound is stereochemically pure and is substantially free of a compound (R)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one.

Another embodiment of the present invention is a method for controlling parasites at a locus comprising applying to the locus an effective amount of a single (S) enantiomer compound (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof, wherein the compound is stereochemically pure and is substantially free of a compound (R)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one.

Another embodiment of the present invention is a method of treating or preventing parasitic infection or infestation in a subject comprising administering to the subject an effective amount of a single (S) enantiomer compound (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof, wherein the compound is stereochemically pure and is substantially free of a compound (R)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one. In one aspect, the parasite is a flea or tick. In one aspect, the parasite is *Ctenocephalides felis, R. sanguineus, D. variablis, A. americanum*, or *I. scapularis*. In one aspect, the parasite is a helminth. In one aspect, the parasite is *Dirofilaria immitis*. Another embodiment of the present invention is (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof, wherein the compound is stereochemically pure for use in treating or preventing parasitic infection or infestation. Another embodiment is (S)-1-[6-[5-(3,5-dichloro-4-fluorophenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof, wherein the compound is stereochemically pure for use in medicine.

Another embodiment is a compound, wherein the compound is (Z)-3-(3,5-dichloro-4-fluorophenyl)-4,4,4-trifluoro-1-(1-(3,3,3-trifluoropropanoyl)-3'H-spiro[azetidine-3,1'-isobenzofuran]-5'-yl)but-2-en-1-one according to the structure:

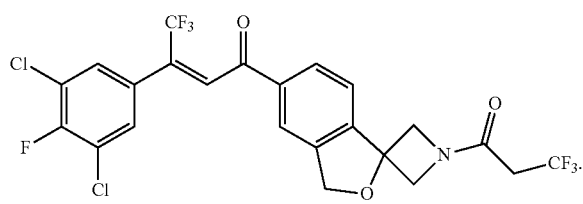 [SMILES: O=C(/C=C(/c1cc(Cl)c(F)c(Cl)c1)C(F)(F)F)c1ccc2c(c1)COC21CN(C(=O)CC(F)(F)F)C1]

Another embodiment is a method of making the (Z)-3-(3,5-dichloro-4-fluorophenyl)-4,4,4-trifluoro-1-(1-(3,3,3-trifluoropropanoyl)-3'H-spiro[azetidine-3,1'-isobenzofuran]-5'-yl)but-2-en-1-one compound comprising preparing a mixture comprising 1-(5'-acetyl-3H-spiro[azetidine-3,1'-isobenzofuran]-1-yl)-3,3,3-trifluoropropan-1-one and 1-(3,5-dichloro-4-fluorophenyl)-2,2,2-trifluoroethan-1-one and reacting the mixture to form the compound. In one aspect, the mixture further comprises an organic solvent and a base. In another aspect, the mixture is heated to a temperature of about 40° C. to about 80° C.

Another embodiment is a single (S) enantiomer compound, wherein the compound is (S)-3-(3,5-dichloro-4-fluorophenyl)-4,4,4-trifluoro-3-((4-methoxybenzyl)thio)-1-(1-(3,3,3-trifluoropropanoyl)-3'H-spiro[azetidine-3,1'-isobenzofuran]-5'-yl)butan-1-one according to the structure:

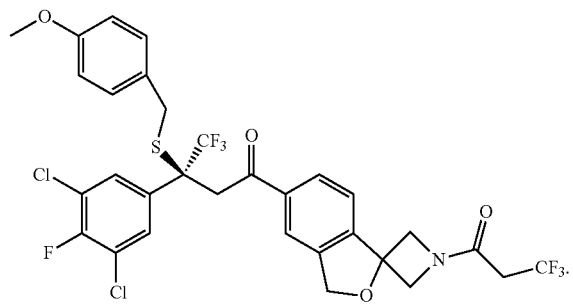 [SMILES: COc1ccc(CS[C@@](CC(=O)c2ccc3c(c2)COC32CN(C(=O)CC(F)(F)F)C2)(c2cc(Cl)c(F)c(Cl)c2)C(F)(F)F)cc1]

Another embodiment is a method of making the (S)-3-(3,5-dichloro-4-fluorophenyl)-4,4,4-trifluoro-3-((4-methoxybenzyl)thio)-1-(1-(3,3,3-trifluoropropanoyl)-3'H-spiro[azetidine-3,1'-isobenzofuran]-5'-yl)butan-1-one compound comprising preparing a mixture comprising the compound (Z)-3-(3,5-dichloro-4-fluorophenyl)-4,4,4-trifluoro-1-(1-(3,3,3-trifluoropropanoyl)-3'H-spiro[azetidine-3,1'-isobenzofuran]-5'-yl)but-2-en-1-one, an enantioselective catalyst selected from 3-((3,5-bis(trifluoromethyl)phenyl)amino)-4-(((R)-(6-methoxyquinolin-4-yl)((1S,2R,4S,5R)-5-vinylquinuclidin-2-yl)methyl)amino)cyclobut-3-ene-1,2-dione and p-methoxybenzyl mercaptan and reacting the mixture to form the compound. In one aspect, the mixture further comprises di-potassium phosphate and an organic solvent. In another aspect, the p-methoxybenzyl mercaptan is dissolved in an organic solvent and is added to the mixture over a time period of about 1 hour to about 96 hours. In another aspect, the p-methoxybenzyl mercaptan is dissolved in an organic solvent and is added to the mixture over a time period of about 20 hours to about 60 hours.

Another embodiment is a single (S) enantiomer compound, wherein the compound is (S)-3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5'-yl)butan-1-one according to the structure:

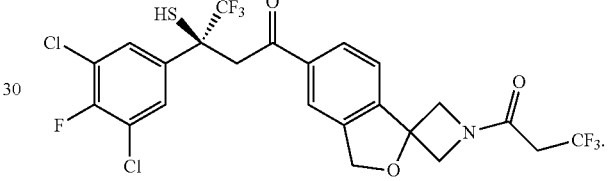

Another embodiment is a method of making the (S)-3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5'-yl)butan-1-one compound comprising preparing a mixture comprising (S)-3-(3,5-dichloro-4-fluorophenyl)-4,4,4-trifluoro-3-((4-methoxybenzyl)thio)-1-(1-(3,3,3-trifluoropropanoyl)-3'H-spiro[azetidine-3,1'-isobenzofuran]-5'-yl)butan-1-one and adding an acid and reacting the mixture to form the compound. In one aspect, the acid has a pKa of less than 1. In another aspect, the acid is selected from hydrochloric acid, trifluoroacetic acid and triflic acid.

In some embodiments described herein, the (S) enantiomer compounds described herein is about 90%, 91%, 92%, 93%, 94%, 95%, 96%, 97%, 98%, 99%, 99.5%, 99.8%, 99.9%, or 100% free of any (R) enantiomer.

Another embodiment is a method for making the (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one compound comprising (a). preparing a mixture comprising 1-(5'-acetyl-3'H-spiro[azetidine-3,1'-isobenzofuran]-1-yl)-3,3,3-trifluoropropan-1-one and 1-(3,5-dichloro-4-fluorophenyl)-2,2,2-trifluoroethan-1-one and performing a reaction comprising reacting the mixture to obtain a compound (Z)-3-(3,5-dichloro-4-fluorophenyl)-4,4,4-trifluoro-1-(1-(3,3,3-trifluoropropanoyl)-3'H-spiro[azetidine-3,1'-isobenzofuran]-5'-yl)but-2-en-1-one; (b). preparing a mixture comprising the compound of (a), an enantioselective catalyst, and a thiol donor and performing a reaction comprising reacting the mixture to form a thiol ether compound of formula (Ia):

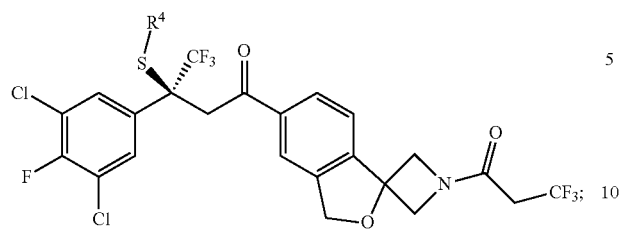

Ia wherein R⁴ is selected from hydrogen, optionally substituted C$_1$-C$_{10}$ alkyl, optionally substituted phenyl, and optionally substituted benzyl;

(c) cleaving the thiol ether of (b) to form a compound (S)-3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5'-yl)butan-1-one; and (d) preparing a mixture comprising the compound of (c) and hydroxylamine-O-sulfonic acid and performing a reaction comprising reacting the mixture to form a compound (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one. Some additional aspects for synthesizing the (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one are contemplated herein. In one aspect, the method for making the reaction of (a) further comprises adding a base to the mixture. In another aspect, the base has a pKb of about -2 to about 9. In a further aspect, the base is selected from potassium hydroxide, sodium hydroxide, calcium hydroxide, Hunig's Base, DBU, N-methylmorpholine, pyridine, 2,6-di-tert-butylpyridine, 2,6-lutidine, TMEDA, DABCO, 2,2,6,6-tetramethylpiperidine, trimethylamine, and cesium carbonate. In another aspect, the enantioselective catalyst is selected from a secondary amine, a thiourea, and a squaramide enantioselective catalyst. In another aspect, the squaramide enantioselective catalyst is 3-((3,5-bis(trifluoromethyl)phenyl)amino)-4-(((R)-(6-methoxyquinolin-4-yl)((1S,2R,4S,5R)-5-vinylquinuclidin-2-yl)methyl)amino)cyclobut-3-ene-1,2-dione according to the structure:

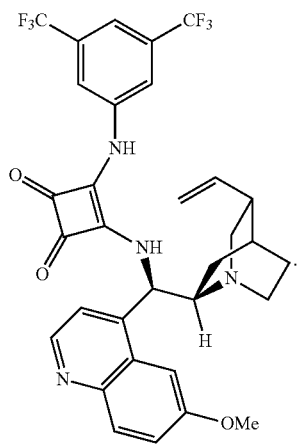 [SMILES: C=CC1CN2CCC1C[C@@H]2[C@H](Nc1c(Nc2cc(C(F)(F)F)cc(C(F)(F)F)c2)c(=O)c1=O)c1ccnc2ccc(OC)cc12]

In another aspect, the thiol donor is selected from benzyl mercaptan and 4-methoxybenzyl mercaptan. In another aspect, the thiol ether compound of formula (Ia) is (S)-3-(3,5-dichloro-4-fluorophenyl)-4,4,4-trifluoro-3-((4-methoxybenzyl)thio)-1-(1-(3,3,3-trifluoropropanoyl)-3'H-spiro[azetidine-3,1'-isobenzofuran]-5'-yl)butan-1-one according to the structure:

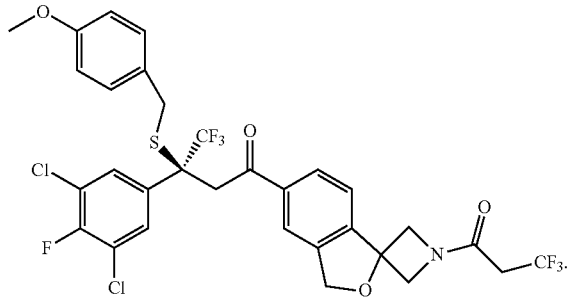 [SMILES: COc1ccc(CS[C@@](CC(=O)c2ccc3c(c2)COC32CN(C(=O)CC(F)(F)F)C2)(c2cc(Cl)c(F)c(Cl)c2)C(F)(F)F)cc1]

In another aspect, the cleaving (c) is an acid based cleavage comprising preparing a mixture comprising the thiol ether of (b) and adding an acid. In another aspect, the acid has a pKa of less than 1. In another aspect, the acid is selected from hydrochloric acid, trifluoroacetic acid and triflic acid. In another aspect, the reaction of (d) further comprises adding a base and quenching the reaction with an acid.

BRIEF DESCRIPTION OF THE DRAWINGS

FIG. 6. Representative chromatogram of C1 (S) enantiomer by chiral HPLC. By comparing 120 hr dog plasma samples for dogs 2 and 3 and a standard of similar concentration, there is no conceivable increase in the C1 (R) enantiomer content in vivo.

FIG. 8. Trial #2 activity of the C1 (R) enantiomer, C1 (S) enantiomer, and C1 racemate against *R. sanguineus* in a contact assay. Assay points assessing mortality were taken at 2, 6, 12, 24, and 48 hours at the indicated concentrations of C1 compound in parts per million (ppm).

FIG. 9. Trial #1 activity of the C1 (R) enantiomer, C1 (S) enantiomer, and C1 racemate against *R. sanguineus* in a speed of kill in contact assay. Assay points assessing mortality were taken at 12, 24, and 48 hours at the indicated concentrations of C1 compound in parts per million (ppm).

FIG. 11. Trial #1 activity of the C1 (R) enantiomer, C1 (S) enantiomer, and C1 racemate against *D. variabilis* in a contact assay. Assay points assessing mortality were taken at 2, 6, 12, 24, and 48 hours at the indicated concentrations of C1 compound in (μM).

FIG. 12. Trial #2 activity of the C1 (R) enantiomer, C1 (S) enantiomer, and C1 racemate against *D. variabilis* in a contact assay. Assay points assessing mortality were taken at 2, 6, 12, 24, and 48 hours at the indicated concentrations of C1 compound in (μM).

FIG. 15. Trial #1 activity of the C1 (R) enantiomer, C1 (S) enantiomer, and C1 racemate against *A. americanum* in a contact assay. Assay points assessing mortality were taken at 2, 6, 12, 24, and 48 hours at the indicated concentrations of C1 compound in (μM).

FIG. 16. Trial #2 activity of the C1 (R) enantiomer, C1 (S) enantiomer, and C1 racemate against *A. americanum* in a contact assay. Assay points assessing mortality were taken at 2, 6, 12, 24, and 48 hours at the indicated concentrations of C1 compound in (μM).

FIG. 17. Trial #1 activity of the C1 (R) enantiomer, C1 (S) enantiomer, and C1 racemate against *A. americanum* in a speed of kill in contact assay. Assay points assessing mortality were taken at 12, 24, and 48 hours at the indicated concentrations of C1 compound in parts per million (ppm).

FIG. 18. Trial #2 activity of the C1 (R) enantiomer, C1 (S) enantiomer, and C1 racemate against *A. americanum* in a speed of kill in contact assay. Assay points assessing mortality were taken at 12, 24, and 48 hours at the indicated concentrations of C1 compound in parts per million (ppm).

FIG. 20. Trial #2 activity of the C1 (R) enantiomer, C1 (S) enantiomer, and C1 racemate against *C. felis* in an ingestion assay. Assay points assessing mortality were taken at 2, 6, 12, 24, and 48 hours at the indicated concentrations of C1 compound in parts per million (ppm).

FIG. 21. Trial #2 activity of the C1 (R) enantiomer, C1 (S) enantiomer, and C1 racemate against *C. felis* in a speed of kill ingestion assay. Assay points assessing mortality were taken at 2, 6, and 12 hours at the indicated concentrations of C1 compound in parts per million (ppm).

FIG. 24. Trial #2 activity of the C1 (R) enantiomer, C1 (S) enantiomer, and C1 racemate against *C. felis* in a contact assay. Assay points assessing mortality were taken at 2, 6, 12, 24, and 48 hours at the indicated concentrations of C1 compound in (μM).

DETAILED DESCRIPTION

Figure 1:
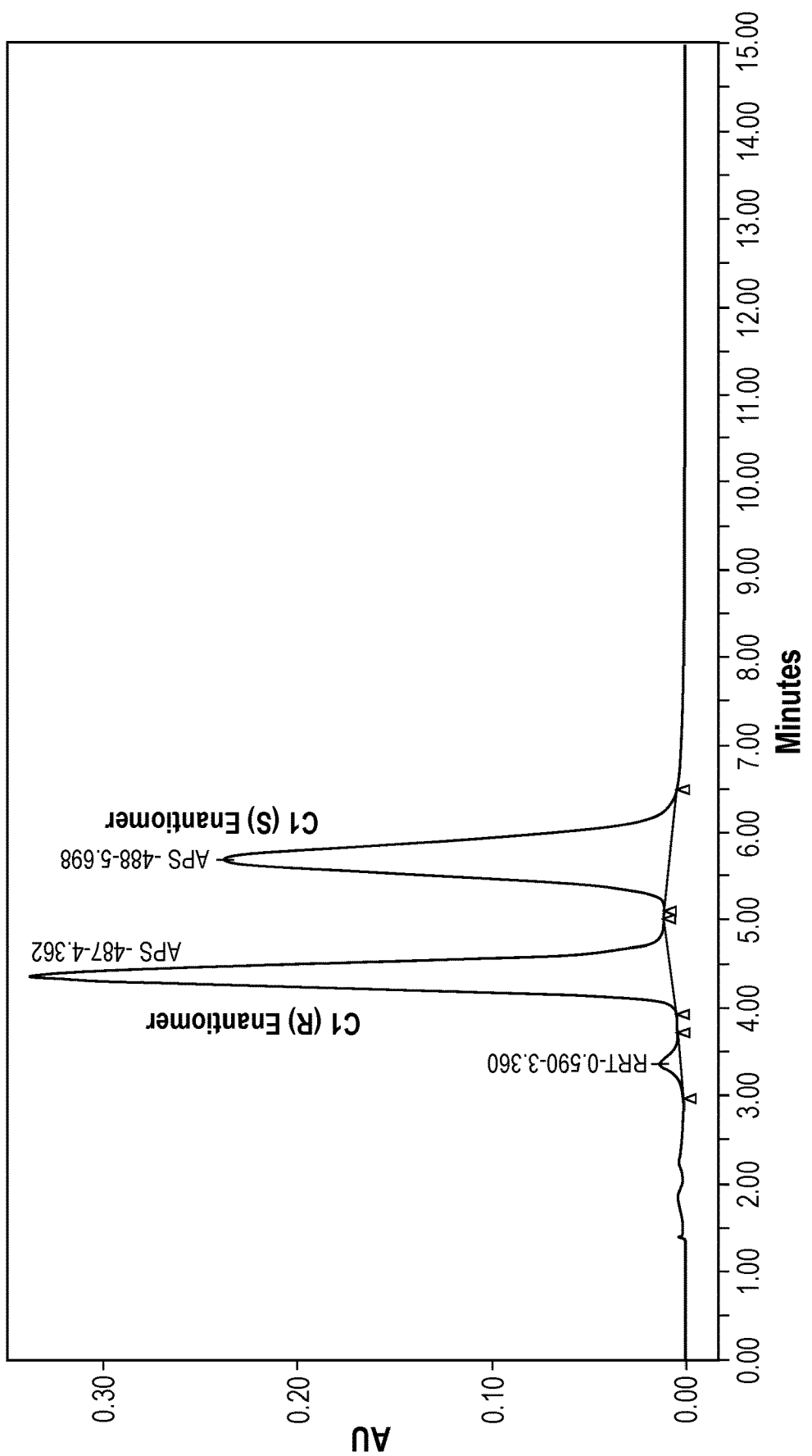
FIG. 1. Representative Chromatogram of C1 (R) enantiomer and C1 (S) enantiomer by Chiral HPLC

One or more aspects and embodiments may be incorporated in a different embodiment although not specifically described. That is, all aspects and embodiments can be combined in any way or combination.

Definitions

When referring to the compounds disclosed herein, the following terms have the following meanings unless indicated otherwise. The following definitions are meant to clarify, but not limit, the terms defined. If a particular term used herein is not specifically defined, such term should not be considered indefinite. Rather, terms are used within their accepted meanings.

As used herein, the term "alkoxy" refers to the group -OR where R is alkyl. Illustrative alkoxy groups include methoxy, ethoxy, n-propoxy, isopropoxy, n-butoxy, tert-butoxy, sec-butoxy, n-pentoxy, n-hexoxy, and 1,2-dimethylbutoxy.

As used herein, "alkyl" refers to monovalent saturated aliphatic hydrocarbyl groups having from 1 to 20 carbon atoms, preferably 1-8 carbon atoms, preferably 1-6 carbon atoms. The hydrocarbon chain can be either straight-chained or branched. Illustrative alkyl groups include methyl, ethyl, n-propyl, isopropyl, n-butyl, iso-butyl, and tert-butyl. Similarly, an "alkenyl" group refers to an alkyl group having one or more double bonds present in the chain.

As used herein, "cycloalkyl" refers to an unsaturated or partially saturated hydrocarbon ring, containing from 3 to 6 ring atoms. Illustrative cycloalkyl groups include cyclopropyl, cyclobutyl, cyclopentyl, cyclohexyl, as well as partially saturated versions thereof, such as cyclohexenyl, and cyclohexadienyl.

As used herein "halogen" or "halo" refers to a halogen. In some embodiments, the halogen is preferably Br, Cl, or F. As used herein, "haloalkyl" refers to monovalent saturated aliphatic hydrocarbyl groups having from 1 to 20 carbon atoms, preferably 1-8 carbon atoms, preferably 1-6 carbon atoms, wherein at least one hydrogen atom is substituted by a halogen, including but not limited to perhalo groups where all hydrogen atoms are replaced with halogen atoms. The haloalkyl chain can be either straight-chained or branched. Illustrative alkyl groups include trifluoromethyl, trifluoroethyl, trifluoropropyl, trifluorobutyl, and pentafluoroethyl. Similarly, a "haloalkenyl" group refers to a haloalkyl group having one or more double bonds present in the chain.

As used herein "heterocyclyl" or "heterocycle" refers to an unsaturated or partially saturated ring containing from 3 to 6 ring atoms and from 1 to 4 heteroatoms, which may be the same or different, selected from nitrogen, oxygen and sulfur. Illustrative heterocyclyl groups include oxirane, tetrahydrofuranyl, morpholino, pyrrolidinyl, tetrahydrothiophene, dioxane, and piperidinyl.

As used herein "aryl" refers to an aromatic ring system containing from 5 to 10 ring atoms. Illustrative aryl groups include phenyl and naphthyl.

As used herein "heteroaryl" refers to an heteroaromatic ring system containing from 5 to 10 ring atoms and from 1 to 4 heteroatoms, which may be the same or different, selected from nitrogen, oxygen and sulfur. Illustrative heteroaryl groups include pyridyl (pyridinyl), furan, thiophene, pyrazolyl, tetrazolyl, oxazolyl, thiazolyl, imidazolyl, and pyrimidinyl.

As used herein "optionally substituted" refers to a substitution of a hydrogen atom, which would otherwise be present on the substituent. When discussing ring systems, the optional substitution is typically with 1, 2, or 3 substituents replacing the normally-present hydrogen. When referencing straight and branched moieties, however, the number of substitutions can be more, occurring wherever hydrogen is usually present. The substitutions can be the same or different. Illustrative substitutions include nitro, —NR'R", cyano, —NR'COR''', alkyl, alkenyl, —C(O), —SO$_2$R''', —NR'SO$_2$R''', —SO$_2$NR'R", —CONR'R", —CONHC$_6$H$_5$, hydroxy, alkoxy, alkylsulfonyl, haloalkyl, haloalkenyl, haloalkoxy, mercapto (—SH), thioalkyl, halogen, cycloalkyl, heterocyclyl, aryl, or heteroaryl, where R' and R" are the same or different and each represents hydrogen or alkyl; or when R' and R" are each attached to a nitrogen atom, they may form a saturated or unsaturated heterocyclic ring containing from 4 to 6 ring atoms, and wherein R''' is alkyl or haloalkyl.

As used herein the phrase pesticidal or pesticidally, veterinary or veterinarily, or pharmaceutical or pharmaceutically acceptable salt refers to any salt of a compound disclosed herein which retains its biological properties and which is not toxic or otherwise undesirable for pesticidal, veterinary, or pharmaceutical use. Such salts may be derived from a variety of organic and inorganic counter-ions known in the art. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and like acids.

Salts further include, by way of example only, salts of non-toxic organic or inorganic acids, such as halides, such as , chloride and bromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

Described herein are single stereoisomer compounds according to formula (I). In certain cases, the depicted substituents can contribute to optical and/or stereoisomerism. Compounds having the same molecular formula but differing in the nature or sequence of bonding of their atoms or in the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers". When a compound has an asymmetric center, for example when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, *Angew. Chem.* 78: 413-447, *Angew. Chem., Int. Ed. Engl.* 5: 385-414 (errata: *Angew. Chem., Int. Ed. Engl.* 5: 511); Prelog and Helmchen, 1982, *Angew. Chem.* 94: 614-631, *Angew. Chem. Internat. Ed. Eng.* 21: 567-583; Mata and Lobo, 1993, *Tetrahedron: Asymmetry* 4: 657-668) or can be characterized by the manner in which the molecule rotates the plane of polarized light and is designated dextrorotatory or levorotatory (namely, as (+)- or (−)-isomers, respectively). A chiral compound can exist as either an individual enantiomer or as a mixture thereof. A mixture containing equal proportions of enantiomers is called a "racemic mixture".

The compounds disclosed herein possess one or more asymmetric centers. The compounds described herein can be produced as the individual (R)- or (S)-enantiomer or as a mixture or a racemate. In some embodiments, the compounds described herein have a single asymmetric center and are produced as the (S)-enantiomer. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In some embodiments, stereoisomers of the compounds provided herein are depicted upon treatment with base.

In certain embodiments, the compounds disclosed herein are "stereochemically pure." A stereochemically pure compound has a level of stereochemical purity that would be recognized as "pure" by those of skill in the art. Of course, this level of purity may be less than 100%. In certain embodiments, "stereochemically pure" designates a compound that is substantially free, i.e. at least about 85% or more, of alternate isomers. In particular embodiments, the compound is at least about 85%, about 90%, about 91%, about 92%, about 93%, about 94%, about 95%, about 96%, about 97%, about 98%, about 99%, about 99.5% or about 99.9% free of other isomers.

As used herein, the terms "subject" and "patient" are used interchangeably herein. The terms "subject" and "subjects" refer to a primate such as a monkey such as a cynomolgous monkey, a chimpanzee, and a human or non-primate animal. In one embodiment, the subject is a human. In another embodiment, the subject is a companion animal such as a dog or cat. In a further embodiment the subject is an animal of agricultural importance such as a sheep, cow, horse, goat, fish, pig, or domestic fowl (such as a chicken, turkey, duck, or goose).

In addition, a pharmaceutically acceptable prodrug of the compound represented by the formula (I) is also included in the present invention. The pharmaceutically acceptable prodrug refers to a compound having a group which can be converted into an amino group, a hydroxyl group, a carboxyl group, or the like, by solvolysis or under a physiological condition. Examples of the groups forming the prodrug include those as described in Prog. Med., 5, 2157-2161 (1985) or "Pharmaceutical Research and Development" (Hirokawa Publishing Company, 1990), vol. 7, Drug Design, 163-198. The term prodrug is used throughout the specification to describe any pharmaceutically acceptable form of a compound which, upon administration to a patient, provides the active compound. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The present invention includes all pharmaceutically acceptable isotopically-labelled compounds of the invention wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labelled compounds of the invention, such as those incorporating a radioactive isotope, may be useful in drug or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as 11C, $^{18}$F, $^{15}$O and $^{13}$N, can be useful in Positron Emission Topography (PET) studies for examining substrate receptor occupancy. Isotopically-labeled compounds of the invention can generally be prepared by conventional techniques known to those skilled in the art or by processes analogous to those described in the accompanying Examples and Preparations using an appropriate isotopically-labeled reagents in place of the non-labeled reagent previously employed.

Compounds

Isoxazoline derivatives have been disclosed in the art as having insecticidal and acaricidal activity. For example, WO2007/105814, WO2008/122375, and WO2009/035004 contain certain alkylene linked amides. WO2010/032437 discloses that the benzyl amide can be moved to the position ortho to the isoxazoline. Further, WO2007/075459 discloses phenyl isoxazolines substituted with 5- to 6-membered heterocycles, and WO2010/084067 and WO2010/025998 disclose phenyl isoxazolines substituted with 10- to 11-membered fused aryl and heteroaryls. Chiral processes for manufacturing isoxazolines have been reported in WO2011/104089 and WO2009/063910 and WO2017/176948. Isoxazoline azetidine derivatives were published in WO2012/017359. Some spiro-azetidine isobenzofuran derivatives for the treatment of diabetes and hyperlipidemia were described in WO2008/096746. In addition, spirocyclic isoxazolines were recently published in WO2012/120399. WO2014/039489 discloses spirocyclic derivatives as antiparasitic agents, including azetidinyl-isobenzofurans, but the citation does not teach or suggest isothiazolines as the heterocyclic moiety. WO2014/079935 discloses a preparation of [4-(isothiazol-3-yl)arylthio]acetamide derivatives as insecticides, and WO2014/001121 and WO2014/001120 each disclose the preparation of isothiazole derivatives as insecticidal compounds, but none contain the azetidinyl-isobenzofuran. WO2014/206911 discloses isothiazoline compounds, however, the teaching lacks any azetidenyl-isobenzofuran moiety. WO2014/079941 discloses insecticidal compounds based on N-(arylsulfanylmethyl) carboxamide derivatives. US2014378415 discloses isothiazoline compounds, however, the teaching lacks any azetidenyl-isobenzofuran moiety. WO2009/112275 relates to pesticidal condensed-ring aryl compounds, however, the teaching lacks any azetidenyl-isobenzofuran moiety. Parasiticidal spirocyclic azetidinyl-isobenzofuran derivatives having an isothiazoline moiety are disclosed in WO 2016/115315.

None of the foregoing references teach or suggest single enantiomer non-isoxazoline spirocyclic molecules, or processes of manufacturing such compounds. In particular, none of the forgoing references teach compounds according to formula I. Nor do the foregoing citations indicate that a single enantiomer of such compounds would be useful against a spectrum of parasitic species relevant to companion animals, livestock, birds, or fish, and especially against the range of parasitic morphological lifecycle stages.

Synthesis

Generally the compounds of the invention can be prepared, isolated or obtained by any method apparent to those of skill in the art. Exemplary methods of preparation are illustrated by the following schemes.

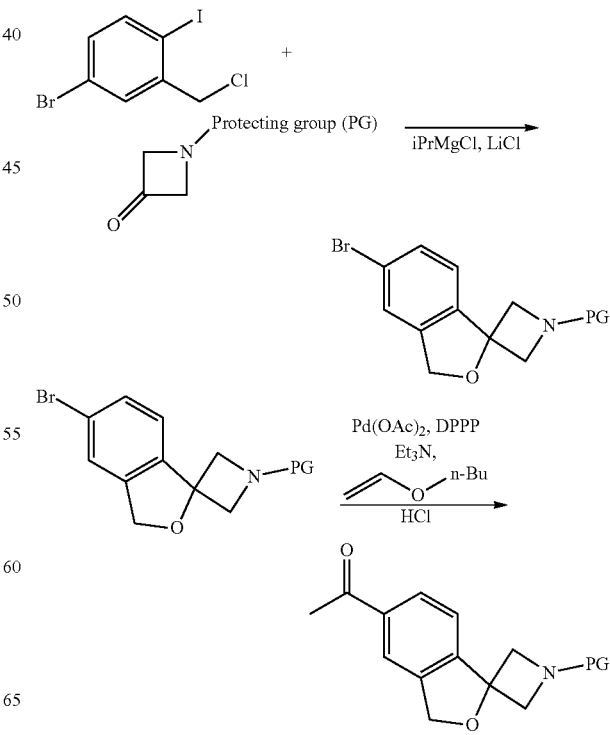

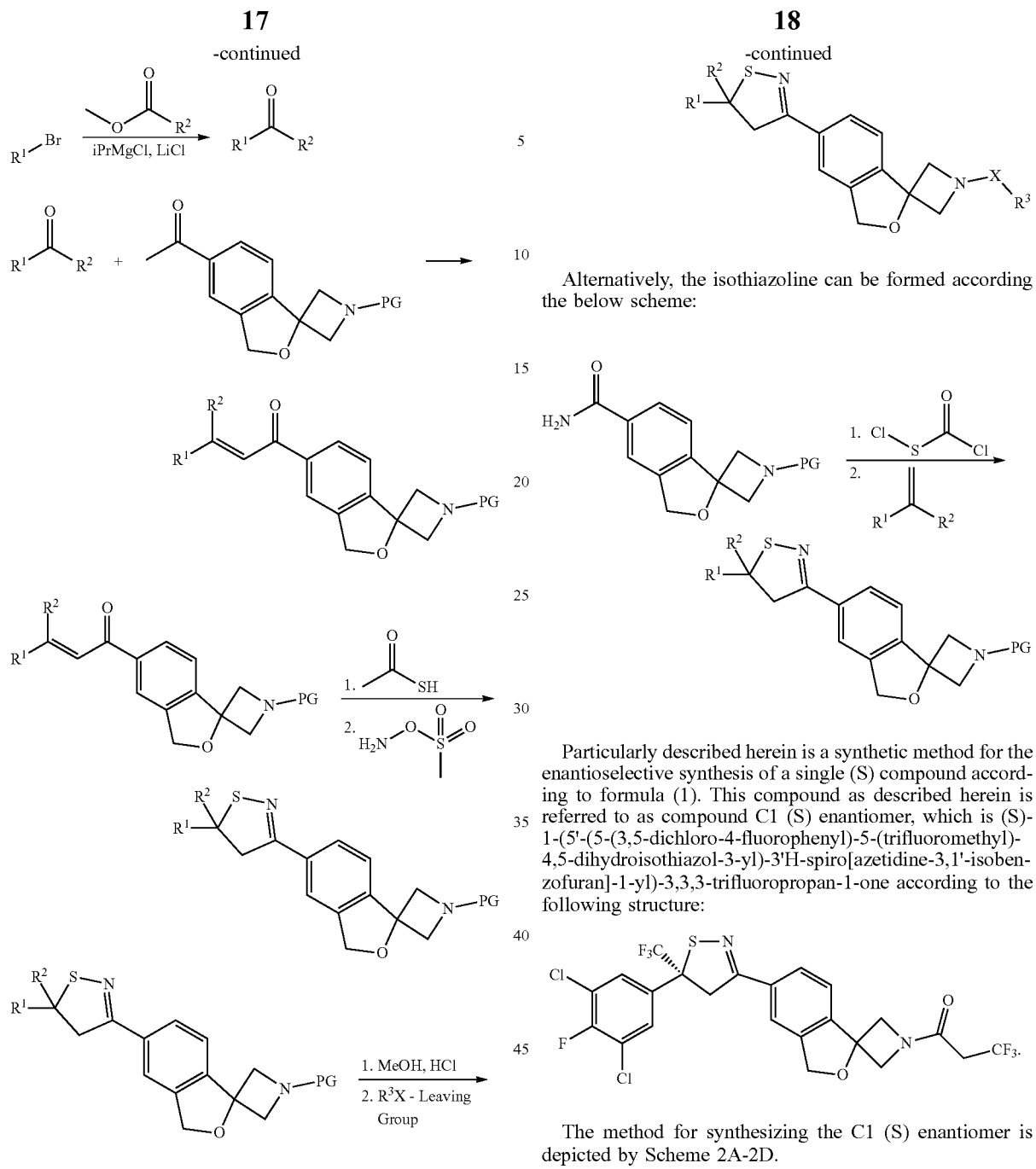

Alternatively, the isothiazoline can be formed according the below scheme:

Particularly described herein is a synthetic method for the enantioselective synthesis of a single (S) compound according to formula (1). This compound as described herein is referred to as compound C1 (S) enantiomer, which is (S)-1-(5'-(5-(3,5-dichloro-4-fluorophenyl)-5-(trifluoromethyl)-4,5-dihydroisothiazol-3-yl)-3'H-spiro[azetidine-3,1'-isobenzofuran]-1-yl)-3,3,3-trifluoropropan-1-one according to the following structure:

The method for synthesizing the C1 (S) enantiomer is depicted by Scheme 2A-2D.

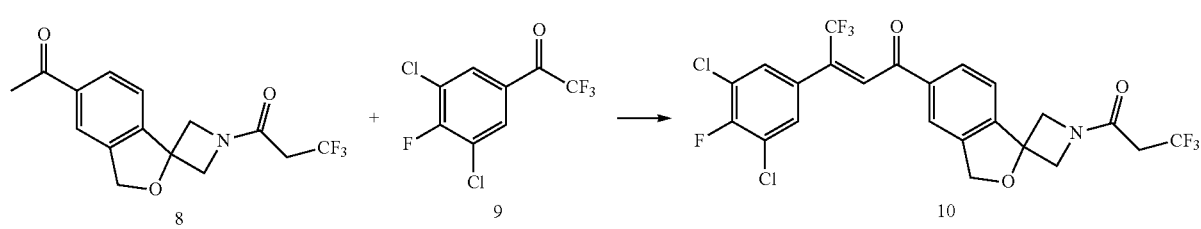

-continued

2B

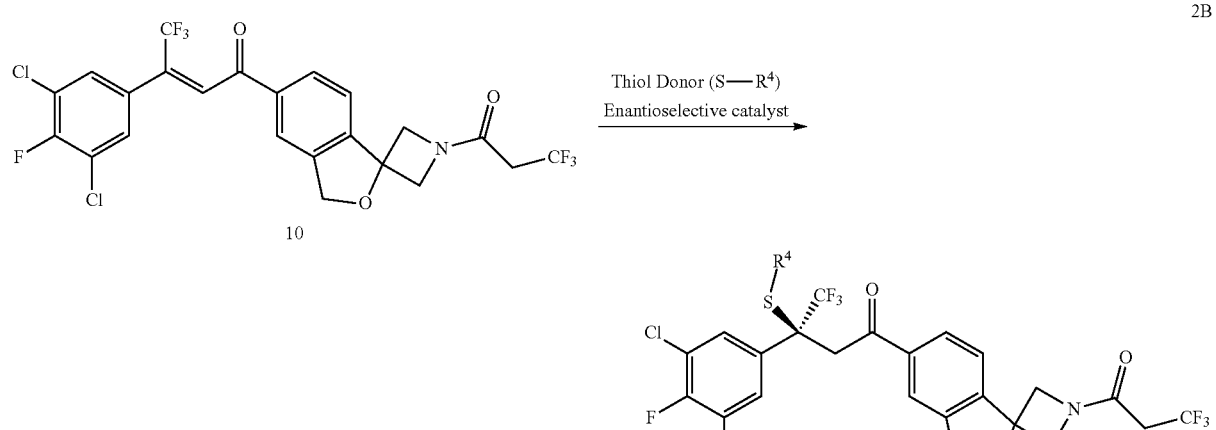

2C

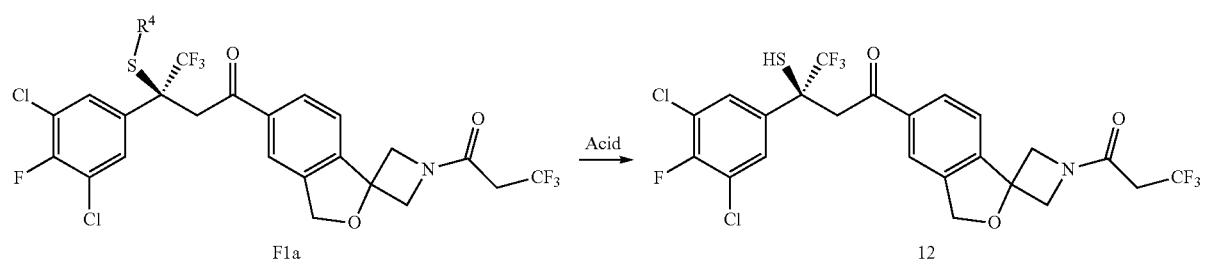

2D

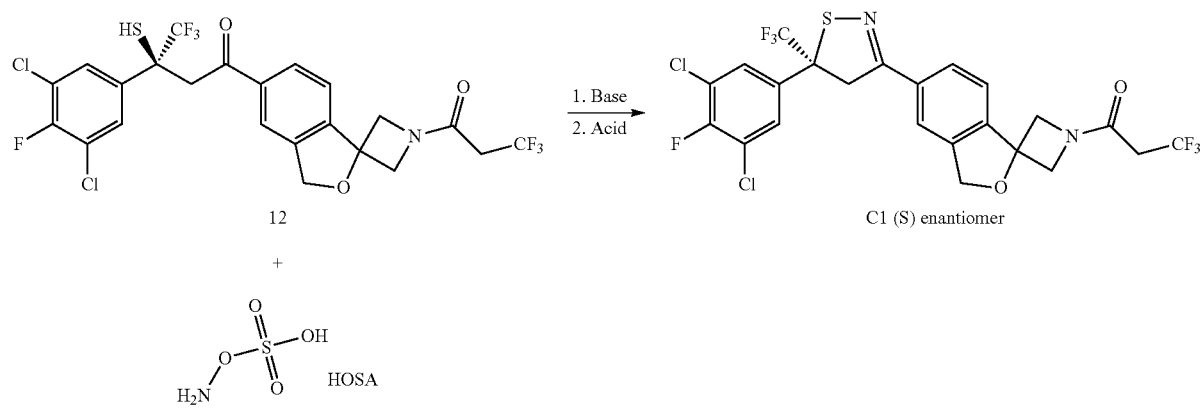

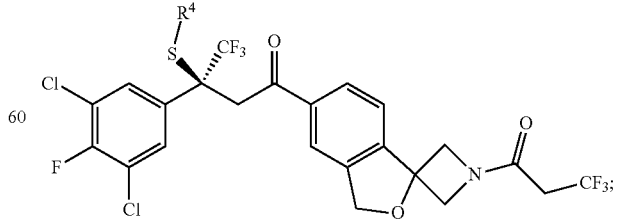

In one aspect, the synthesis of the compound comprises three steps comprising 3-intermediate compounds indicated as compound (10), a compound according to formula 1a (F1a) and compound (12) depicted in scheme 2. Accordingly, the first aspect of the method shown as scheme 2A includes preparing a mixture comprising 1-(5'-acetyl-3'H-spiro[azetidine-3,1'-isobenzofuran]-1-yl)-3,3,3-trifluoropropan-1-one and 1-(3,5-dichloro-4-fluorophenyl)-2,2,2-trifluoroethan-1-one and reacting the mixture to obtain a compound (Z)-3-(3,5-dichloro-4-fluorophenyl)-4,4,4-trifluoro-1-(1-(3,3,3-trifluoropropanoyl)-3'H-spiro[azetidine-3,1'-isobenzofuran]-5'-yl)but-2-en-1-one.

The second synthetic aspect for making the compound C1 (S)-enantiomer, is shown as scheme 2B and includes preparing a mixture comprising the compound of (a), an enantioselective catalyst; and a thiol donor and performing a reaction comprising reacting the mixture to form a thiol ether compound of formula (Ia):

Ia wherein $R^4$ is selected from hydrogen, optionally substituted $C_1$-$C_{10}$ alkyl, optionally substituted phenyl, and optionally substituted benzyl. In one aspect, $R^4$ is substituted with one or more $R^{4a}$, wherein $R^{4a}$ is an electron donating group selected from primary amines, secondary amines, tertiary amines, ethers, phenols, amides, esters, alkyl groups, phenyl, and vinyl groups. In another aspect $R^{4A}$ is selected from hydrogen, $C_1$-$C_{10}$ alkyl, and $C_1$-$C_{10}$ alkoxy. Thiol donor compounds include compounds of the formula S-$R^4$, wherein $R^4$ is as defined above. In one particular aspect, $R^4$ is benzyl and $R^{4A}$ is hydrogen or methoxy; such compounds include the thiol donors benzyl mercaptan and 4-methoxybenzyl mercaptan. In one particular aspect, the thiol donor is 4-methoxybenzyl mercaptan (also known as PMBSH).

The enantiomeric specificity of the compound during synthesis is achieved by utilizing an enantioselective catalyst. Such catalysts are generally known in the art (see Malerich, J. P., et al., *J. Am. Chem. Soc.*, 130 (44), pp. 14416-14417 (2008) and Guant, M. J., et al., *Drug Disc. Today* 12(1/2), pp. 8-27, (2006)). Suitable exemplary and non-limiting enantioselective catalysts include secondary amine containing catalysts, thiourea containing catalysts, and squaramide containing catalysts. In one aspect, the enantioselective catalyst is a squaramide containing catalyst. In another particular aspect, the squaramide containing catalyst is 3-((3,5-bis(trifluoromethyl)phenyl)amino)-4-(((R)-(6-methoxyquinolin-4-yl)((1S,2R,4S,5R)-5-vinylquinuclidin-2-yl)methyl)amino)cyclobut-3-ene-1,2-dione according to the structure:

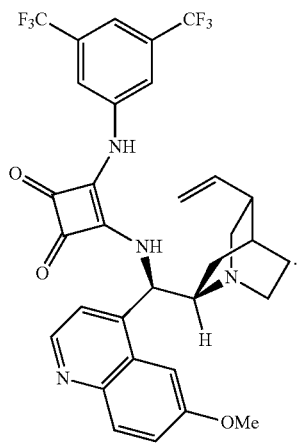 [SMILES: C=CC1CN2CCC1C[C@@H]2[C@H](Nc1c(Nc2cc(C(F)(F)F)cc(C(F)(F)F)c2)c(=O)c1=O)c1ccnc2ccc(OC)cc12]

The third synthetic aspect for making the compound C1 (S)-enantiomer, is shown as scheme 2C and includes cleaving the thiol ether formed in scheme 2B to form a compound (S)-3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5'-yl)butan-1-one. In one aspect, the cleavage is an acid-based cleavage. The fourth synthetic aspect is shown as scheme 2D and includes preparing a mixture comprising the compound of (c) and hydroxylamine-O-sulfonic acid and reacting the mixture to form the compound of C1 (S) enantiomer. Additionally contemplated methods for synthesizing the C1 (S) enantiomer compound are described for each of the synthetic intermediates.

One embodiment described herein is the compound (Z)-3-(3,5-dichloro-4-fluorophenyl)-4,4,4-trifluoro-1-(1-(3,3,3-trifluoropropanoyl)-3'H-spiro[azetidine-3,1'-isobenzofuran]-5'-yl)but-2-en-1-one according to the structure:

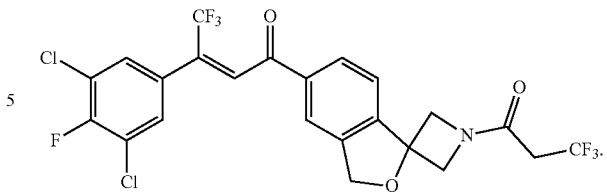

This compound is made according the scheme 2A, which includes preparing a mixture that includes (a) 1-(5'-acetyl-3'H-spiro[azetidine-3,1'-isobenzofuran]-1-yl)-3,3,3-trifluoropropan-1-one and (b) 1-(3,5-dichloro-4-fluorophenyl)-2,2,2-trifluoroethan-1-one and reacting the mixture. In one aspect (a) and (b) are dissolved in an organic solvent. In another aspect, the reaction mixture includes an amine-containing base having a pKb of around 8 to about 12, such as triethylamine, pyridine, methylamine, benzylamine, n-butylamine, and the like. In another aspect, the mixture is heated to a specified temperature comprising about 40° C. to about 90° C., about 40° C. to about 80° C., or about 50° C. to about 60° C., including each integer within the specified ranges. In another aspect, the mixture is heated to a specified temperature over a time range comprising about 30 minutes to about 6 hours, about 1 hour to about 4 hours, or about 1 hour to about 2 hours, including each integer of time within the specified ranges. In another aspect, the mixture is held at a specified temperature for a time comprising about 1 hour to about 8 hours, 1 hour to about 6 hours, or 1 hour to about 4 hours, including each integer of time within the specified ranges. Additional washing and purification steps can be included as is known in the art.

Another embodiment is a synthetic intermediate of the C1 (S) enantiomer compound, which is (S)-3-(3,5-dichloro-4-fluorophenyl)-4,4,4-trifluoro-3-((4-methoxybenzyl)thio)-1-(1-(3,3,3-trifluoropropanoyl)-3'H-spiro[azetidine-3,1'-isobenzofuran]-5'-yl)butan-1-one according to the structure:

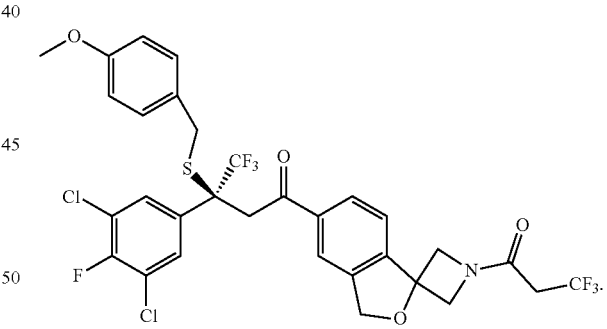

The compound is made according to scheme 2B, which includes preparing a mixture including the compound (Z)-3-(3,5-dichloro-4-fluorophenyl)-4,4,4-trifluoro-1-(1-(3,3,3-trifluoropropanoyl)-3'H-spiro[azetidine-3,1'-isobenzofuran]-5'-yl)but-2-en-1-one, an enantioselective catalyst, and p-methoxybenzyl mercaptan. In one aspect, the mixture further includes a buffering agent, such as di-potassium phosphate and an organic solvent. In another aspect, the mixture is cooled to a temperature of about 20° C. to about -40° C., about 4° C. to about -30° C., or about -5° C. to about -25° C. including each integer within the specified ranges. In another aspect, the enantioselective catalyst is added to the mixture over a time period comprising about 1 hour to about 96 hours, about 10 hours to about 80 hours, about 20 hours to about 60 hours, or about 40 hours to about 50 hours, including each integer of time within the specified ranges. Additional washing and purification steps can be included as is known in the art.

Another embodiment is a synthetic intermediate of the C1 (S) enantiomer compound, which is (S)-3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5'-yl)butan-1-one according to the structure:

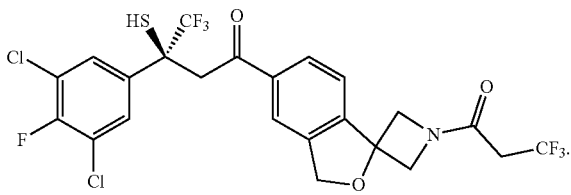 [SMILES: O=C(C[C@](S)(c1cc(Cl)c(F)c(Cl)c1)C(F)(F)F)c1ccc2c(c1)COC21CN(C(=O)CC(F)(F)F)C1]

The compound is made according to scheme 2C, which comprises preparing a mixture that includes (S)-3-(3,5-dichloro-4-fluorophenyl)-4,4,4-trifluoro-3-((4-methoxybenzyl)thio)-1-(1-(3,3,3-trifluoropropanoyl)-3'H-spiro[azetidine-3,1'-isobenzofuran]-5'-yl)butan-1 -one, an organic solvent, adding an acid, and reacting the mixture. In one aspect, the acid has a pKa comprising about −14 to about 5, about −14 to about 1, or about −14 to about -5, or a pKa of less than 1, including each integer within the specified ranges. Such acids suitable for synthetic chemical methods are known and include hydrochloric acid, trifluoroacetic acid, triflic acid and the like. In another aspect, the temperature of the mixture is maintained at a temperature of less than about 20° C., less than about 15° C., or less than about 10° C. or about −20° C. to about 30° C., or about 0° C. to about 10° C., including each integer within the specified range. In another aspect, the acid is added to the mixture over a time period comprising about 5 minutes to about 60 minutes, about 5 minutes to about 30 minutes, or about 20 minutes, including each integer within the specified ranges of time. Additional washing and purification steps can be included as is known in the art.

The compound C1 (S) enantiomer is made from the third intermediate according to scheme 2D, which comprises preparing a mixture including the compound (S)-3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5'-yl)butan-1-one, an organic solvent, and hydroxylamine-O-sulfonic acid and reacting the mixture. In one aspect, the mixture is cooled to a temperature of 20° C. to about −40° C., about 4° C. to about −30° C., or about −5° C. to about −25° C. including each integer within the specified ranges. In one aspect, a base is subsequently added to the mixture and this resultant mixture is allowed to react. In another aspect, the base is added over a time period of about 10 minutes to about 6 hours, about 10 minutes to about 4 hours, or about 1 hour to about 3 hours, including each integer within the specified range. In another aspect, the reaction is quenched by the addition of an acid to the reaction. Suitable acids include those having a pKa of about -14 to about 5, such as hydrochloric acid. In another aspect, the temperature of the mixture while adding the acid is maintained at a temperature of less than about 20° C., less than about 15° C., or less than about 10° C. or about −20° C. to about 30° C., or about 0° C. to about 10° C., including each integer within the specified ranges. Suitable bases include those having a pKb of about −2 to about 9, such as, but not limited to, potassium hydroxide, sodium hydroxide, calcium hydroxide, Hunig's Base, DBU, N-methylmorpholine, pyridine, 2,6-di-tert-butylpyridine, 2,6-lutidine, TMEDA, DABCO, and 2,2,6,6-tetramethylpiperidine.

The synthetic preparation of the compounds described herein are generally carried out in an organic solvent, which are generally known in the art. Exemplary and non-limiting solvents include both water miscible and water-immiscible solvents, polar and non-polar solvents. Exemplary and non-limiting solvents include pentane, cyclopentane, hexane, cyclohexane benzene, toluene, 1,4-dioxane, diethyl ether, tetrahydrofuran, methyl tertbutyl ether, dimethyl sulfoxide, and the like.

Compositions and Methods of Administration

The compounds of formula (I) used in the methods disclosed herein can be administered in certain embodiments using veterinary, pharmaceutical, or pesticidal compositions including at least one compound of formula (I), if appropriate in the salt form, either used alone or in the form of a combination with one or more compatible and veterinarily, pharmaceutically, or pesticidally acceptable carriers, such as diluents or adjuvants, or with another agent. There are provided compositions which comprise an isothiazoline derivative of formula (I) or a salt thereof, and an acceptable excipient, carrier or diluent. The composition can also be in a variety of forms which include, but are not limited to, oral formulations, injectable formulations, and topical, dermal or subdermal formulations.

The composition can be in a form suitable for oral use, for example, as dietary supplements, troches, lozenges, chewables, tablets, hard or soft capsules, emulsions, aqueous or oily suspensions, aqueous or oily solutions, dispersible powders or granules, syrups, or elixirs. Compositions intended for oral use can be prepared according to any method known in the art for the manufacture of veterinary, pharmaceutical, or pesticidal compositions and such compositions can contain one or more agents selected from the group consisting of sweetening agents, bittering agents, flavoring agents, coloring agents and preserving agents in order to provide elegant and palatable preparations.

Tablets can contain the active ingredient in admixture with non-toxic, pharmaceutically acceptable excipients which are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period.

Formulations for oral use can be hard gelatin capsules, wherein the active ingredient is mixed with an inert solid diluent, for example, calcium carbonate, calcium phosphate or kaolin. Capsules can also be soft gelatin capsules, wherein the active ingredient is mixed with water or miscible solvents such as propylene glycol, PEGs and ethanol, or an oil medium, for example, peanut oil, liquid paraffin, or olive oil.

The compositions can also be in the form of oil-in-water or water-in-oil emulsions. The oily phase can be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions can also contain sweetening agents, bittering agents, flavoring agents, and preservatives.

In one embodiment of the formulation, the composition is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids. Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously. In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example, $C_8$-$C_{10}$ caprylic/capric triglyceride. In another embodiment, the oily phase will represent a % v/v range selected from the group consisting of about 2 to about 15%; about 7 to about 10%; and about 8 to about 9% v/v of the microemulsion. The aqueous phase includes, for example, water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion. Surfactants for the microemulsion include diethylene glycol monoethyl ether, dipropylene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol. Some compounds are common to the three components discussed above, for example, aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2.

In another embodiment for the amount of cosurfactant, there will be from about 25 to about 75% v/v of surfactant and from about 10 to about 55% v/v of cosurfactant in the microemulsion.

Oily suspensions can be formulated by suspending the active ingredient in a vegetable oil, for example, atachis oil, olive oil, sesame oil or coconut oil, or in mineral oil such as liquid paraffin. The oily suspensions can contain a thickening agent, for example, beeswax, hard paraffin or cetyl alcohol. Sweetening agents such as sucrose, saccharin or aspartame, bittering agents, and flavoring agents can be added to provide a palatable oral preparation. These compositions can be preserved by the addition of an anti-oxidant such as ascorbic acid, or other known preservatives.

Aqueous suspensions can contain the active material in admixture with excipients suitable for the manufacture of aqueous suspensions. Such excipients are suspending agents, for example, sodium carboxymethylcellulose, methylcellulose, hydroxypropylmethylcellulose, sodium alginate, polvinylpyrrolidone, gum tragacanth and gum acacia; dispersing or wetting agents can be a naturally-occuring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example, polyethylene sorbitan monooleate. The aqueous suspensions can also contain one or more preservatives, for example, ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, can also be present.

Syrups and elixirs can be formulated with sweetening agents, for example, glycerol, propylene glycol, sorbitol or sucrose. Such formulations may also contain a demulcent, a preservative, flavoring agent(s) and coloring agent(s).

The compositions can be in the form of a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent or solvent, for example, as a solution in 1,3-butane diol. Among the acceptable vehicles and solvents that can be employed are water, Ringer's solution and isotonic sodium chloride solution. Cosolvents such as ethanol, propylene glycol or polyethylene glycols can also be used. Preservatives, such as phenol or benzyl alcohol, can be used.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Topical, dermal and subdermal formulations can include emulsions, creams, ointments, gels or pastes.

Organic solvents that can be used in the invention include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, compositions of the present invention may include plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$-$C_{12}$) triglycerides.

Dosage forms can contain from about 0.5 mg to about 5 g of an active agent.

In one embodiment of the invention, the active agent is present in the formulation at a concentration of about 0.05 to 10% weight/volume.

The compounds of formula (I) can be employed as such or in the form of their preparations or formulations as combinations with other pesticidally active substances, such as, for example, insecticides, attractants, sterilants, nematicides, acaricides, fungicides, herbicides, and with safeners, fertilizers and/or growth regulators.

The compounds of formula (I) according to the invention may be combined with one or more agents having the same sphere of activity, for example, to increase activity, or with substances having another sphere of activity, for example, to broaden the range of activity. The compounds of the present invention may also be combined with so-called repellents. By combining the compounds of the formula I with other suitable parasiticides, not only the parasiticidal activity can be enhanced, but the greatest part of those parasites that produce great economic damage will be covered. Moreover, this action will contribute substantially to avoiding the formation of resistance. Preferred groups of combination partners and especially preferred combination partners are named in the following, whereby combinations may contain one or more of these partners in addition to a compound of formula I. Suitable partners may also be afoxolaner, sarolaner, fluralaner, or a combination thereof. Any of the individually listed agents can be used in combination with compounds of formula (I) along with any other one or more listed agents independently.

Suitable partners in the mixture may be biocides, namely insecticides and acaricides with a varying mechanism of activity, for example, chitin synthesis inhibitors, growth regulators, active ingredients which act as juvenile hormones, active ingredients which act as adulticides, broadband insecticides, broadband acaricides and nematicides, and also anthelminthics and insect- and acarid-deterring substances, repellents or detachers. Non-limiting examples of suitable insecticides and acaricides are:

| | | |
|---|---|---|
| 1. | Abamectin | |
| 2. | Acephate | |
| 3. | Acequinocyl | |
| 4. | Acetamiprid | |
| 5. | Acetoprole | |
| 6. | Acrinathrin | |
| 7. | AKD-1022 | |
| 8. | Alanycarb | |
| 9. | Aldicarb | |
| 10. | Aldoxycarb | |
| 11. | Allethrin | |
| 12. | Alpha-cypermethrin | |
| 13. | Alphamethrin | |
| 14. | Amidoflumet | |
| 15. | Amitraz | |
| 16. | Anabasine | |
| 17. | Avermectin B1 | |
| 18. | Azadirachtin | |
| 19. | Azamethiphos | |
| 20. | Azinphos-ethyl | |
| 21. | Azinphos-methyl | |
| 22. | Azocyclotin | |
| 23. | *Bacillus subtil*, toxin | |
| 24. | *Bacillus thuringiensis* | |
| 25. | Benclothiaz | |

-continued

| | |
|---|---|
| 26. | Bendiocarb |
| 27. | Benfuracarb |
| 28. | Bensultap |
| 29. | Benzoximate |
| 30. | Beta-cyfluthrin |
| 31. | Beta-cypermethrin |
| 32. | Bifenazate |
| 33. | Bifenthrin |
| 34. | Bioallethrin |
| 35. | Bioresmethrin |
| 36. | Bistrifluron |
| 37. | BPMC |
| 38. | Brofenprox |
| 39. | Bromophos A |
| 40. | Bromopropylate |
| 41. | Bufencarb |
| 42. | Buprofezin |
| 43. | Butocarboxim |
| 44. | Cadusafos |
| 45. | Carbaryl |
| 46. | Carbofuran |
| 47. | Carbophenothion |
| 48. | Carbosulfan |
| 49. | Cartap |
| 50. | Chloethocarb |
| 51. | Chlorantraniliprole |
| 52. | Chlorethoxyfos |
| 53. | Chlorfenapyr |
| 54. | Chlorfenvinphos |
| 55. | Chlorfluazuron |
| 56. | Chlormephos |
| 57. | Chlorpyrifos |
| 58. | Chlorpyrifos-methyl |
| 59. | Chromafenozide |
| 60. | Cis-Resmethrin |
| 61. | Clofentezin |
| 62. | Clothianidin |
| 63. | Coumaphos |
| 64. | Cyanophos |
| 65. | Cycloprothrin |
| 66. | Cyenopyrafen |
| 67. | Cyflumetofen |
| 68. | Cyfluthrin |
| 69. | Cyhalothrin |
| 70. | Cyhexatin |
| 71. | Cymiazole |
| 72. | Cypermethrin |
| 73. | Cyphenothrin |
| 74. | Cyromazine |
| 75. | Deltamethrin |
| 76. | Demeton M |
| 77. | Demeton S |
| 78. | Demeton-S-methyl |
| 79. | Diafenthiuron |
| 80. | Diazinon |
| 81. | Dichlofenthion |
| 82. | Dichlorvos |
| 83. | Dicofol |
| 84. | Dicrotophos |
| 85. | Dicyclanil |
| 86. | Diethion |
| 87. | Diflovidazin |
| 88. | Diflubenzuron |
| 89. | Dimefluthrin |
| 90. | Dimethoate |
| 91. | Dimethylvinphos |
| 92. | Dinobuton |
| 93. | Dinocap |
| 94. | Dinotefuran |
| 95. | Diofenolan |
| 286. | Afoxolaner |
| 96. | Dioxathion |
| 97. | Disulfoton |
| 98. | DNOC |
| 99. | Doramectin |
| 100. | DPX-HGW86 |
| 101. | Edifenphos |
| 102. | Emamectin |
| 103. | Empenthrin |

-continued

| | |
|---|---|
| 104. | Endosulfan |
| 105. | Esfenvalerat |
| 106. | Ethiofencarb |
| 107. | Ethion |
| 108. | Ethiprole |
| 109. | Ethoprophos |
| 110. | Etofenprox |
| 111. | Etoxazole |
| 112. | Etrimphos |
| 113. | Fenamiphos |
| 114. | Fenazaquin |
| 115. | Fenbutatin oxide |
| 116. | Fenitrothion |
| 117. | Fenobucarb |
| 118. | Fenothiocarb |
| 119. | Fenoxycarb |
| 120. | Fenpropathrin |
| 121. | Fenpyroximate |
| 122. | Fenthion |
| 123. | Fenvalerate |
| 124. | Fipronil |
| 125. | Flonicamid |
| 126. | Fluacrypyrim |
| 127. | Fluazinam |
| 128. | Fluazuron |
| 129. | Flubendiamide |
| 130. | Flucycloxuron |
| 131. | Flucythrinate |
| 132. | Flufenerim |
| 133. | Flufenoxuron |
| 134. | Flufenprox |
| 135. | Flumethrin |
| 136. | Fonophos |
| 137. | Formothion |
| 138. | Fosthiazate |
| 139. | Fubfenprox |
| 140. | Furathiocarb |
| 141. | Gamma-cyhalothrin |
| 142. | Halfenprox |
| 143. | Halofenozide |
| 144. | HCH |
| 145. | Heptenophos |
| 146. | Hexaflumuron |
| 147. | Hexythiazox |
| 148. | Hydramethylnon |
| 149. | Hydroprene |
| 150. | Imidacloprid |
| 151. | Imiprothrin |
| 152. | Indoxacarb |
| 153. | insect-active fungi |
| 154. | insect-active nematodes |
| 155. | insect-active viruses |
| 156. | Iprobenfos |
| 157. | Lsofenphos |
| 158. | Isoprocarb |
| 159. | Isoxathion |
| 160. | Ivermectin |
| 161. | Karanjin |
| 162. | Kinoprene |
| 163. | Lamba-Cyhalothrin |
| 164. | Lepimectin |
| 165. | Lufenuron |
| 166. | Malathion |
| 167. | Mecarbam |
| 168. | Mesulfenphos |
| 169. | Metaflumizone |
| 170. | Metaldehyde |
| 171. | Methamidophos |
| 172. | Methidathion |
| 173. | Methiocarb |
| 174. | Methomyl |
| 175. | Methoprene |
| 176. | Methothrin |
| 177. | Methoxyfenozide |
| 178. | Metofluthrin |
| 179. | Metolcarb |
| 180. | Metoxadiazone |
| 181. | Mevinphos |
| 182. | Milbemectin |

-continued

| | |
|---|---|
| 183. | Milbemycin oxime |
| 184. | Monocrotophos |
| 185. | Moxidectin |
| 186. | Naled |
| 187. | Nicotine |
| 188. | Nitenpyram |
| 189. | Novaluron |
| 190. | Noviflumuron |
| 287. | Sarolaner |
| 191. | Omethoate |
| 192. | Oxamyl |
| 193. | Oxydemethon M |
| 194. | Oxydeprofos |
| 195. | Parathion |
| 196. | Parathion-methyl |
| 197. | Permethrin |
| 198. | Phenothrin |
| 199. | Phenthoate |
| 200. | Phorate |
| 201. | Phosalone |
| 202. | Phosmet |
| 203. | Phosphamidon |
| 204. | Phoxim |
| 205. | Pirimicarb |
| 206. | Pirimiphos A |
| 207. | Pirimiphos M |
| 208. | Polynactins |
| 209. | Prallethrin |
| 210. | Profenofos |
| 211. | Profluthrin |
| 212. | Promecarb |
| 213. | Propafos |
| 214. | Propargite |
| 215. | Propoxur |
| 216. | Prothiofos |
| 217. | Prothoate |
| 218. | Protrifenbute |
| 219. | Pymetrozine |
| 220. | Pyrachlofos |
| 221. | Pyrafluprole |
| 222. | Pyresmethrin |
| 223. | Pyrethrin |
| 224. | Pyrethrum |
| 225. | Pyridaben |
| 226. | Pyridalyl |
| 227. | Pyridaphenthion |
| 228. | Pyrifluquinazon |
| 229. | Pyrimidifen |
| 230. | Pyriprole |
| 231. | Pyriproxyfen |
| 232. | Quinalphos |
| 233. | Resmethrin |
| 234. | Rotenone |
| 235. | RU 15525 |
| 236. | Sabadilla |
| 237. | Salithion |
| 238. | Selamectin |
| 239. | Silafluofen |
| 240. | Spinetoram |
| 241. | Spinosad |
| 242. | Spirodiclofen |
| 243. | Spiromesifen |
| 244. | Spirotetramat |
| 245. | Sulcofuron sodium |
| 246. | Sulfluramid |
| 247. | Sulfotep |
| 248. | Sulfur |
| 249. | Sulprofos |
| 250. | Tau-fluvalinate |
| 251. | Tebufenozide |
| 252. | Tebufenpyrad |
| 253. | Tebupirimfos |
| 254. | Teflubenzuron |
| 255. | Tefluthrin |
| 256. | Temephos |
| 257. | Terbufos |
| 258. | Tetrachlorvinphos |
| 259. | Tetradifon |
| 260. | Tetramethrin |

| | | |
|---|---|---|
| 261. | Thiacloprid | |
| 262. | Thiamethoxam | |
| 263. | Thiocyclam | |
| 264. | Thiodicarb | |
| 265. | Thiofanox | |
| 266. | Thionazin | |
| 267. | Thiosultap | |
| 268. | Thuringiensin | |
| 269. | Tolfenpyrad | |
| 270. | Tralomethrin | |
| 271. | Transfluthrin | |
| 272. | Triarathene | |
| 273. | Triazamate | |
| 274. | Triazophos | |
| 275. | Trichlorfon | |
| 276. | Triflumuron | |
| 277. | Trimethacarb | |
| 278. | Vamidothion | |
| 279. | Vaniliprole | |
| 280. | XMC (3,5,-Xylylmethylcarbamate) | |
| 281. | Xylylcarb | |
| 282. | Zeta-cypermethrin | |
| 283. | Zetamethrin | |
| 284. | ZXI 8901 | |
| 285. | Demiditraz | |
| 288. | Fluralaner | |

Non-limitative examples of suitable anthelmintics, a few representatives have anthelmintic activity in addition to the insecticidal and acaricidal activity include:

| | | |
|---|---|---|
| (A1) Abamectin | (A2) Albendazole | (A3) Cambendazole |
| (A4) Closantel | (A5) Diethylcarbamazine | (A6) Doramectin |
| (A7) Emodepside | (A8) Eprinomectin | (A9) Febantel |
| (A10) Fendendazole | (A11) Flubendazole | (A12) Ivermectin |
| (A13) Levamisol | (A14) Mebendazole | (A15) Milbemectin |
| (A16) Milbemycin Oxime | (A17) Morantel | (A18) Moxidectin |
| (A19) Nitroscanate | (A20) Omphalotin | (A21) Oxantel |
| (A22) Oxfendazole | (A23) Oxibendazole | (A24) Phenothiazine |
| (A25) Piperazine | (A26) PNU-97333 | (A27) PNU-141962 |
| (A28) Praziquantel | (A29) Pyrantel | (A30) Thiabendazole |
| (A31) Triclabendazole amino acetonitrile derivatives named in WO2005044784 | | |

Non-limitative examples of suitable repellents and detachers include:
(R1) DEET (N, N-diethyl-m-toluamide)
(R2) KBR 3023, picaridin, N-butyl-2-oxycarbonyl-(2-hydroxy)-piperidine
(R3) Cymiazole, N,-2,3-dihydro-3-methyl-1 ,3-thiazol-2-ylidene-2,4-xylidene The above-specified combination partners are best known to specialists in this field. Most are described in various editions of the Pesticide Manual, The British Crop Protection Council, London, in various editions of the Compendium of Veterinary Products, North American Compendiums, Inc., in various editions of the Compendium of Pesticide Common Names and in various editions of the Merck Veterinary Manual and The Merck Index, Merck & Co., Inc., Rahway, N.J., USA.

The pharmaceutical preparation comprising the isothiazoline derivatives, for delivery to a human or other mammal, is preferably in unit dosage form, in which the preparation is subdivided into unit doses containing an appropriate quantity of the active component. The unit dosage form can be a packaged preparation containing discrete quantities of the preparation, such as packaged tablets, capsules, and powders in vials or ampoules. Also, the unit dosage form can be a capsule, tablet or lozenge itself, or it can be an appropriate number of any of these in packaged form.

The quantity of active component in a unit dose preparation can be varied or adjusted from about 0.1 mg to about 1000 mg, according to the particular application and the potency of the active component. The composition can, if desired, also contain other compatible therapeutic agents.

In therapeutic use for the treatment or prevention of a parasitic infection in a human or other mammal, the compounds utilized in the method of treatment are administered at an initial dosage of about 0.1 mg/kg to about 100 mg/kg per interval. Preferred intervals may be daily, weekly, monthly, quarterly, semi-annually, or annually. The dosages can be varied depending on the requirements of the patient, for example, the size of the human or mammal being treated, the severity of the condition being treated, the route of administration, and the potency of the compound(s) being used. Determination of the proper dosage and route of administration for a particular situation is within the skill of the practitioner. Generally, the treatment will be initiated with smaller dosages which are less than the optimum dose of the compound, which can be increased in small increments until the optimum effect under the particular circumstances of the infection is reached. For convenience, the total daily dosage can be divided and administered in portions during the day if desired.

The compounds of the present invention and compositions comprising a therapeutically effective amount of a Formula (I) compound and veterinarily acceptable salt thereof, and a veterinarily acceptable excipient, diluent, or carrier are useful as ectoparasiticides for the control and treatment of infections or infestations manifested by said ectoparasite in an animal. The compounds of the present invention are illustrated herein to have utility as an ectoparasiticide, in particular, as an acaricide and insecticide. They may, in particular, be used in the fields of veterinary medicine, livestock husbandry and the maintenance of public health: against acarids, insects, and copepods which are parasitic upon vertebrates, particularly warm-blooded vertebrates, including companion animals, livestock, and fowl and cold-blooded vertebrates like fish. Non-limiting examples of ectoparasites include: ticks (e.g., *Ixodes* spp., (e.g., *I. ricinus*, *I. hexagonus*), *Rhipicephalus* spp. (e.g., *R. sanguineus*), *Boophilus* spp., *Amblyomma* spp. (e.g., *A. americanum*, *A. maculatum*, *A. triste*, *A. parvum*, *A. cajennense*, *A. ovale*, *A. oblongoguttatum*, *A. aureolatum*, *A. cajennense*), *Hyalomma* spp., *Haemaphysalis* spp., *Dermacentor* spp. (e.g., *D. variabilis*, *D. andersoni*, *D. marginatus*), *Ornithodorus* spp., and the like); mites (e.g., *Dermanyssus* spp., *Sarcoptes* spp. (e.g., *S. scabiei*), *Psoroptes* spp. (e.g., *P. bovis*), *Otodectes* spp., *Chorioptes* spp., *Demodex* spp., (e.g., *D. folliculorum*, *D. canis*, and *D. brevis*) and the like); chewing and sucking lice (e.g., *Damalinia* spp., *Linognathus* spp., *Cheyletiella* spp., *Haematopinus* spp., *Solenoptes* spp., *Trichodectes* spp., *Felicola* spp., and the like); fleas (e.g., *Siphonaptera* spp., *Ctenocephalides* spp., and the like); biting flies, midges, and mosquitoes (e.g., *Tabanidae* spp., *Haematobia* spp., *Musca* spp., *Stomoxys* spp., *Dematobia* spp., *Cochliomyia* spp., *Simuliidae* spp., *Ceratopogonidae* spp., *Psychodidae* spp., *Aedes* spp., *Culex* spp., *Anopheles* spp., *Lucilia* spp., *Phlebotomus* spp., *Lutzomyia* spp., and the like); bed bugs (e.g., insects within the genus *Cimex* and family Cimicidae); and grubs (e.g., *Hypoderma bovis*, *H. lineatum*); and copepods (e.g., sea lice within the Order Siphonostomatoida, including genera *Lepeophtheirus* and *Caligus*).

The compound of the present invention can also be used for the treatment of endoparasites, for example, helminths (e.g., trematodes, cestodes, and nematodes) including heartworm, roundworm, hookworm, whipworm, fluke, and tapeworm. The gastrointestinal roundworms include, for example, *Ostertagia ostertagi* (including inhibited larvae), *O. lyrata, Haemonchus placei, H. similis, H. contortus, Toxocara canis, T. leonina, T. cati, Trichostrongylus axei, T. colubriformis, T. longispicularis, Cooperia oncophora, C. pectinata, C. punctata, C. surnabada* (syn. *mcmasteri*), *C. spatula, Ascaris suum, Hyostrongylus rubidus, Bunostomum phlebotomum, Capillaria bovis, B. trigonocephalum, Strongyloides papillosus, S. ransomi, Oesophagostomum radiatum, O. dentatum, O. columbianum, O. quadrispinulatum, Trichuris* spp., and the like. Other parasites include: hookworms (e.g., *Ancylostoma caninum, A. tubaeforme, A. braziliense, Uncinaria stenocephala*); lungworms (e.g., *Dictyocaulus viviparus* and *Metastrongylus* spp); eyeworms (e.g., *Thelazia* spp.); parasitic stage grubs (e.g., *Hypoderma bovis, H. lineatum, Dermatobia hominis*); kidneyworms (e.g., *Stephanurus dentatus*); screw worm (e.g., *Cochliomyia hominivorax* (larvae); filarial nematodes of the superfamily Filarioidea and the Onchocercidae Family. Non-limiting examples of filarial nematodes within the Onchocercidae Family include the genus *Brugia* spp. (i.e., *B. malayi, B. pahangi, B. timori*, and the like), *Wuchereria* spp. (i.e., *W. bancrofti*, and the like), *Dirofilaria* spp. (*D. immitis, D. repens, D. ursi, D. tenuis, D. spectans, D. lutrae*, and the like), *Dipetalonema* spp. (i.e., *D reconditum, D. repens*, and the like), *Onchocerca* spp. (i.e., *O. gibsoni, O. gutturosa, O. volvulus*, and the like), *Elaeophora* spp. (*E. bohmi, E. elaphi, E. poeli, E. sagitta, E. schneideri*, and the like), *Mansonella* spp. (i.e., *M. ozzardi, M. perstans*, and the like), and *Loa* spp. (i.e., *L. loa*).

Preferably, the compounds of the present invention are used to treat parasitic infection or infestation, preferably wherein the parasite is a flea or tick. In particularly preferred embodiments, the parasite is *C. fells, R. sanguineis, A. americanum, I. scapularis, A. maculate, D. variabilis*, or *I. ricinus*.

In another aspect of the invention, the compound of the present invention is useful for treating endoparasiticidal infection from helminths/filarial nematodes within the genus *Dirofilaria* (i.e., *D. immitis, D. repens, D. ursi, D. tenuis*, and the like).

The compounds of the present invention, stereoisomers thereof, and veterinarily or pharmaceutically acceptable salts thereof, and compositions comprising compounds of the present invention in conjunction with at least one other veterinary agent are of particular value in the control of ectoparasites, endoparasites, and insects which are injurious to, or spread or act as vectors of diseases in companion animals, livestock, birds, and fish.

Any of the compounds of the present invention, or a suitable combination of a compound of the present invention and optionally, with at least one additional veterinary agent may be administered directly to the animal and/or indirectly by applying it to the local environment in which the animal dwells (such as bedding, enclosures, and the like). Direct administration includes contacting the skin, fur, or feathers of a subject animal with the compound(s), or by feeding or injecting the compounds into the animal.

The Formula (I) compound and veterinarily acceptable salt thereof, and combinations with at least one additional veterinary agent, as described herein, are believed to be of value for the treatment and control of the various lifecycle stages of insects and parasites including egg, nymph, larvae, juvenile and adult stages.

The present invention also relates to a method of administering a compound of the present invention alone or in combination with at least one additional veterinary agent, and optionally a veterinarily acceptable excipient, diluent, or carrier, to animals in good health comprising the application to said animal to reduce or eliminate the potential for human parasitic infection or infestation from parasites carried by the animal and to improve the environment in which the animals inhabit.

The present invention explicitly encompasses those compounds presented in Table 1. A composition comprising a therapeutically acceptable amount of any of these compounds is also within the scope of the invention. The composition can further comprise a veterinarily acceptable excipient, diluent, carrier, or mixture thereof. Such a composition can be administered to an animal in need thereof to treat and/or prevent a parasitic infection or infestation. The composition can further comprise an additional veterinary agent, as described herein.

TABLE 1

| Ref. No. | Compound Name |
| --- | --- |
| 1 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one |
| 2 | (S)-6-[5-(3,5-dichloro-4-fluoro-phenyl)-5-(trifluoromethyl)-4H-isothiazol-3-yl]-N-(2,2,2-trifluoroethyl)spiro[1H-isobenzofuran-3,3'-azetidine]-1'-carboxamide |
| 3 | (S)-6-[5-(3,5-dichloro-4-fluoro-phenyl)-5-(trifluoromethyl)-4H-isothiazol-3-yl]-1'-(4-fluorophenyl)sulfonyl-spiro[1H-isobenzofuran-3,3'-azetidine] |
| 4 | (S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-phenyl-methanone |
| 5 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methylsulfonyl-ethanone |
| 6 | (S)-6-[5-(3,5-dichloro-4-fluoro-phenyl)-5-(trifluoromethyl)-4H-isothiazol-3-yl]spiro[1H-isobenzofuran-3,3'-azetidine] |
| 7 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3-dimethyl-butan-1-one |
| 8 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]butan-1-one |
| 9 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-phenyl-ethanone |
| 10 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-4,4,4-trifluoro-butan-1-one |
| 11 | (S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-(1-naphthyl)methanone |

TABLE 1-continued

| Ref. No. | Compound Name |
|---|---|
| 12 | (S)-[(3Z,4Z)-4-allylidene-3-ethylidene-cyclohexa-1,5-dien-1-yl]-[6-[5-(3,5-dichloro-4-fluoro-phenyl)-5-(trifluoromethyl)-4H-isothiazol-3-yl]spiro[1H-isobenzofuran-3,3'-azetidine]-1'-yl]methanone |
| 13 | (S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-(4-morpholinophenyl)methanone |
| 14 | (S)-6-[5-(3,5-dichloro-4-fluoro-phenyl)-5-(trifluoromethyl)-4H-isothiazol-3-yl]-1'-propylsulfonyl-spiro[1H-isobenzofuran-3,3'-azetidine] |
| 15 | (S)-6-[5-(3,5-dichloro-4-fluoro-phenyl)-5-(trifluoromethyl)-4H-isothiazol-3-yl]-1'-(3,3,3-trifluoropropylsulfonyl)spiro[1H-isobenzofuran-3,3'-azetidine] |
| 16 | (S)-6-[5-(3,5-dichloro-4-fluoro-phenyl)-5-(trifluoromethyl)-4H-isothiazol-3-yl]-N-ethyl-spiro[1H-isobenzofuran-3,3'-azetidine]-1'-carboxamide |
| 17 | (S)-6-[5-(3,5-dichloro-4-fluoro-phenyl)-5-(trifluoromethyl)-4H-isothiazol-3-yl]-N-phenyl-spiro[1H-isobenzofuran-3,3'-azetidine]-1'-carboxamide |
| 18 | (S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-[3-(2,2-dichlorovinyl)-2,2-dimethyl-cyclopropyl]methanone |
| 19 | (S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-tetrahydropyran-4-yl-methanone |
| 20 | (S)-1'-butyl-6-[5-(3,5-dichloro-4-fluoro-phenyl)-5-(trifluoromethyl)-4H-isothiazol-3-yl]spiro[1H-isobenzofuran-3,3'-azetidine] |
| 21 | (S)-6-[5-(3,5-dichloro-4-fluoro-phenyl)-5-(trifluoromethyl)-4H-isothiazol-3-yl]-1'-(3,3-dimethylbutyl)spiro[1H-isobenzofuran-3,3'-azetidine] |
| 22 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methoxy-ethanone |
| 23 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-isopropoxy-ethanone |
| 24 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-ethoxy-ethanone |
| 25 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methyl-propan-1-one |
| 26 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]propan-1-one |
| 27 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]ethanone |
| 28 | (S)-3-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-4-ethoxy-cyclobut-3-ene-1,2-dione |
| 29 | (S)-3-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3-oxo-propanenitrile |
| 30 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2,2,3,3,3-pentafluoro-propan-1-one |
| 31 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2,2-difluoro-propan-1-one |
| 32 | (S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-[1-(trifluoromethyl)cyclopropyl]methanone |
| 33 | (S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-[1-(trifluoromethyl)cyclobutyl]methanone |
| 34 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-2,2-dimethyl-propan-1-one |
| 35 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]pentan-1-one |
| 36 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]hexan-1-one |
| 37 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]heptan-1-one |
| 38 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]octan-1-one |
| 39 | (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]nonan-1-one |
| 40 | (S)-6-[5-(3,5-dichloro-4-fluoro-phenyl)-5-(trifluoromethyl)-4H-isothiazol-3-yl]-1'-pyrimidin-2-yl-spiro[1H-isobenzofuran-3,3'-azetidine] |
| 41 | (S)-6-[5-(3,5-dichloro-4-fluoro-phenyl)-5-(trifluoromethyl)-4H-isothiazol-3-yl]-N-methyl-spiro[1H-isobenzofuran-3,3'-azetidine]-1'-carboxamide |

EXAMPLES

The following Examples provide a more detailed description of the process conditions for preparing compounds of the present invention. It is to be understood, however, that the invention, as fully described herein and as recited in the claims, is not intended to be limited by the details of the following schemes or modes of preparation.

Example 1

Synthesis of (S)-1-(5'-(5-(3,5-dichloro-4-fluorophenyl)-5-(trifluoromethyl)-4,5-dihydroisothiazol-3-yl)-3'H-spiro[azetidine-3,1'-isobenzofuran]-1-yl)-3,3,3-trifluoropropan-1-one

Intermediate 1

(Z)-3-(3,5-dichloro-4-fluorophenyl)-4,4,4-trifluoro-1-(1-(3,3,3-trifluoropropanoyl)-3'H-spiro[azetidine-3,1'-isobenzofuran]-5'-yl)but-2-en-1-one (10)

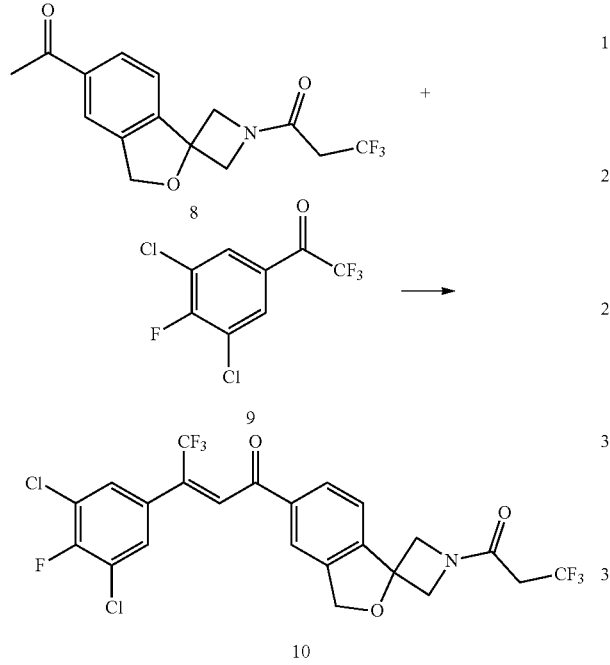

1-(5'-acetyl-3'H-spiro[azetidine-3,1'-isobenzofuran]-1-yl)-3,3,3-trifluoropropan-1-one (2.16 kg) and 1-(3,5-dichloro-4-fluorophenyl)-2,2,2-trifluoroethan-1-one 9 (3.22 kg) were dissolved in 12 L THF. Triethylamine (1.95 L) was added and the mixture was warmed to 60° C. over two hours and held at 60° C. for 4 hours at which time the reaction was complete by HPLC. Azeotropic removal of water at atmospheric pressure was conducted, with addition of fresh THF to keep the volume constant, until water content was <0.13% by Karl Fischer analysis. The mixture was then cooled to 20° C., and triethylamine (680 mL) and DMAP (128 g) were added, followed by acetic anhydride (1.33 L) at a rate such that the temperature did not exceed 25° C. After stirring for 7 hours, the reaction was complete by HPLC analysis, and ammonium chloride (20% solution in water, 6.6 L) was added followed by MTBE (11 L). After stirring for 15 minutes, the phases were allowed to split, and the aqueous layer was discarded. The organic layer was washed with 4.4 L of a 0.1 N NaOH solution followed by 4.4 L of a 27 wt % solution of NaCl. The organic layer was concentrated under vacuum, and a solvent swap to IPA was conducted to a final volume of 35 L. The mixture was heated to 67° C. until all material dissolved, and then water (14.3 L) was added over 1.5 hours, the mixture cooled to 58° C., and seed crystals (44 g) added. After holding the mixture at 55° C. for 90 minutes, the mixture was cooled to between 40° C. and 45° C. and water added (3.3 L) over 15 minutes, at which time the temperature was raised to 55° C. and held 16 h with stirring. The crystallization was then cooled to 40° C. and water was added (3.3 L) over 15 min, after which the mixture was heated to 55° C. and held for 15 minutes, and then cooled to 20° C. over 3 hours. The mixture was stirred at 20° C. for 2 hours, and then filtered, the solids washed with 5.5 L of a 6:5 IPA:water solution, and the solids collected and dried under vacuum to give 2.75 kg of product (Z)-3-(3,5-dichloro-4-fluorophenyl)-4,4,4-trifluoro-1-(1-(3,3,3-trifluoropropanoyl)-3'H-spiro[azetidine-3,1'-isobenzofuran]-5'-yl)but-2-en-1-one (10) (70% yield). 1H NMR (400 MHz, CHLOROFORM-d) δ=7.88 (dd, J=0.6, 8.0 Hz, 1H), 7.72 (s, 1H), 7.53 (d, J=8.0 Hz, 1H), 7.41 (d, J=1.2 Hz, 1H), 7.24 (d, J=6.1 Hz, 2H), 5.18 (s, 2H), 4.61 (d, J=9.1 Hz, 1H), 4.48-4.39 (m, 2H), 4.35-4.30 (m, 1H), 3.14-3.02 (m, 2H).

Intermediate 2

(S)-3-(3,5-dichloro-4-fluorophenyl)-4,4,4-trifluoro-3-((4-methoxybenzyl)thio)-1-(1-(3,3,3-trifluoropropanoyl)-3'H-spiro[azetidine-3,1'-isobenzofuran]-5'-yl)butan-1-one (11)

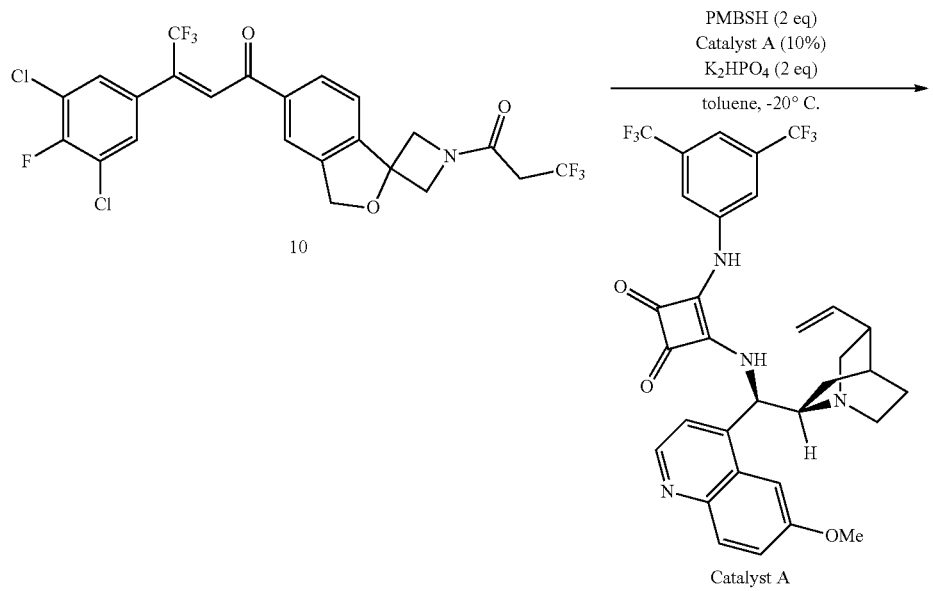

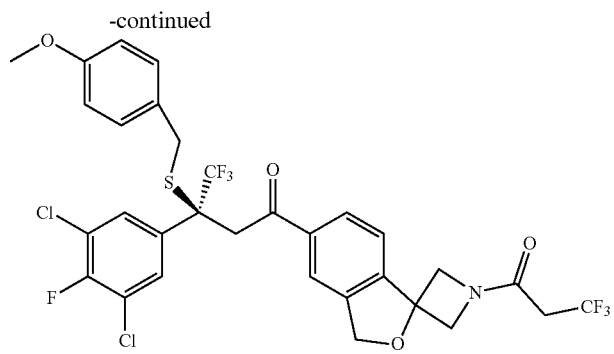

11

(Z)-3-(3,5-dichloro-4-fluorophenyl)-4,4,4-trifluoro-1-(1-(3,3,3-trifluoropropanoyl)-3'H-spiro[azetidine-3,1'-isobenzofuran]-5'-yl)but-2-en-1-one (10), Catalyst A (3-((3,5-bis(trifluoromethyl)phenyl)amino)-4-(((R)-(6-methoxyquinolin-4-yl)((1S,2R,4S,5R)-5-vinylquinuclidin-2-yl)methyl)amino)cyclobut-3-ene-1,2-dione), and $K_2HPO_4$ were slurried in 16 L of toluene, and cooled to −20° C. To this mixture was added a solution of PMBSH (1.18 kg) in 2.35 L toluene over 40 hours. After 48 hours the reaction was complete by HPLC (1% 10 remaining) at which time a solution of 327 g of $K_2HPO_4$ in water was added followed by 4.6 L EtOAc, and the reaction allowed to warm to 20° C. The aqueous layer was removed, and a 1 M solution of sulfuric acid in water was added at such a rate as to keep the reaction temperature <25° C. The resulting slurry was filtered and the solids washed with 2 L EtOAc and discarded. The aqueous layer of the filtrates was removed and the organic layer was washed once with 4.6 L of 1 M $H_2SO_4$ and once with 6 L of 26% brine solution. The solvent was removed and the residue suspended on 3.5 kg silica gel. Column chromatography (4.6 kg silica, heptane/EtOAc) to remove residual PMBSH was followed by HPLC, and the fractions containing product were combined and the solvent removed to give 2.7 kg of product (S)-3-(3,5-dichloro-4-fluorophenyl)-4,4,4-trifluoro-3-((4-methoxybenzyl)thio)-1-(1-(3,3,3-trifluoropropanoyl)-3'H-spiro[azetidine-3,1'-isobenzofuran]-5'-yl)butan-1 -one (11) (92% yield). 1H NMR (400 MHz, CHLOROFORM-d) δ=7.84 (t, J=6.8 Hz, 1H), 7.66 (s, 1H), 7.58 (d, J=6.0 Hz, 2H), 7.48 (dd, J=1.9, 8.0 Hz, 1H), 7.10 (d, J=8.7 Hz, 2H), 6.76 (d, J=8.6 Hz, 2H), 5.17 (s, 2H), 4.61 (d, J=8.9 Hz, 1H), 4.49-4.39 (m, 2H), 4.37-4.30 (m, 1H), 3.94-3.88 (m, 1H), 3.85 (d, J=12.0 Hz, 1H), 3.79-3.70 (m, 4H), 3.65 (d, J=12.0 Hz, 1H), 3.08 (dq, J=2.5, 10.3 Hz, 2H).

Intermediate 3

To a $N_2$ flushed 12 L reactor with jacket temperature ($T_J$) set to −2.5° C. was added 1 L of DCM followed by 455.0 g (0.6404 mol) of intermediate 11 and the reactor rinsed with 2.4 L of DCM while stirring at 200 rpm. An addition funnel was charged with 85 mL (0.963 mol) TfOH and placed atop the reactor. When the reaction temperature ($T_R$) reached 0° C., addition of TfOH occurred over 10 minutes while keeping $T_R$<5° C. The maximum $T_R$=2.1° C. and then $T_J$ was set to 0° . After 1 hour, $T_J$ was set to 18° C. and the reaction monitored by HPLC. After an additional 4 hours, HPLC analysis showed no change in the ~6.5% remaining starting material. To the solution was added 570 mL of potassium phosphate buffer (buffer made by diluting 445 g $K_2HPO_4$ and 230 g $KH_2PO_4$ to 4 L with $H_2O$). An exotherm was observed from $T_R$=18.7° C. with maximum $T_R$=21.3° C. After 15 minutes stirring was stopped and a good phase split formed within 5 minutes. 3.5 L organic was collected and the aqueous was discarded. An additional 570 mL potassium phosphate buffer was added to the reactor followed by the organic layer and the solution stirred at 200 rpm for 15 minutes. A good phase split formed within 5 minutes of ending the stirring and the organic was collected and the aqueous discarded. 225 mL $H_2O$ was added to the reactor followed by the organic layer and the solution stirred at 200 rpm for 15 minutes. A good phase split formed within 5 minutes of ending the stirring and the organic was collected and the aqueous discarded. The organic layer was transferred to a 5 L round bottom flask and DCM distilled using a rotary evaporator with the bath set to 30° C. When the solution was ~1 L, 1 L of EtOH was added and distillation continued. A tan/white foamy precipitate formed with the addition of EtOH that broke up to a free flowing precipitate with continued stirring. After 30 minutes an additional 1.5 L EtOH was added and the solution stirred without vacuum and with the water bath turned off. NMR showed 2 mol% DCM referenced to EtOH. After stirring for 1 hour, the solution was filtered through a 24 cm non-shedding filter paper on a tabletop filter and the solids rinsed with 0.5 L EtOH. After sitting 14 hours, a polish filtration removed residual solids and the EtOH was distilled using a rotary evaporator. When the solution was ~1 L, 500 mL of THF was added and the solution was concentrated to dryness. After drying under reduced pressure at ambient temperature for 42 hours, 375.9 g of (S)-3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5'-yl)butan-1 -one, intermediate 12, was collected as a tan foam in 99% yield.

Compound C1: A 1 L Erlenmeyer flask with magnetic stir bar was charged with 160.6 g (1.420 mol) hydroxylamine-O-sulfonic acid (HOSA) and 500 mL MeOH and the resulting slurry stirred on a stir plate. To a $N_2$ flushed 12 L reactor was added 140 mL THF followed by 280.1 g (0.47448 mol) of (S)-3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5'-yl)butan-1-one, intermediate 12, in 300 mL of THF. Overhead stirring was set to 60 rpm and an additional 200 mL THF ×2 (3 total volumes of THF) used to transfer the residual intermediate 12 and rinse down the walls of the reactor. $T_J$ was set to 13.6° C. The solution of HOSA in MeOH was added to the solution of intermediate 12 and the Erlenmeyer flask rinsed with an additional 170 mL MeOH ×2 (3 total volumes of MeOH) and this was added to the reactor. Stirring was set to 180 rpm. With $T_R$=14.1° C., $T_J$ was set to 9° C. To the cooling solution was added 168 mL (1.45 mol) 2,6-lutidine over 6 minutes in ~20 mL portions. $T_{R(Max)}$ was 16.4° C. and $T_J$ was set to 13.7° C. following the addition. The reaction was monitored by HPLC to determine end of reaction with consumption of 12. A 2 L graduated cylinder was used to make 1.8 L of 1 M HCl (aq) by adding 155 mL of concentrated HCl to 1.6 L DI water and diluting to 1.8 L with DI water. After 18 hours, HPLC indicated the end of reaction and 1 L tert-butyl methyl ether was added followed by 840 mL of 1 M HCl (aq). After stirring for 20 minutes, the layers were separated and 1.82 L of pH 1 aqueous was discarded. An additional 840 mL of 1 M HCl (aq) was added and stirring was continued for 10 minutes. After the layers separated, 1.48 L of aqueous was collected and discarded. The remaining ~100 mL of 1 M HCl (aq) was diluted to 1 L with DI water. This 0.1 M HCl (aq) solution was added to the organic and the solution stirred for 15 minutes. After 10 minutes, 1.5 L of aqueous was collected and discarded and the organic was polish filtered through a 30 μm Meissner filter (CS2MF30-442) and the filter washed with two portions of MTBE to give an organic volume of 1.6 L (a total of ~500 mL MTBE was used in transfers and washings). The organic was transferred to a 2 L flask and MTBE distilled using a rotary evaporator. When the volume was ~500 mL, 560 mL of EtOH was added and distillation continued, using NMR to monitor solvent levels. At end of distillation, NMR indicated 0.1 mol % MTBE compared to APS-488. The solution was transferred to a 1 L jacketed 3 neck reactor set to 36° C. with overhead stirring, internal thermocouple, and a $N_2$ inlet. An additional 180 mL EtOH was used in 60 mL portions to transfer the solution and to achieve 1800 mol % EtOH by NMR. To the homogenous yellow/orange solution at $T_R$=34.7° C. was added 2.34 g of seed as a slurry in 10 mL EtOH. After stirring for 22 hours, the tan slurry was cooled to 0° C. over 63 hours. After stirring at 0° C. for 5 hours, the slurry was filtered on a 90 mm Buchner funnel using non-shedding filter paper and the cake was washed with 250 mL of chilled EtOH to give 93 g of a tan powder that was 2.4 cm in height. The tan powder was transferred to a crystallization dish and vacuum dried at 50° C. for 21 hours, resulting in 89.91 g of (S)-1-[6-[5-(3,5-dichloro-4-fluoro10phenyl)-5-(trifluoromethyl)-4H-isothiazol-3-yl]spiro[1H-isobenzofuran-3,3'-azetidine]-1'-yl]-3,3,3-trifluoro-propan-1-one (C1 (S) enantiomer) isolated in 31% yield. $^1$H NMR (400 MHz, CDCl$_3$) δ=7.77 (br d, J=6.8 Hz, 1H), 7.68 (br s, 1H), 7.47 (d, J=8.0 Hz, 1H), 7.38 (d, J=5.9 Hz, 2H), 5.17 (s, 2H), 4.59 (br d, J=9.2 Hz, 1H), 4.48-4.37 (m, 2H), 4.37-4.29 (m, 1H), 4.22 (d, J=17.6 Hz, 1H), 3.88 (d, J=17.6 Hz, 1H), 3.07 (dq, J=2.3, 10.3 Hz, 2H).

Representative Chromatogram of (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one C1 (S) enantiomer and its (R) enantiomer (R)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one by Chiral HPLC is shown in FIG. 1.

Compounds 2-41 shown in Table 1 can be prepared as described in WO 2016115315 and purified using chiral separation methodology as would be understood by a person having ordinary skill in the art.

Example 2

Crystal structure of (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one (C1 (S) enantiomer)

Figure 2:
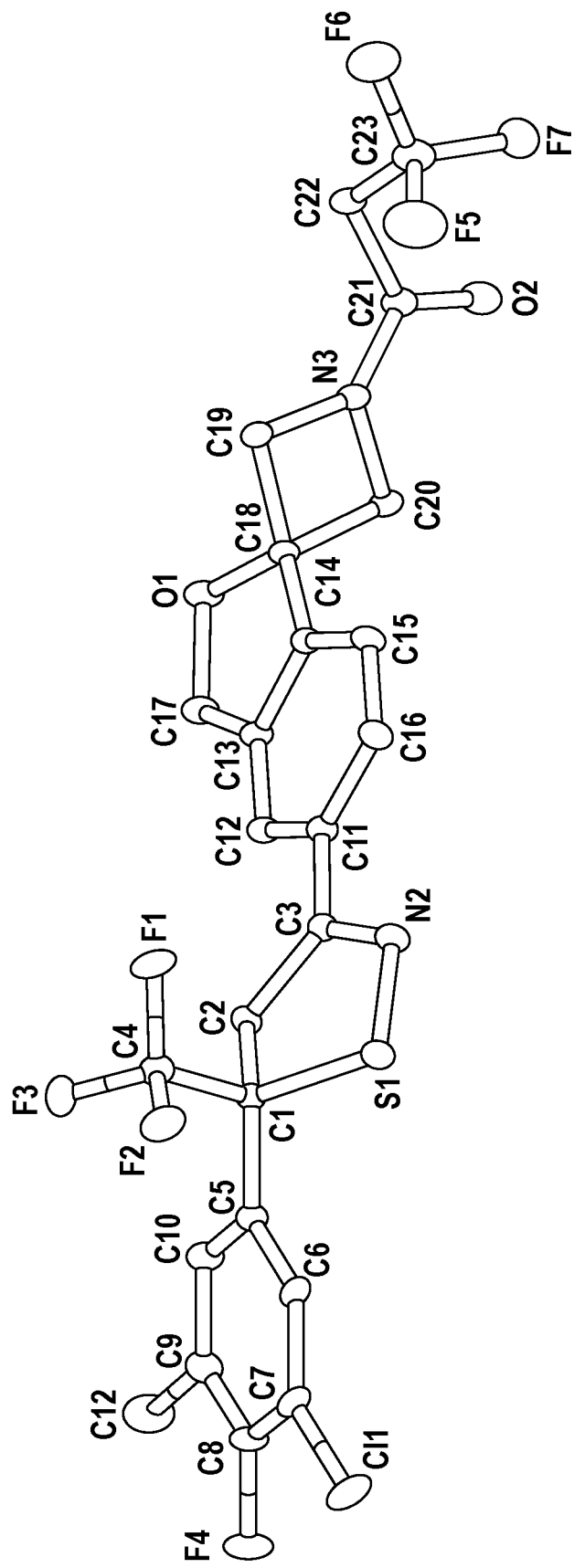
FIG. 2: Thermal ellipsoid plot (50% probability) of C1 (S) enantiomer with hydrogen atoms hidden for clarity.

Compound C1 (S) enantiomer crystallizes in the monoclinic space group $P2_1$. The thermal ellipsoid plot (50% probability) of C1 (S) enantiomer is shown in FIG. 2 The unit cell contains two molecules. The stereochemistry at atom C1 is S. The statistical determination of this value can, and should, be confirmed through chemical means as part of a complete analysis. The bond pattern in the ring containing S1 appears to be unique, with no similar structures evident in the Cambridge Structural Database (version 5.38, updated May 2017). A Mogul geometry check revealed a few statistically unusual geometric features (bond lengths, bond angles, torsion angles, etc.) which are likely associated with the rarity of the ring system in the database. There is no evidence for hydrogen bond interactions between molecular units of this compound.

Experimental Procedure:

A colorless block-like specimen of C1 (S) enantiomer with approximate dimensions of 0.122 mm×0.174 mm×0.241 mm, was used for the X-ray crystallographic analysis. The X-ray intensity data were measured using a Bruker-Nonius X8 APEX II diffractometer.

The total exposure time was 16.81 hours. The frames were integrated with the Bruker SAINT software package using a narrow-frame algorithm. The integration of the data using a monoclinic unit cell yielded a total of 41804 reflections to a maximum θ angle of 36.37° (0.60 Å resolution), of which 11540 were independent (average redundancy 3.623, completeness=99.2%, $R_{int}$=3.06%, $R_{sig}$=3.40%) and 10085 (87.39%) were greater than 2σ($F^2$). The final cell constants of a=9.918(4)Å, b=10.241(4)Å, c=12.055(4)Å, β=101.891(8)°, volume=1198.2(7)Å$^3$, are based upon the refinement of the XYZ-centroids of 348 reflections above 20 σ(I) with 5.794°<2θ<63.48°. Data were corrected for absorption effects using the Multi-Scan method (SADABS, Bruker, Madison, Wis., 2016). The ratio of minimum to maximum apparent transmission was 0.932. The calculated minimum and maximum transmission coefficients (based on crystal size) are 0.9020 and 0.9480. Structure solution was accomplished using direct methods as implemented by XS (Bruker, Madison, Wis., 2014)

The final anisotropic full-matrix least-squares refinement on $F^2$ with 334 variables converged at R1=3.66%, for the observed data and wR2=8.69% for all data. The goodness-of-fit was 1.033. The largest peak in the final difference electron density synthesis was 0.461 e$^-$/Å$^3$ and the largest hole was −0.274 e$^-$/Å$^3$ with an RMS deviation of 0.067 e$^-$/Å$^3$. On the basis of the final model, the calculated density was 1.628 g/cm$^3$ and F(000), 592 e$^-$. The final refined value for the absolute structure factor (Flack) was determined using 4214 quotients [(I+)−(I−)]/[(I+)+(I−)] according to methods of Parsons, Flack and Wagner (Act Cryst. B69 (2013) 249-259) with a value of 0.048(12), sufficient to declare that the structure depicted is the correct hand.

Example 3

Pharmacokinetics of (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one (C1 (S) enantiomer).

Summary

This study assessed the in vivo pharmacokinetic (PK) behavior of a single oral dose of the C1 (S) enantiomer in beagle dogs (Charles River study# 20104466). Solutions of C1 (S) enantiomer were dosed by oral gavage (10mg/kg) to a group of dogs (n=3). Blood samples were collected pre-dose and at 0.25, 0.5, 1, 2, 4, and 8 hours following dosing on Day 1. Blood samples were also collected on Days1, 2, 3, 5, 7, 10, 14, 17, 21, 25, 28, 32, 35, 39, 43, and 45. A portion of each whole blood sample was processed to plasma. Test article concentrations in plasma and whole blood were determined using liquid chromatography tandem mass spectrometry (LC-MS/MS).

The average maximum observed concentrations in plasma and blood ($C_{max}$) of C1 (S) enantiomer were 2.26 and 3.65 μg/mL, respectively. Area under the curve extrapolated to infinity ($AUC_{0-\infty}$) for plasma and blood were 196 and 148 hr*μg/mL, respectively. $T_{max}$ (the amount of time that a drug is present at the maximum concentration) in plasma and blood were 2.0 and 1.7 hr, respectively. The elimination half-life ($t_{1/2}$) in plasma and blood were 205 and 209 hr, respectively.

It was confirmed that racemic 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one is a well-absorbed compound with an extended elimination half-life in dogs. However, the S-enantiomer plasma PK curves and calculated PK parameters conducted in beagle dogs differed from oral efficacy studies conducted on the racemate dosed in mongrels. Specifically, the average half-life of C1 (S) enantiomer was shorter than that of the racemate. Additionally, the $C_{max}$ and AUC of C1 (S) enantiomer were lower compared to those of the racemate at the same dose level.

Figure 3:
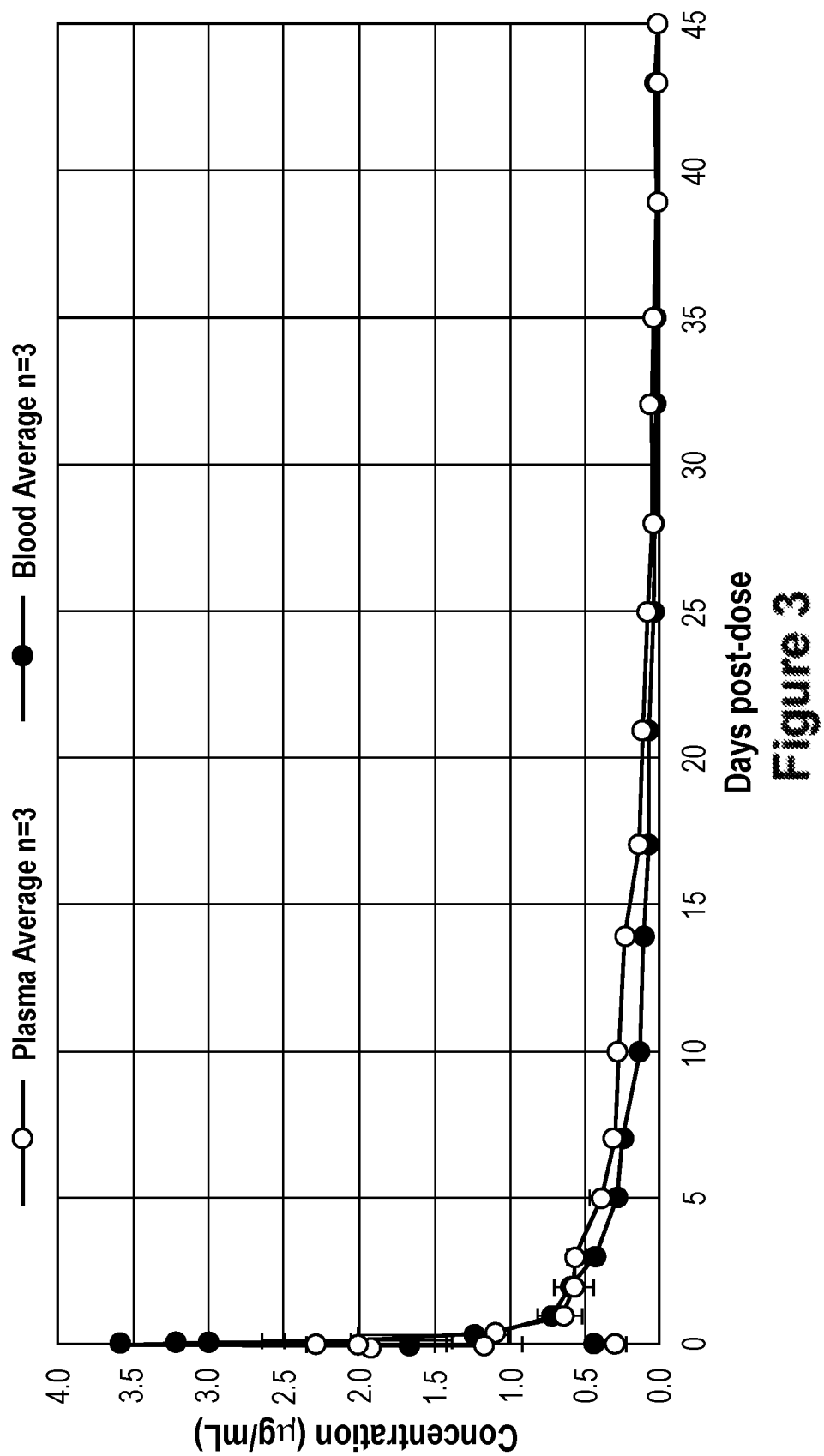
FIG. 3. Average plasma and whole blood pharmacokinetic (PK) profile for the C1 (S) enantiomer in a dog PK study (plasma vs. whole blood). Lines are drawn between data points for clarity and are not the results of any data fitting.
Figure 4:
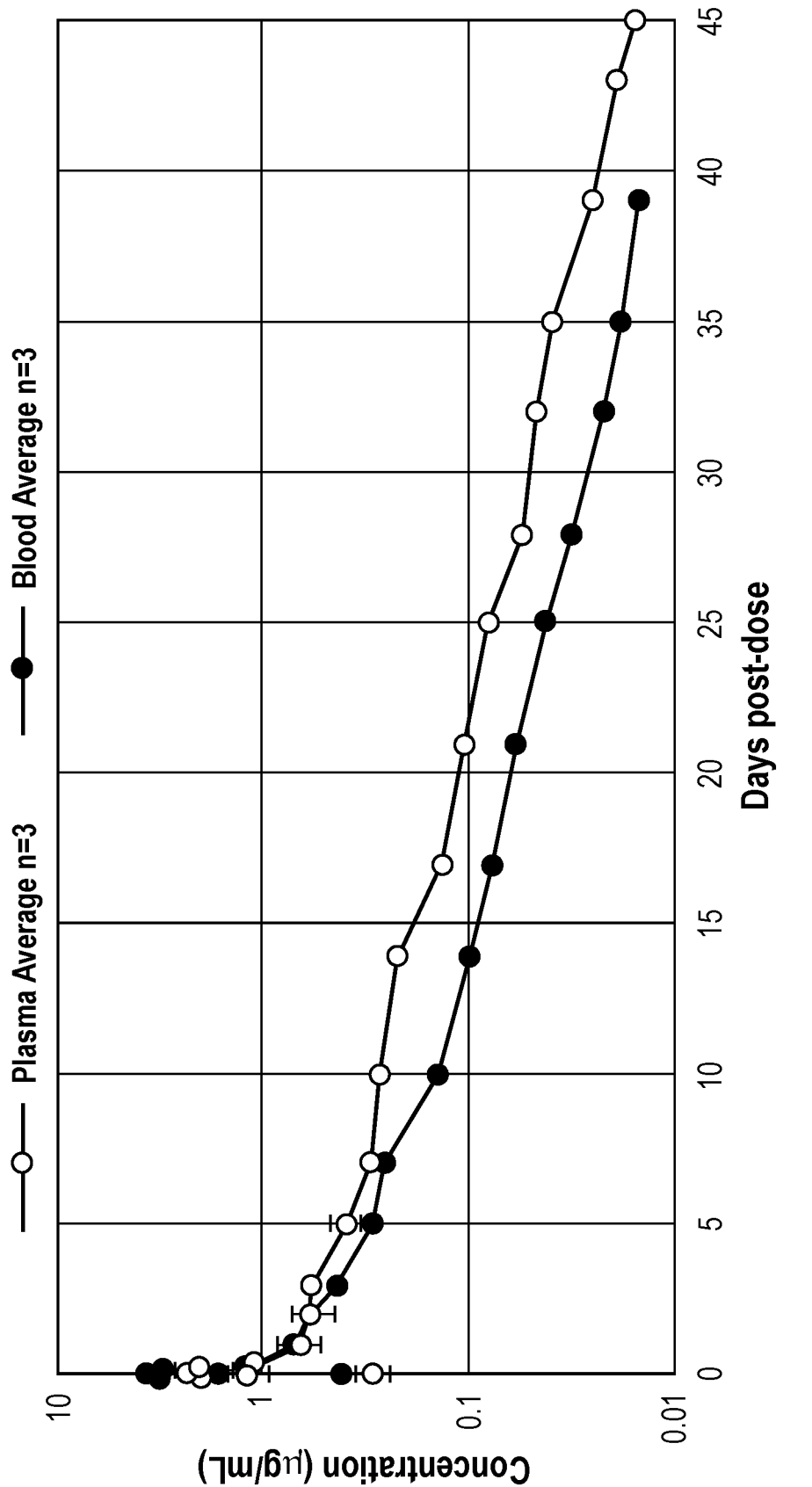
FIG. 4. Semi log plot of average plasma and whole blood PK profile for the C1 (S) enantiomer dog PK study (plasma vs. whole blood).

There was no bioconversion observed during the study; results are shown in FIGS. 3-4.

Materials and Methods

Bioanalysis

Calibration curves were constructed by spiking racemic 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one into aliquots of blank K2EDTA beagle plasma or whole blood (Bioreclamation, Westbury, N.Y.) at the following nominal concentrations: 5, 10, 20, 50, 100, 200, 500, 1000, 2000, 5000, and 10000 ng/mL. Quality control samples (QCs) were prepared in the same manner at the following concentrations: 15, 30, 150, 800, 1600, 4000, and 8000 ng/mL.

Samples (double blanks, blank+IS, blank+drug, standards, QC samples, and study samples) were extracted using a protein precipitation procedure. A 50 μL aliquot of plasma or blood was transferred into a deep well 96-well plate. To the sample aliquot, 250 μL of an internal standard (IS) solution for plasma or 300 μL for blood was added. The internal standard solution contained Afoxolaner at 50 ng/mL in methanol. For double blanks and blank+drug, neat methanol instead of IS was added. The 96-well plate was capped, shaken for ten minutes, and centrifuged at 5000 relative centrifugal force (RCF) for 10 minutes at 15° C. A 150-200 μL aliquot of the resulting supernatant of each sample was transferred to a clean, 96-well microtiter plate. The microtiter plate was capped and subjected to LC-MS/MS analysis.

The LC-MS/MS system consisted of a Leap autosampler, an Agilent 1100 series liquid chromatography pump, and a SciexAPI4000 mass spectrometer operated in triple quadrupole mode. A ChiralPak IA column (4.6×150mm, 5μm particle, Supplier Daicel PN 80324)at room temperature was used with water as mobile phase A and neat acetonitrile as mobile phase B. The LC gradient, MS parameters, and gas parameters are shown in the tables 2-4, respectively.

TABLE 2

LC gradient

| Step | Total Time(min) | Flow Rate(μl/min) | A (%) | B (%) |
|---|---|---|---|---|
| 0 | 0 | 1000 | 30 | 70 |
| 1 | 10 | 1000 | 30 | 70 |

The mass spectrometer (MS) was operated in negative Turbo IonSpray™ mode with Multiple Reaction Monitoring (MRM).

TABLE 3

MS parameters

| Compound ID | Polarity | Precursor ION | Product ION | Dwell (ms) | DP | EP | CE | CXP |
|---|---|---|---|---|---|---|---|---|
| 344 | NEG | 585 | 515.1 | 200 | −120 | −10 | −26 | −13 |
| 6524 (Afoxolaner) | NEG | 624.2 | 604.2 | 200 | −120 | −10 | −30 | −13 |

TABLE 4

Gas parameters

| CAD | 12 |
|---|---|
| CUR | 20 |
| GS1 | 50 |
| GS2 | 50 |
| IS | −4500 |
| TEM | 550 |
| ihe | on |

Following LC-MS/MS analysis, peak area ratios were calculated (analyte peak area divided by internal standard peak area). Standard curves were created by generating least squares fitting plots of peak area ratio versus nominal concentration. Sample concentrations were calculated from the results of the least squares fits.

Pharmacokinetic Analysis $C_{max}$ and $T_{max}$ are the observed maximum drug concentration and the time at which the maximum concentration occurs, respectively. Area under the curve (AUC) was calculated using the linear trapezoid method. To calculate half-lives ($t_{1/2}$), a least squares regression was performed on a log concentration (C) versus time (t) plot (semi-log plot) to obtain the slope, k. The $t_{1/2}$ is equal to 0.693/k. The $t_{1/2}$ was calculated using data points in the elimination phase. For oral PK, Cl/F=Dose/AUC.

Results

In this report, PK calculations were normalized to the measured dose solution concentrations. Note that in all figures and tables below, the nominal dose is listed.

Table 5 and FIGS. 3-4 show the average drug concentrations obtained from the study samples.

TABLE 5

Average Compound C1 (S) Enantiomer Concentrations in Plasma and Blood (μg/mL)

| Time (hr) | Plasma Concentration (μg/ml) | Blood Concentration (μg/ml) |
|---|---|---|
| Pre-dose | BQL [a] | BQL [b] |
| 0.25 | 0.291 ± 0.057 | 0.412 ± 0.089 |
| 0.5 | 1.17 ± 0.25 | 1.66 ± 0.38 |
| 1 | 1.92 ± 0.33 | 3.21 ± 0.23 |
| 2 | 2.26 ± 0.17 | 3.56 ± 0.57 |
| 4 | 2.01 ± 0.36 | 2.99 ± 0.34 |
| 8 | 1.11 ± 0.07 | 1.22 ± 0.17 |
| 24 | 0.664 ± 0.112 | 0.708 ± 0.162 |
| 48 | 0.567 ± 0.095 | 0.572 ± 0.128 |
| 72 | 0.552 ± 0.065 | 0.428 ± 0.071 |
| 120 | 0.393 ± 0.067 | 0.292 ± 0.056 |
| 168 | 0.298 ± 0.039 | 0.245 ± 0.047 |
| 240 | 0.270 ± 0.019 | 0.136 ± 0.02 |
| 336 | 0.219 ± 0.024 | 0.100 ± 0.006 |
| 408 | 0.135 ± 0.012 | 0.0758 ± 0.0112 |
| 504 | 0.103 ± 0.015 | 0.0573 ± 0.0085 |
| 600 | 0.0804 ± 0.0113 | 0.0412 ± 0.0037 |
| 672 | 0.0556 ± 0.0122 | 0.0305 ± 0.0051 |
| 768 | 0.047 ± 0.0119 | 0.0215 ± 0.0042 |
| 840 | 0.0374 ± 0.0082 | 0.0174 ± 0.0048 |
| 936 | 0.0248 ± 0.0064 | 0.0143 ± 0.0034 |
| 1032 | 0.0188 ± 0.0055 | 0.0138 ± 0 [b†] |
| 1080 | 0.0157 ± 0.0063 | BQL [b] |

Discussion

Pharmacokinetic results from the compound C1 (S) enantiomer PK study differed from racemic efficacy studies. Average plasma pharmacokinetic parameters from the compound C1 (S) enantiomer PK study described in this document are compared to those from oral efficacy studies of the racemate in Table 6.

TABLE 6

Average Plasma PK Parameters from Compound C1 (S) enantiomer PK vs. C1 Racemate Efficacy Studies

| | C1 (S) enant. PK (10 mg/kg) | Racemate Tick Efficacy (10 mg/kg)[†] | Racemate Tick Efficacy (20 mg/kg)[†] | Racemate Flea Efficacy (10 mg/kg)[†] | Racemate Flea Efficacy (20 mg/kg)[†] |
|---|---|---|---|---|---|
| Dog Strain | Beagle | Mongrel | Mongrel | Mongrel | Mongrel |
| $t_{last}$ (hr) | 1080 | 1056 | 1056 | 1032 | 1032 |
| NCA AUC$_{0\text{-}last}$ (hr*μg/mL) | 191 | 344 | 494 | 266 | 463 |
| NCA AUC$_{0\text{-}\infty}$ (hr*μg/mL) | 196 | 395 | 674 | 361 | 525 |
| Cl/F (L/kg/hr) | 0.050 | 0.0301 | 0.0416 | 0.0386 | 0.0442 |
| $t_{1/2}$ (hr) | 205 | 393 | 570 | 572 | 357 |
| $C_{max}$ (μg/ml) | 2.26 | 3.78 | 6.24 | 3.47 | 4.74 |
| $T_{max}$ (hr) | 2.0 | 3.0 | 2.0 | 1.0 | 1.0 |

The plasma $T_{max}$ of compound C1 (S) enantiomer was similar to that of the racemate in the racemic studies, however, the plasma $C_{max}$ of C1 (S) enantiomer was lower than that of the racemate (2.26 μg/ml vs. 3.47-3.78 μg/ml) when either C1 (S) enantiomer or the C1 racemate was dosed at 10 mg/kg). Additionally, C1 (S) enantiomer was cleared faster from plasma than the racemate, demonstrated by Cl/F (0.050 L/kg/hr vs. 0.030-0.044 L/kg/hr) and half-life (205 hr vs. 357-572 hr). Therefore, the plasma area under the curve extrapolated to infinity (AUC$_{0\text{-}\infty}$) of C1 (S) enantiomer was expected to be lower than that of the racemate (196 vs. 361-395 hr*μg/mL at 10 mg/kg).

Pharmacokinetic parameters of plasma and whole blood from the C1 (S) enantiomer PK study are compared in Table 7. It should be noted that the blood concentrations of C1 (S) enantiomer was significantly higher than the corresponding plasma concentrations in the first a few hours post-dose, which causes higher $C_{max}$ in the blood than the plasma. Additionally, the concentration in blood reached the $C_{max}$ sooner than in the plasma. These facts indicated that the compound has a higher initial affinity to red blood cells (RBC). After that, the blood:plasma concentration ratio kept decreasing, and at 48 hours, the concentrations in blood and plasma were similar, indicating similar concentration in plasma and RBC. After 240 hours, the concentration in plasma was about twice the blood concentration, indicating the compound was almost all in plasma, not RBC.

TABLE 7

PK Parameters of Plasma and Whole Blood from C1 (S) enantiomer PK Study

| Time | Plasma Parameters | Whole Blood Parameters |
|---|---|---|
| Nominal Dose (mg/kg) | 10 | 10 |
| Actual Dose (mg/kg) | 9.59 | 9.59 |
| NCA AUC$_{0\text{-}last}$ (hr*μg/mL) | 191 ± 11 | 144 ± 11 |
| NCA AUC$_{0\text{-}\infty}$ (hr*μg/mL) | 196 ± 11 | 148 ± 10 |
| Cl/F (L/kg/hr) | 0.0504 ± 0.0028 | 0.0670 ± 0.005 |
| $t_{1/2}$ (hr) | 205 ± 30 | 209 ± 32 |
| $C_{max}$ (μg/ml) | 2.26 ± 0.17 | 3.65 ± 0.42 |
| $T_{max}$ (hr) | 2.00 ± 0 | 1.67 ± 0.58 |

The AUC of blood is lower than the plasma, and that is due to lower concentration in blood at later time points, despite the initial higher concentration in blood. This also caused the faster clearance (Cl/F) shown in blood. On the other hand, half-life is calculated solely on the later time points (after 240 hours), therefore, the blood half-life is very similar to the plasma.

Figure 5:
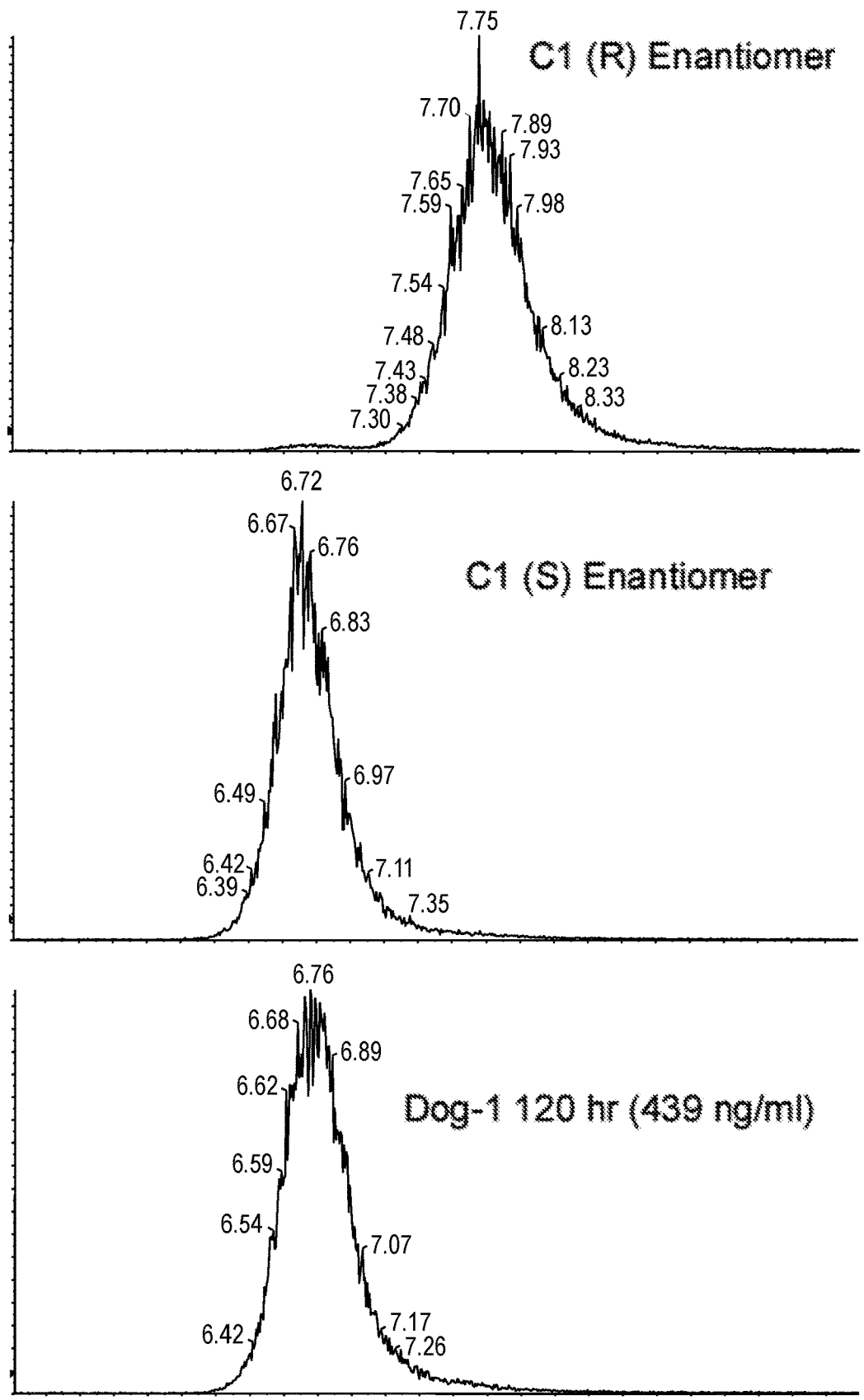
FIG. 5. Representative chromatogram of C1 (R) enantiomer and C1 (S) enantiomer by chiral HPLC. By comparing 120 hr dog plasma sample for dog-1 and a standard of similar concentration, there is no conceivable increase in the C1 (R) enantiomer content in vivo.
Figure 7:
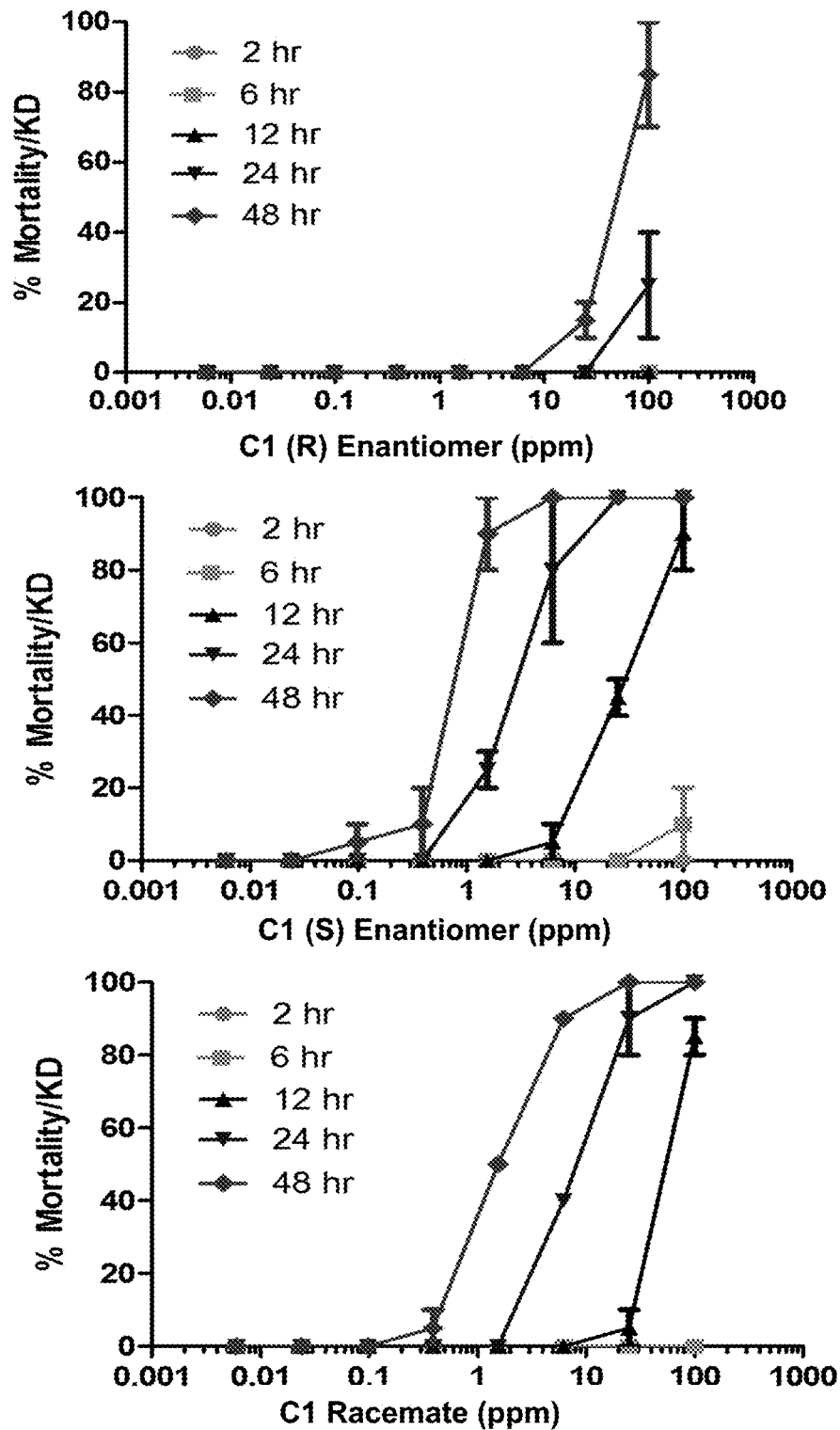
FIG. 7. Trial #1 activity of the C1 (R) enantiomer, C1 (S) enantiomer, and C1 racemate against *R. sanguineus* in a contact assay. Assay points assessing mortality were taken at 2, 6, 12, 24, and 48 hours at the indicated concentrations of C1 compound in parts per million (ppm).
Figure 10:
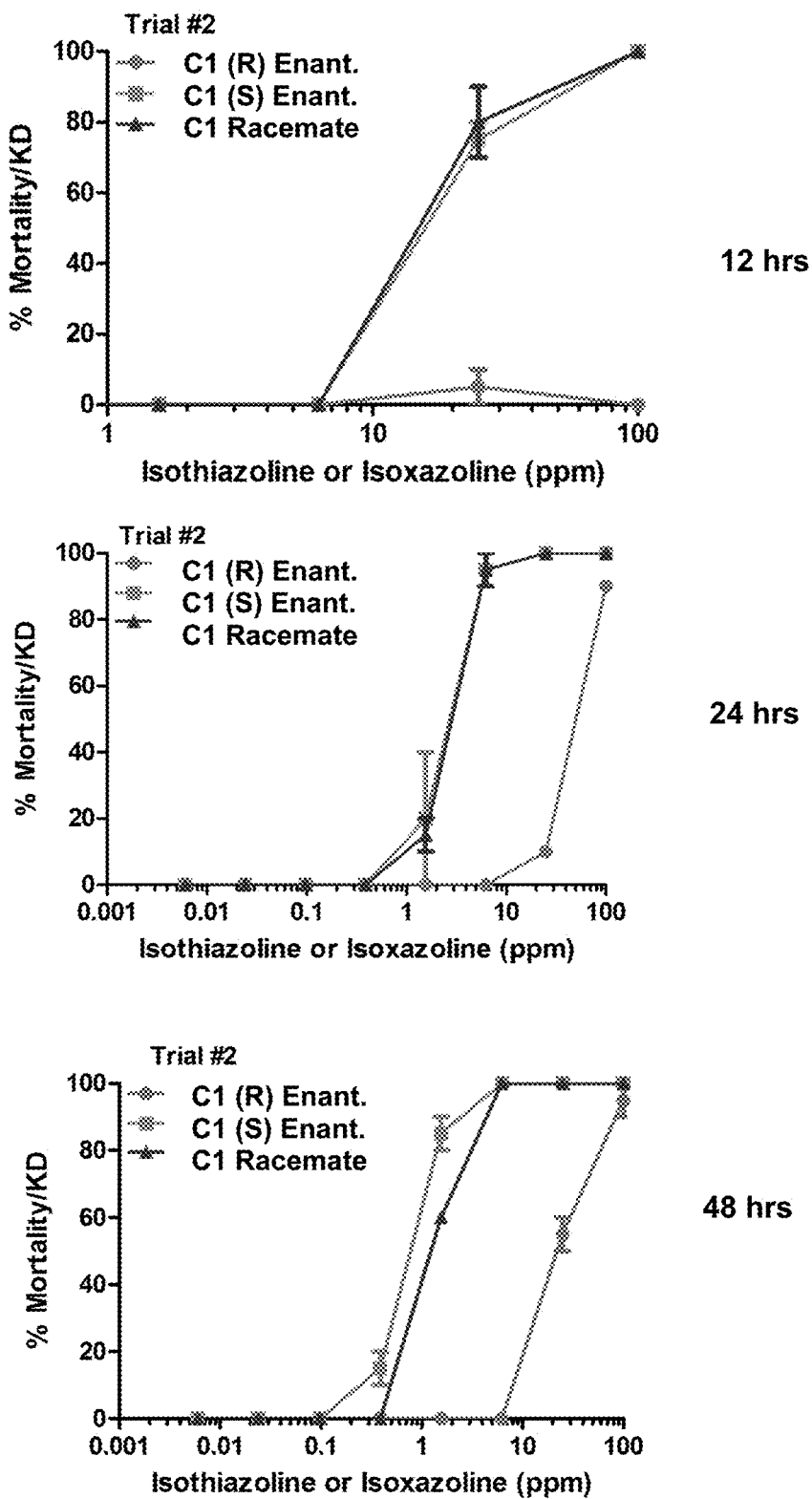
FIG. 10. Trial #2 activity of the C1 (R) enantiomer, C1 (S) enantiomer, and C1 racemate against *R. sanguineus* in a speed of kill in contact assay. Assay points assessing mortality were taken at 12, 24, and 48 hours at the indicated concentrations of C1 compound in parts per million (ppm).
Figure 13:
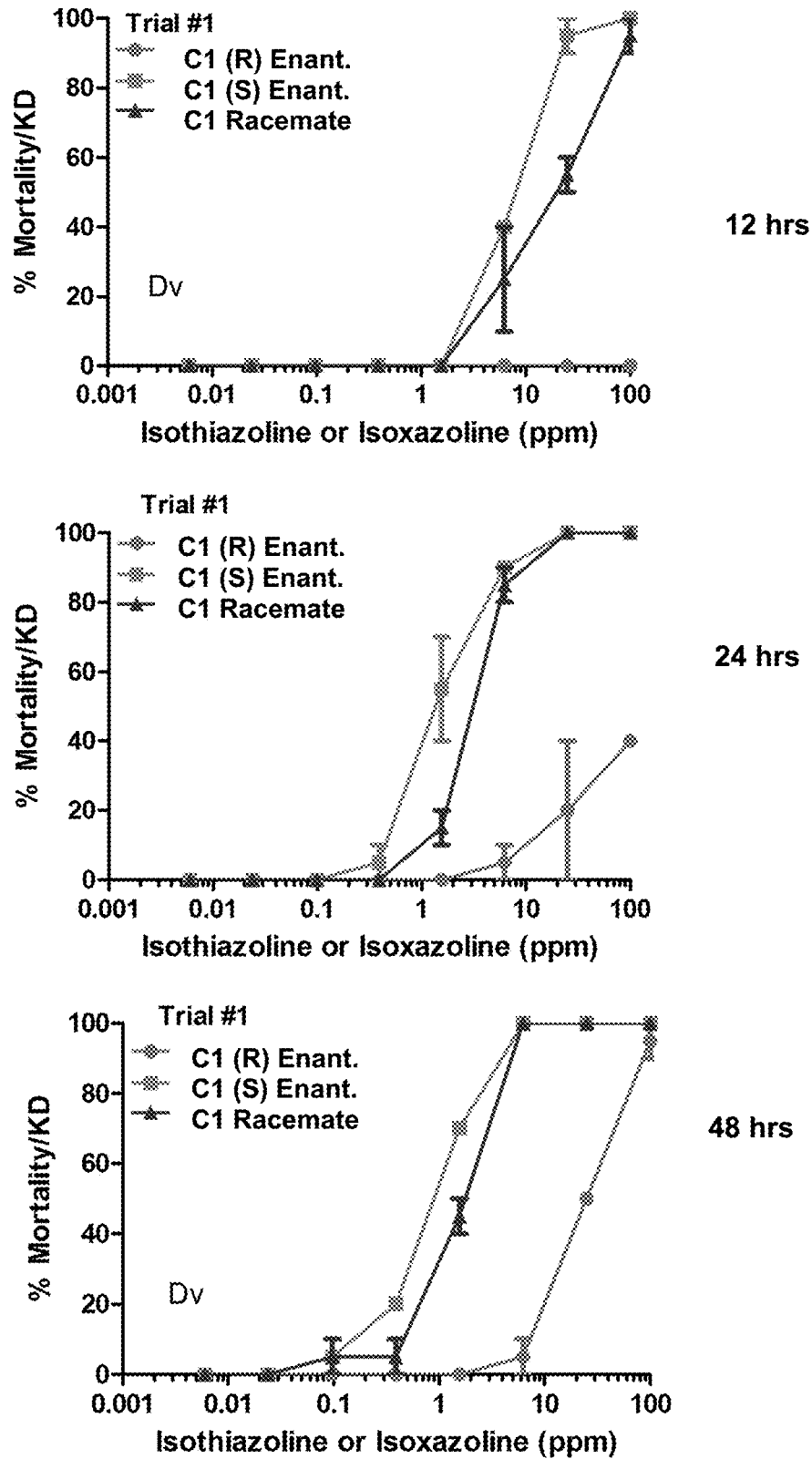
FIG. 13. Trial #1 activity of the C1 (R) enantiomer, C1 (S) enantiomer, and C1 racemate against *D. variabilis* in a speed of kill in contact assay. Assay points assessing mortality were taken at 12, 24, and 48 hours at the indicated concentrations of C1 compound in parts per million (ppm).
Figure 14:
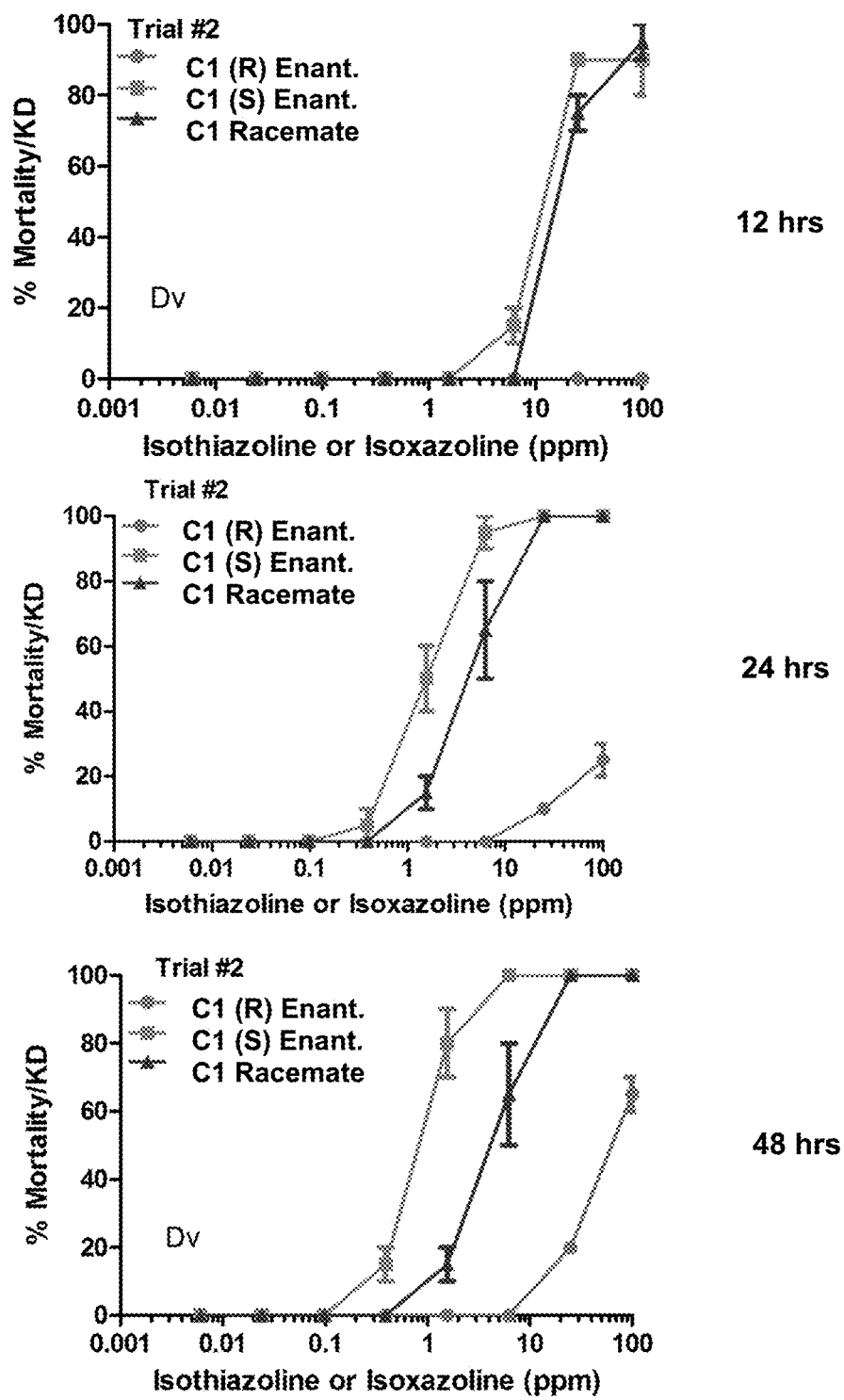
FIG. 14. Trial #2 activity of the C1 (R) enantiomer, C1 (S) enantiomer, and C1 racemate against *D. variabilis* in a speed of kill in contact assay. Assay points assessing mortality were taken at 12, 24, and 48 hours at the indicated concentrations of C1 compound in parts per million (ppm).
Figure 19:
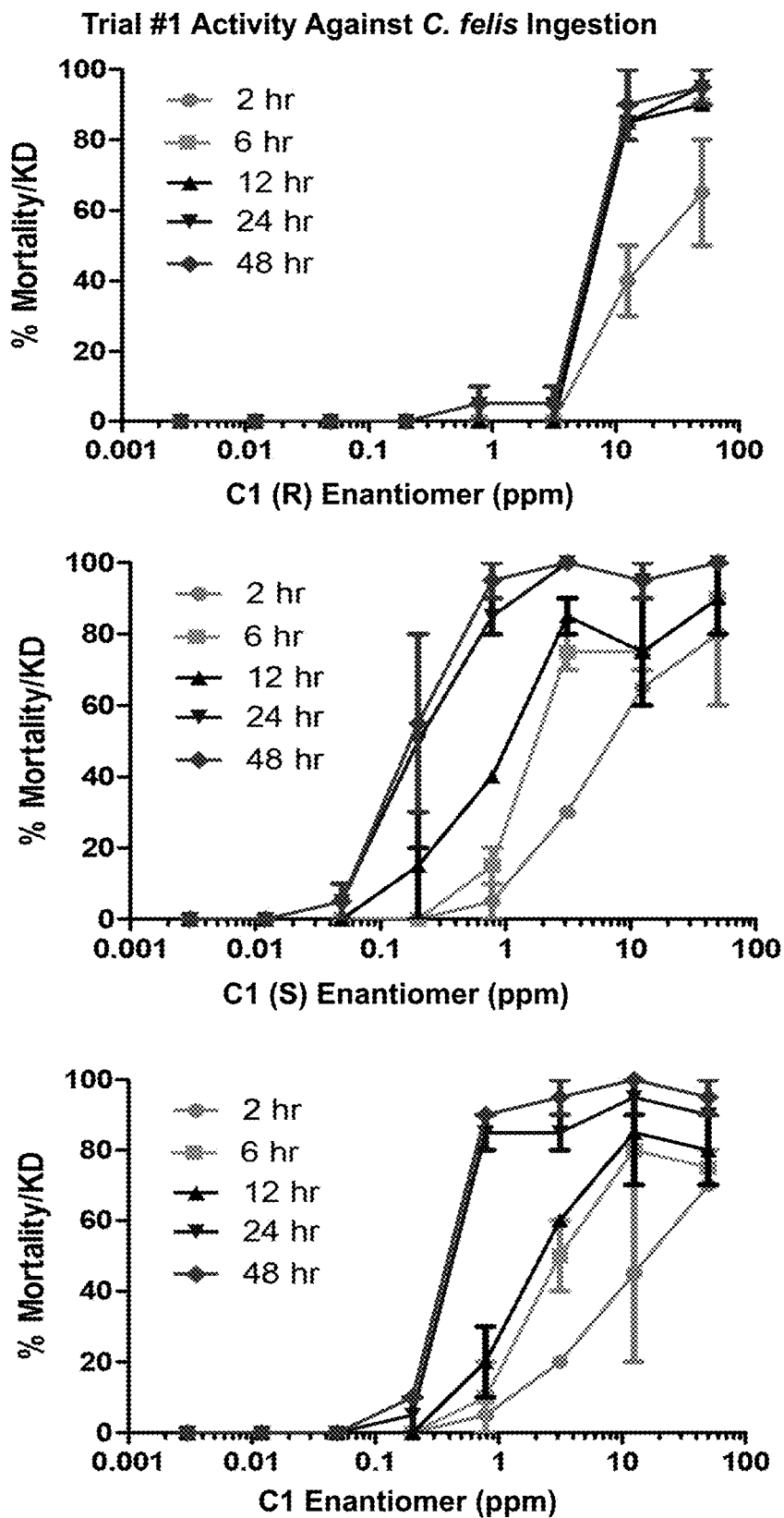
FIG. 19. Trial #1 activity of the C1 (R) enantiomer, C1 (S) enantiomer, and C1 racemate against *C. felis* in an ingestion assay. Assay points assessing mortality were taken at 2, 6, 12, 24, and 48 hours at the indicated concentrations of C1 compound in parts per million (ppm).
Figure 22:
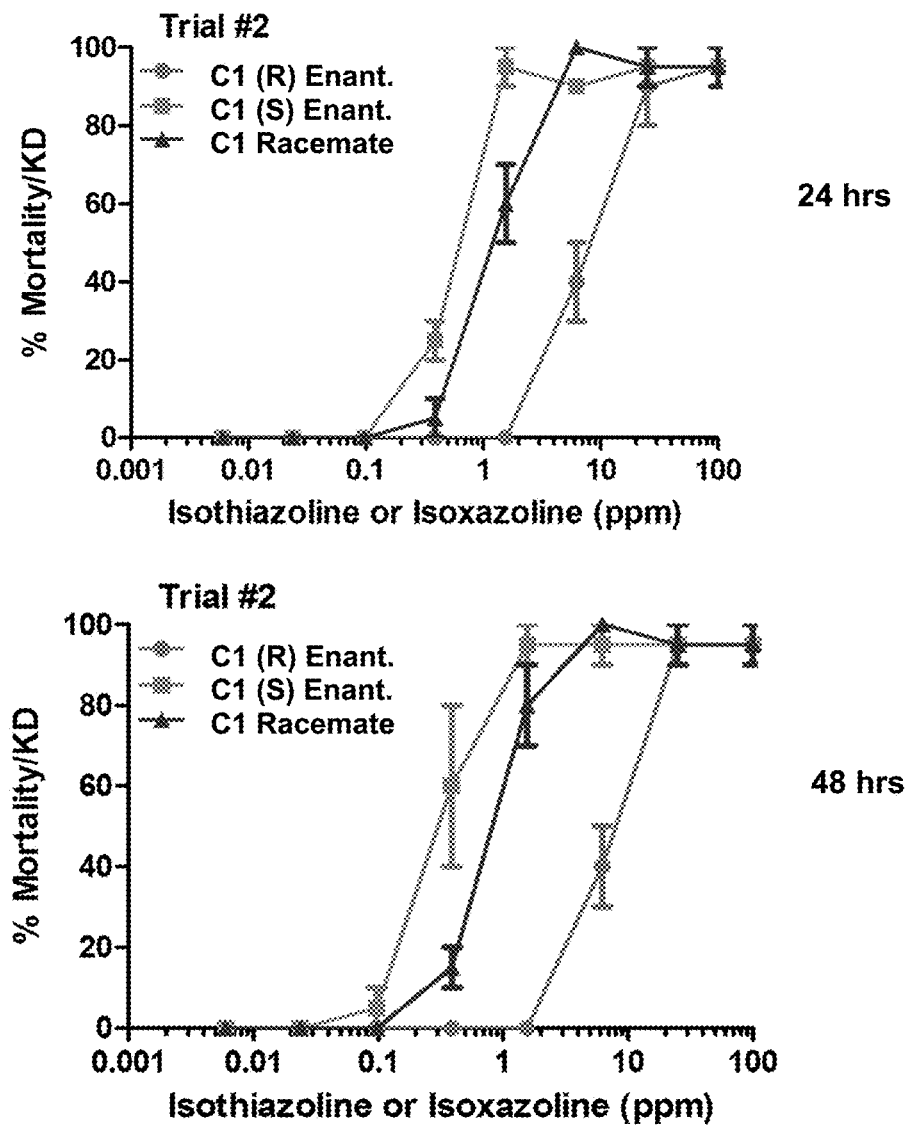
FIG. 22. Trial #2 activity of the C1 (R) enantiomer, C1 (S) enantiomer, and C1 racemate against *C. felis* in a speed of kill ingestion assay. Assay points assessing mortality were taken at 24 and 48 hours at the indicated concentrations of C1 compound in parts per million (ppm).

Chromatograms of all study samples showed single peak of C1 (S) Enantiomer and no peak for the C1 (R) enantiomer (R)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one. Representative chromatograms for the C1 (R) and C1 (S) enantiomer are show in FIGS. 5-6. No bioconversion was observed.

Example 4

Bio-Profiling of C1 racemate, C1 (S) enantiomer, and C1 (R) enantiomer against adult stages of *Ctenocephalides felis* (flea), Ixodidae (tick), and *Aedes aegypti* (mosquito)

Summary:

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one (referred to herein as C1 racemate) is an isothiazoline compound consisting of two isomers: (R)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one (referred herein as C1 (R) enantiomer) and (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one (referred to herein as C1 (S) enantiomer). The racemic compound and the two enantiomers were tested against adult stages of *Ctenocephalides felis* (flea) Ixodidae (tick), and *Aedes aegypti* (mosquito). The compounds were solubilized in DMSO or an acetone/triton solution and dose response curves were generated for the individual compounds.

For evaluation of contact activity, coated-substrate (flea) and coated-vial (tick and mosquito) assay procedures were used. For evaluation of flea ingestion activity, an artificial feeding assay procedure was used. Insecticidal activity was evaluated at various time-points for each assay. Dose response curves were generated in duplicate on three independent test occasions (Trial 1-Trial 3) and $EC_{50}$ and $EC_{90}$ values were calculated. The biological activity of the C1 racemate was found to primarily be associated with the C1 (S) enantiomer. The C1 racemate and especially the C1 (S) enantiomer displayed excellent potency against ticks.

Materials and General Methods

Test Substances:

C1 racemate, the C1 (R) enantiomer, and the C1 (S) enantiomer were synthesized and purified. Compounds were dissolved in DMSO to generate 10 mg/ml stock solutions.

I. Ticks

*Rhipicephalus sanguineus, Dermacentor variabilis, Amblyomma americanum,* (Ecto Services, Inc., Henderson, N.C.) and Ixodes scapularis (Oklahoma State University, Stillwater, Okla.) aged between 2-4 weeks post molt were held in an environmental chamber at 24° C., 80% humidity with 12-hour light/dark cycles.

In Vitro Evaluation of Contact Activity Against Adult Ticks

For tick assays, vial caps were pre-drilled with a single hole in the center of each cap to allow air exchange. A filter paper (Whatman Grade 540 2.1 cm) was placed in the lid of each vial. An aliquot from each compound stock was added to an acetone/triton solution to achieve the desired top doses for the study. Serial dilutions were conducted from the top dose (i.e. 100 ppm) to achieve the desired titration range for $EC_{50}$ and $EC_{90}$ determination. For *R. sanguineus, D. variabilis,* and *A. americanum,* the final DMSO concentration in each test vial was 0.5%. For *I. scapularis*, compounds were solubilized directly in an acetone/triton solution due to *I. scapularis'* sensitivity to DMSO. A 459 µL aliquot of each compound formulation was transferred to a vial containing a Whatman Grade 540 2.1 cm filter paper. Vials were immediately placed on an unheated roller unit to allow for an even coating of the vial walls. After vials were coated, 41 µL of each compound formulation was added to the filter paper embedded in each vial cap. Each cap was allowed to dry. The vials were loosely capped and allowed to dry for a minimum of four hours in a chemical fume hood.

Treatments for the Tick Contact and Ingestion Studies Included:

Trial 1 & Trial 2

Compounds tested were: the C1 racemate, the C1 (R) enantiomer, and the C1 (S) enantiomer Solvent-only (negative control)

Trial 3

Compounds tested were: the C1 racemate, C1 (R) enantiomer, and the C1 (S) enantiomer. For Trial 3, the C1 (R) enantiomer and the C1 (S) enantiomer were further chiral purified to achieve >99% purity.

Solvent-only (negative control)

Ten adult ticks were added to each vial and held at 24° C., 80% humidity with 12-hour light/dark cycles. Adult ticks were assessed for percent mortality at various time points between 2 hours and 48 hours post infestation. Ticks were stimulated on a heated roller unit and evaluated. Ticks showing no movement, or very slow and uncoordinated movement were noted as dead.

Results of *R. sanguineus* contact assays for trials 1 and 2 are shown in FIGS. 7-10 and the results for trial 3 is shown in table 9. Results of *D. variabilis* contact assays are shown in FIGS. 11-14. Results of *A. americanum* contact assays are shown in FIGS. 15-18. Results of *I. scapularis* contact assays are shown in Table 8.

TABLE 8

| | | \multicolumn{10}{c|}{Trial 1 Activity Against I. scapularis Contact} |
|---|---|---|---|---|---|---|---|---|---|---|---|
| | | 2 hr % Mortality | | 6 hr % Mortality | | 12 hr % Mortality | | 24 hr % Mortality | | 48 hr % Mortality | |
| Cmpnd | Dose µM | Rep1 | Rep2 | Rep1 | Rep2 | Rep1 | Rep2 | Rep1 | Rep2 | Rep1 | Rep2 |
| C1 (R) | 100 | 0 | 0 | 0 | 0 | 0 | 0 | 20 | 0 | 50 | 30 |
| C1 (R) | 25 | 0 | 0 | 0 | 0 | 0 | 0 | 0 | 0 | 10 | 30 |
| C1 (R) | 6.25 | 0 | 0 | 0 | 0 | 0 | 0 | 0 | 0 | 0 | 0 |
| C1 (R) | 1.56 | 0 | 0 | 0 | 0 | 0 | 0 | 0 | 0 | 0 | 0 |
| C1 (R) | 0.39 | 0 | 0 | 0 | 0 | 0 | 0 | 0 | 0 | 0 | 0 |
| C1 (R) | 0.098 | 0 | 0 | 0 | 0 | 0 | 0 | 0 | 0 | 0 | 0 |
| C1 (R) | 0.024 | 0 | 0 | 0 | 0 | 0 | 0 | 0 | 0 | 0 | 0 |
| C1 (R) | 0.006 | 0 | 0 | 0 | 0 | 0 | 0 | 0 | 0 | 0 | 0 |
| C1 (S) | 100 | 0 | 0 | 100 | 100 | 100 | 100 | 100 | 100 | 100 | 100 |
| C1 (S) | 25 | 0 | 0 | 40 | 40 | 100 | 90 | 100 | 100 | 100 | 100 |
| C1 (S) | 6.25 | 0 | 0 | 0 | 0 | 40 | 50 | 100 | 90 | 100 | 100 |
| C1 (S) | 1.56 | 0 | 0 | 0 | 0 | 0 | 0 | 50 | 60 | 90 | 100 |
| C1 (S) | 0.39 | 0 | 0 | 0 | 0 | 0 | 0 | 0 | 0 | 40 | 40 |
| C1 (S) | 0.098 | 0 | 0 | 0 | 0 | 0 | 0 | 0 | 0 | 10 | 10 |
| C1 (S) | 0.024 | 0 | 0 | 0 | 0 | 0 | 0 | 0 | 0 | 0 | 0 |
| C1 (S) | 0.006 | 0 | 0 | 0 | 0 | 0 | 0 | 0 | 0 | 0 | 10 |
| C1 Rac. | 100 | 0 | 0 | 100 | 50 | 100 | 100 | 100 | 100 | 100 | 100 |
| C1 Rac. | 25 | 0 | 0 | 10 | 40 | 50 | 70 | 90 | 100 | 100 | 100 |
| C1 Rac. | 6.25 | 0 | 0 | 0 | 0 | 0 | 70 | 80 | 100 | 100 | 100 |
| C1 Rac. | 1.56 | 0 | 0 | 0 | 0 | 0 | 0 | 10 | 30 | 90 | 80 |
| C1 Rac. | 0.39 | 0 | 0 | 0 | 0 | 0 | 10 | 50 | 50 | 70 | 100 |
| C1 Rac. | 0.098 | 0 | 0 | 0 | 0 | 0 | 0 | 0 | 20 | 0 | 60 |
| C1 Rac. | 0.024 | 0 | 0 | 0 | 0 | 0 | 0 | 0 | 30 | 10 | 30 |
| C1 Rac. | 0.006 | 0 | 0 | 0 | 0 | 0 | 0 | 0 | 0 | 10 | 0 |

*cmpnd = compound;
C1 (R) = C1 (R) enantiomer;
C1 (S) = C1 (S) enantiomer;
C1 Rac. = C1 Racemate;
R1 + R2 is the total mortality between two separate replicate experiments.

TABLE 9

Trial 3 Activity Against R. sanguineus Contact

| Cmpnd | Dose μM | 2 hr % Mortality | | 6 hr % Mortality | | 12 hr % Mortality | |
|---|---|---|---|---|---|---|---|
| | | Rep1 | Rep2 | Rep1 | Rep2 | Rep1 | Rep2 |
| C1 (R) | 100 | 0 | 0 | 0 | 0 | 0 | 0 |
| C1 (R) | 25 | 0 | 0 | 0 | 0 | 0 | 0 |
| C1 (R) | 6.25 | 0 | 0 | 0 | 0 | 0 | 0 |
| C1 (R) | 1.56 | 0 | 0 | 0 | 0 | 0 | 0 |
| C1 (R) | 0.39 | 0 | 0 | 0 | 0 | 0 | 0 |
| C1 (R) | 0.098 | 0 | 0 | 0 | 0 | 0 | 0 |
| C1 (R) | 0.024 | 0 | 0 | 0 | 0 | 0 | 0 |
| C1 (R) | 0.006 | 0 | 0 | 0 | 0 | 0 | 0 |
| C1 (S) | 100 | 50 | 10 | 100 | 100 | 100 | 100 |
| C1 (S) | 25 | 0 | 0 | 90 | 100 | 100 | 100 |
| C1 (S) | 6.25 | 0 | 0 | 80 | 60 | 100 | 100 |
| C1 (S) | 1.56 | 0 | 0 | 10 | 0 | 40 | 50 |
| C1 (S) | 0.39 | 0 | 0 | 0 | 0 | 10 | 10 |
| C1 (S) | 0.098 | 0 | 0 | 0 | 0 | 0 | 0 |
| C1 (S) | 0.024 | 0 | 0 | 0 | 0 | 0 | 0 |
| C1 (S) | 0.006 | 0 | 0 | 0 | 0 | 0 | 0 |
| C1 Rac. | 100 | 10 | 0 | 100 | 100 | 100 | 100 |
| C1 Rac. | 25 | 30 | 10 | 90 | 100 | 90 | 100 |
| C1 Rac. | 6.25 | 0 | 0 | 50 | 20 | 80 | 80 |
| C1 Rac. | 1.56 | 0 | 0 | 0 | 0 | 90 | 50 |
| C1 Rac. | 0.39 | 0 | 0 | 10 | 0 | 10 | 0 |
| C1 Rac. | 0.098 | 0 | 0 | 0 | 0 | 0 | 0 |
| C1 Rac. | 0.024 | 0 | 0 | 0 | 0 | 0 | 0 |
| C1 Rac. | 0.006 | 0 | 0 | 0 | 0 | 0 | 0 |

*cmpnd = compound;
C1 (R) = C1(R) enantiomer;
C1 (S) = C1 (S) enantiomer;
C1 Rac. = C1 Racemate;
R1 + R2 is the total mortality between two separate replicate experiments.

II. Fleas

*Ctenocephalides felis* (Avista Pharma, Inc., RTP, NC), 1-7days post hatch, held in an environmental chamber at 24° C., 85% humidity.

In Vitro Evaluation of Contact Activity Against Fleas (*Ctenocephalides felis*)

For flea contact tests, vial caps were pre-drilled with a single hole in the center of each cap to allow air exchange. A filter paper (Whatman Grade 540 2.1 cm) was placed in the lid of each vial. Pipe cleaners cut to 0.5 inches were inserted in each test vial. An aliquot was taken from each compound stock and added to an acetone/triton solution to achieve the desired top concentrations for the study. Serial dilutions were conducted from the top dose (i.e. 100 ppm) to achieve the desired concentration for $EC_{50}$ and $EC_{90}$ determination. The final DMSO concentration was 0.5%. A 75 μL aliquot of each compound formulation was added to each 0.5 inch pipe cleaner contained in the treatment vial. The vials were loosely capped and allowed to dry for a minimum of four hours in a chemical fume hood.

In Vitro Evaluation of Ingestion Activity Against Fleas (*Ctenocephalides felis*)

For flea ingestion tests, serial dilutions of the compound stock were performed using DMSO to achieve the desired range for $EC_{50}$ and $EC_{90}$ determination. An aliquot of each compound dilution was added to organic bovine blood with a final DMSO concentration of 0.5% and placed in an artificial feeding container.

Treatments for the Flea Contact and Ingestion Studies Included:

Trial 1 & Trial 2

Compounds tested were C1 racemate, the C1 (R) enantiomer, and the C1 (S) enantiomer.

Solvent-only (negative control)

Trial 3

Compounds tested were C1 racemate, the C1 (R) enantiomer, and the C1 (S) enantiomer. For Trial 3, the C1 (R) enantiomer and the C1 (S) enantiomer were further chiral purified to achieve >99% purity.

Solvent-only (negative control)

For both contact and ingestion assays, ten newly emerged unfed adult fleas, 0-7 days old *Ctenocephalides felis*, from a laboratory colony, were aspirated into each vial or cage. The test vials for contact assays were held in an environmental chamber at 24° C., 80% humidity with light/dark cycles (12 hours each). The cages for flea ingestion assays were held in a temperature-controlled artificial feeding apparatus to allow continual access to organic bovine blood containing the desired concentration of compound. Fresh aliquots of compound-spiked bovine blood were provided daily for the duration of the study.

Fleas were evaluated for percent mortality at various time points between 2 hours and 48 hours post infestation. Fleas showing normal movement and/or jumping ability were considered viable and those showing no movement after tapping the vials were scored as dead.

Figure 23:
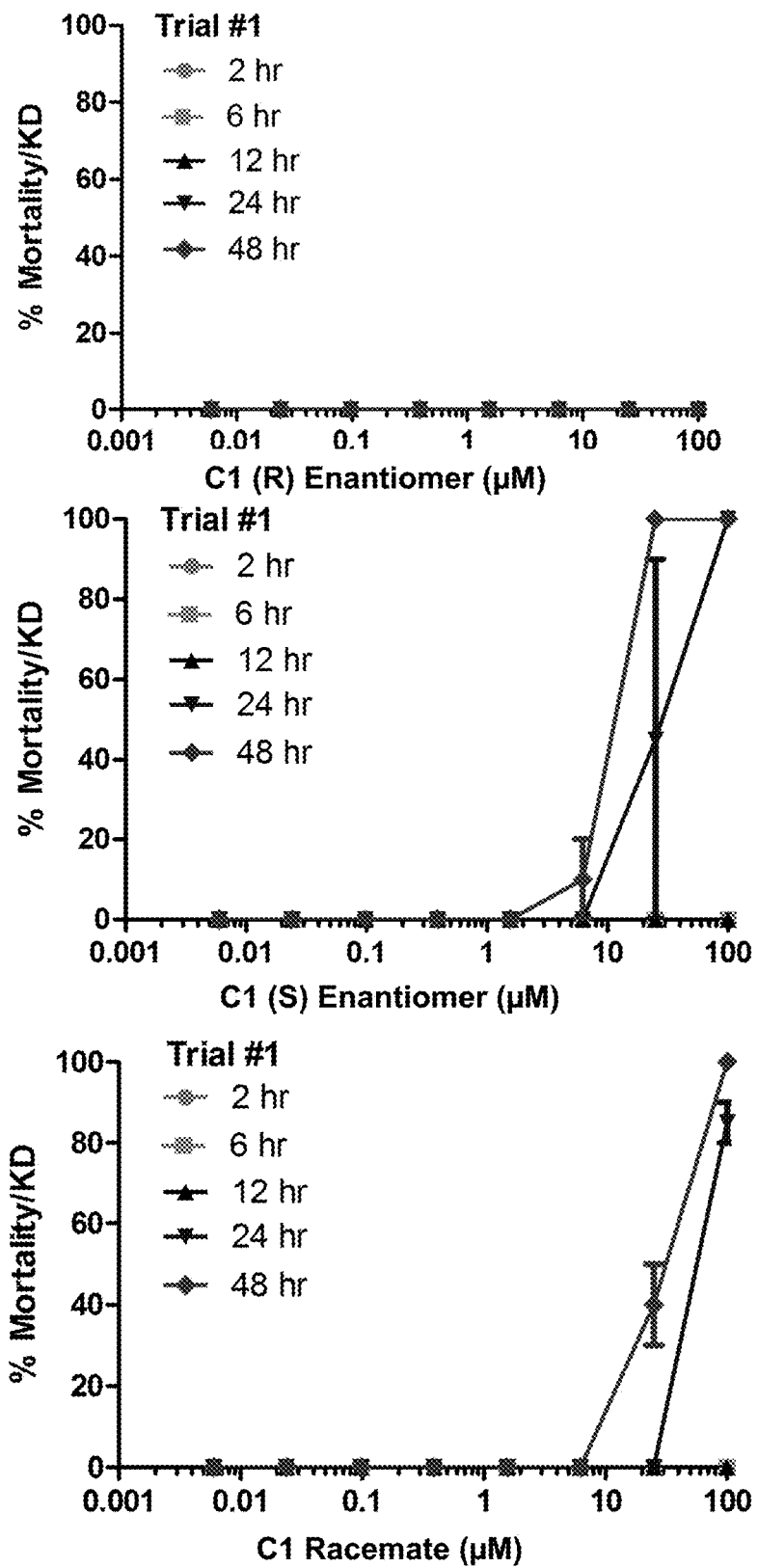
FIG. 23. Trial #1 activity of the C1 (R) enantiomer, C1 (S) enantiomer, and C1 racemate against *C. felis* in a contact assay. Assay points assessing mortality were taken at 2, 6, 12, 24, and 48 hours at the indicated concentrations of C1 compound in (μM).

Results of *C. felis* ingestion assays for trials 1 and 2 are shown in FIGS. 19-22 and trial 3 is shown in table 10. The results for contact assays for trials 1 and 2 are shown in FIGS. 23-24 and trial 3 is shown in table 11.

TABLE 10

Trial 3 Activity Against C. felis in Ingestion Assay

| Cmpnd | Dose ppm | 6 hr % Mortality | | 24 hr % Mortality | | 48 hr % Mortality | |
|---|---|---|---|---|---|---|---|
| | | Rep1 | Rep2 | Rep1 | Rep2 | Rep1 | Rep2 |
| C1 (R) | 50 | 100 | 100 | 100 | 100 | 100 | 100 |
| C1 (R) | 12.5 | 80 | 40 | 80 | 40 | 90 | 60 |
| C1 (R) | 3.125 | 0 | 20 | 0 | 0 | 0 | 0 |
| C1 (R) | 0.78 | 0 | 0 | 0 | 0 | 0 | 0 |
| C1 (R) | 0.20 | 0 | 0 | 0 | 0 | 0 | 0 |
| C1 (R) | 0.049 | 0 | 0 | 0 | 0 | 0 | 0 |
| C1 (R) | 0.012 | 0 | 0 | 0 | 0 | 0 | 0 |
| C1 (R) | 0.003 | 0 | 0 | 0 | 0 | 0 | 0 |
| C1 (S) | 50 | 100 | 100 | 100 | 100 | 100 | 100 |
| C1 (S) | 12.5 | 100 | 100 | 100 | 100 | 100 | 100 |
| C1 (S) | 3.125 | 100 | 60 | 100 | 80 | 100 | 100 |
| C1 (S) | 0.78 | 80 | 70 | 100 | 90 | 100 | 90 |
| C1 (S) | 0.20 | 10 | 20 | 10 | 50 | 30 | 70 |
| C1 (S) | 0.049 | 0 | 0 | 20 | 10 | 20 | 20 |
| C1 (S) | 0.012 | 0 | 0 | 0 | 0 | 0 | 0 |
| C1 (S) | 0.003 | 0 | 0 | 0 | 0 | 0 | 0 |
| C1 Rac. | 50 | 90 | 70 | 90 | 80 | 90 | 90 |
| C1 Rac. | 12.5 | 90 | 100 | 90 | 100 | 90 | 100 |
| C1 Rac. | 3.125 | 90 | 70 | 90 | 90 | 90 | 100 |
| C1 Rac. | 0.78 | 70 | 90 | 90 | 90 | 90 | 100 |
| C1 Rac. | 0.20 | 10 | 10 | 30 | 80 | 80 | 80 |
| C1 Rac. | 0.049 | 0 | 0 | 0 | 10 | 10 | 10 |
| C1 Rac. | 0.012 | 0 | 0 | 0 | 0 | 0 | 0 |
| C1 Rac. | 0.003 | 0 | 0 | 0 | 0 | 0 | 0 |

*cmpnd = compound;
C1 (R) = C1(R) enantiomer;
C1 (S) = C1(S) enantiomer;
C1 Rac. = C1 Racemate;
R1 + R2 is the total mortality between two separate replicate experiments.

TABLE 11

Trial 3 Activity Against C. felis Contact

| Cmpnd | Dose ppm | 6 hr % Mortality | | 24 hr % Mortality | | 48 hr % Mortality | |
|---|---|---|---|---|---|---|---|
| | | Rep1 | Rep2 | Rep1 | Rep2 | Rep1 | Rep2 |
| C1 (R) | 100 | 0 | 0 | 0 | 0 | 0 | 0 |
| C1 (R) | 25 | 0 | 0 | 0 | 0 | 0 | 0 |
| C1 (R) | 6.25 | 0 | 0 | 0 | 0 | 0 | 0 |
| C1 (R) | 1.56 | 0 | 0 | 0 | 0 | 0 | 0 |
| C1 (R) | 0.39 | 0 | 0 | 0 | 0 | 0 | 0 |
| C1 (R) | 0.098 | 0 | 0 | 0 | 0 | 0 | 0 |
| C1 (R) | 0.024 | 0 | 0 | 0 | 0 | 0 | 0 |
| C1 (R) | 0.006 | 0 | 0 | 0 | 0 | 0 | 0 |
| C1 (S) | 100 | 0 | 0 | 100 | 100 | 100 | 100 |
| C1 (S) | 25 | 0 | 0 | 30 | 20 | 100 | 100 |
| C1 (S) | 6.25 | 0 | 0 | 10 | 10 | 70 | 30 |
| C1 (S) | 1.56 | 0 | 0 | 0 | 0 | 10 | 30 |
| C1 (S) | 0.39 | 0 | 0 | 0 | 0 | 10 | 0 |
| C1 (S) | 0.098 | 0 | 0 | 0 | 0 | 10 | 10 |
| C1 (S) | 0.024 | 0 | 0 | 0 | 0 | 0 | 0 |
| C1 (S) | 0.006 | 0 | 0 | 0 | 0 | 0 | 0 |
| C1 Rac. | 100 | 0 | 0 | 70 | 40 | 100 | 100 |
| C1 Rac. | 25 | 0 | 0 | 0 | 0 | 80 | 70 |
| C1 Rac. | 6.25 | 0 | 0 | 0 | 0 | 0 | 0 |
| C1 Rac. | 1.56 | 0 | 0 | 0 | 0 | 0 | 0 |
| C1 Rac. | 0.39 | 0 | 0 | 0 | 0 | 0 | 0 |
| C1 Rac. | 0.098 | 0 | 0 | 0 | 0 | 0 | 0 |
| C1 Rac. | 0.024 | 0 | 0 | 0 | 0 | 0 | 0 |
| C1 Rac. | 0.006 | 0 | 0 | 0 | 0 | 0 | 0 |

*cmpnd = compound;
C1 (R) = C1 (R) enantiomer;
C1 (S) = C1 (S) enantiomer;
C1 Rac. = C1 Racemate;
R1 + R2 is the total mortality between two separate replicate experiments.

III. Mosquitoes

*Aedes aegypti* (Louisiana Biologicals Inc., New Orleans, La.) eggs were allowed to hatch, close, and age between 3-5 days in an environmental chamber at 26° C., 80% humidity with light/dark cycles.

In Vitro Evaluation of Contact Activity Against Adult Mosquitoes (*Aedes aegypti*)

For mosquito assays, an aliquot from each compound stock was added to an acetone/triton solution to achieve the desired top doses for the study. Serial dilutions were conducted from the top dose (i.e. 50 ppm) to achieve the desired titration range for $EC_{50}$ and $EC_{90}$ determination. The final DMSO concentration in each test vial was 0.5%. A 459 µL aliquot of each compound formulation was transferred to a vial and vials were immediately placed on an unheated roller unit to allow for an even coating of the vial walls. The vials were loosely capped and allowed to dry for a minimum of four hours in a chemical fume hood.

In Vitro Evaluation of Ingestion Activity Against Adult Mosquitoes (*Aedes aegypti*)

For mosquito ingestion tests, serial dilutions of the compound stock were performed using DMSO to achieve the desired range for $EC_{50}$ and $EC_{90}$ determination. An aliquot of each compound dilution was added to organic bovine blood with a final DMSO concentration of 0.5% and placed in a temperature-controlled artificial feeding container.

Treatments for the Mosquito Contact and Ingestion Studies Included:

Trial 1 & Trial 2
  Compounds tested were: the C1 racemate, C1 (R) enantiomer, and the C1 (S) enantiomer
  Solvent-only (negative control)

Trial 3
  Compounds tested were: the C1 racemate, C1 (R) enantiomer, and the C1 (S) enantiomer. For Trial 3, the C1 (R) enantiomer and the C1 (S) enantiomer were further chiral purified to achieve >99% purity.
  Solvent-only (negative control)

For both contact and ingestion assays, five female *Aedes aegypti* adults were added to each vial or cage. The test vials for contact assays were held in an environmental chamber at 24° C., 80% humidity with light/dark cycles (12 hours each). The cages for mosquito ingestion assays were held in a temperature-controlled artificial feeding apparatus to allow continual access to organic bovine blood containing the desired concentration of compound. Fresh aliquots of compound-spiked bovine blood were provided daily for the duration of the study.

Assessment of mortality/knockdown was performed at various time points between 30 minutes and 24 hours post infestation. Mosquitoes showing no movement or mosquitoes that were knocked down were noted as dead. Results from trial 1 and trial 2 contact assays are shown in Tables 12 and 13, respectively and the results from trial 3 mosquito ingestion assay is shown in table 14.

TABLE 12

Trial 1 Activity against Mosquitoes in Contact Assay

| Cmpnd | Dose µM | 0.5 Hr % Mortality R1 + R2 | 1 hr % Mortality R1 + R2 | 6 hr % Mortality R1 + R2 | 12 hr % Mortality R1 + R2 | 24 hr % Mortality R1 + R2 | 48 hr % Mortality R1 + R2 |
|---|---|---|---|---|---|---|---|
| C1 (R) | 50 | 0 | 0 | 0 | 30 | 100 | 100 |
| C1 (R) | 12.5 | 0 | 0 | 0 | 0 | 0 | 50 |
| C1 (R) | 3.125 | 0 | 0 | 0 | 0 | 0 | 30 |
| C1 (R) | 0.78 | 0 | 0 | 0 | 0 | 0 | 20 |
| C1 (R) | 0.20 | 0 | 0 | 0 | 0 | 0 | 40 |
| C1 (R) | 0.049 | 0 | 0 | 0 | 0 | 0 | 10 |
| C1 (S) | 50 | 0 | 0 | 100 | 100 | 100 | 100 |
| C1 (S) | 12.5 | 0 | 0 | 30 | 70 | 100 | 100 |
| C1 (S) | 3.125 | 0 | 0 | 0 | 10 | 60 | 100 |
| C1 (S) | 0.78 | 0 | 0 | 0 | 0 | 0 | 10 |
| C1 (S) | 0.20 | 0 | 0 | 0 | 0 | 0 | 10 |
| C1 (S) | 0.049 | 0 | 0 | 0 | 0 | 0 | 0 |
| C1 Rac. | 50 | 0 | 0 | 80 | 100 | 100 | 100 |
| C1 Rac. | 12.5 | 0 | 0 | 0 | 0 | 90 | 100 |
| C1 Rac. | 3.125 | 0 | 0 | 0 | 0 | 0 | 90 |
| C1 Rac. | 0.78 | 0 | 0 | 0 | 0 | 0 | 30 |

TABLE 12-continued

| | | 0.5 Hr | 1 hr | 6 hr | 12 hr | 24 hr | 48 hr |
| | Dose | % Mortality | % Mortality | % Mortality | % Mortality | % Mortality | % Mortality |
| Cmpnd | μM | R1 + R2 | R1 + R2 | R1 + R2 | R1 + R2 | R1 + R2 | R1 + R2 |
| --- | --- | --- | --- | --- | --- | --- | --- |
| C1 Rac. | 0.20 | 0 | 0 | 0 | 0 | 0 | 20 |
| C1 Rac. | 0.049 | 0 | 0 | 0 | 0 | 0 | 40 |

*cmpnd = compound;
C1 (R) = C1 (R) enantiomer;
C1 (S) = C1 (S) enantiomer;
C1 Rac. = C1 Racemate;
R1 + R2 is the total mortality between two separate replicate experiments.

TABLE 13

Trial 2 Activity against Mosquitoes in Contact Assay

| | | 0.5 Hr | 1 hr | 6 hr | 12 hr | 24 hr | 48 hr |
| | Dose | % Mortality | % Mortality | % Mortality | % Mortality | % Mortality | % Mortality |
| Cmpnd | μM | R1 + R2 | R1 + R2 | R1 + R2 | R1 + R2 | R1 + R2 | R1 + R2 |
| --- | --- | --- | --- | --- | --- | --- | --- |
| C1 (R) | 50 | 0 | 0 | 0 | 20 | 100 | 100 |
| C1 (R) | 12.5 | 0 | 0 | 0 | 0 | 60 | 100 |
| C1 (R) | 3.125 | 0 | 0 | 0 | 0 | 10 | 20 |
| C1 (R) | 0.78 | 0 | 0 | 0 | 10 | 10 | 10 |
| C1 (R) | 0.20 | 0 | 0 | 0 | 10 | 0 | 60 |
| C1 (R) | 0.049 | 0 | 0 | 0 | 0 | 0 | 20 |
| C1 (S) | 50 | 0 | 0 | 100 | 100 | 100 | 100 |
| C1 (S) | 12.5 | 0 | 0 | 10 | 100 | 100 | 100 |
| C1 (S) | 3.125 | 0 | 0 | 0 | 20 | 100 | 100 |
| C1 (S) | 0.78 | 0 | 0 | 0 | 0 | 0 | 100 |
| C1 (S) | 0.20 | 0 | 0 | 0 | 10 | 30 | 90 |
| C1 (S) | 0.049 | 0 | 0 | 0 | 0 | 0 | 0 |
| C1 Rac. | 50 | 0 | 0 | 100 | 100 | 100 | 100 |
| C1 Rac. | 12.5 | 0 | 0 | 10 | 80 | 100 | 100 |
| C1 Rac. | 3.125 | 0 | 0 | 0 | 0 | 70 | 100 |
| C1 Rac. | 0.78 | 0 | 0 | 0 | 0 | 0 | 0 |
| C1 Rac. | 0.20 | 0 | 0 | 0 | 0 | 0 | 40 |
| C1 Rac. | 0.049 | 0 | 0 | 0 | 0 | 0 | 0 |

*cmpnd = compound;
C1 (R) = C1 (R) enantiomer;
C1 (S) = C1 (S) enantiomer;
C1 Rac. = C1 Racemate;
R1 + R2 is the total mortality between two separate replicate experiments.

TABLE 14

Trial 3 Activity against Mosquitoes in Ingestion Assay

| | | | | 6 horus | | | 24 hours | | |
| | | Dose | Total # | Mortality % | | | | | |
| Cmpnd | Vial # | ppm | Fed | Rep1 | Rep2 | R1 + R2 | Rep1 | Rep2 | R1 + R2 |
| --- | --- | --- | --- | --- | --- | --- | --- | --- | --- |
| C1 (R) | 1 | 50 | 9 | 4 | 4 | 88.9 | 4 | 5 | 100.0 |
| C1 (R) | 2 | 12.5 | 10 | 5 | 5 | 100.0 | 5 | 5 | 100.0 |
| C1 (R) | 3 | 3.125 | 9 | 1 | 0 | 11.1 | 4 | 5 | 100.0 |
| C1 (R) | 4 | 0.78 | 8 | 0 | 0 | 0.0 | 3 | 3 | 75.0 |
| C1 (R) | 5 | 0.20 | 10 | 0 | 1 | 10.0 | 2 | 1 | 30.0 |
| C1 (R) | 6 | 0.049 | 10 | 0 | 1 | 10.0 | 2 | 2 | 40.0 |
| C1 (S) | 1 | 50 | 10 | 5 | 5 | 100.0 | 5 | 5 | 100.0 |
| C1 (S) | 2 | 12.5 | 10 | 5 | 5 | 100.0 | 5 | 5 | 100.0 |
| C1 (S) | 3 | 3.125 | 9 | 4 | 5 | 100.0 | 4 | 5 | 100.0 |
| C1 (S) | 4 | 0.78 | 8 | 4 | 4 | 100.0 | 4 | 4 | 100.0 |
| C1 (S) | 5 | 0.20 | 9 | 3 | 1 | 44.4 | 4 | 5 | 100.0 |
| C1 (S) | 6 | 0.049 | 10 | 0 | 0 | 0.0 | 4 | 3 | 70.0 |
| C1 Rac. | 1 | 50 | 8 | 5 | 3 | 100.0 | 4 | 4 | 100.0 |
| C1 Rac. | 2 | 12.5 | 8 | 4 | 4 | 100.0 | 4 | 4 | 100.0 |
| C1 Rac. | 3 | 3.125 | 9 | 5 | 4 | 100.0 | 4 | 5 | 100.0 |
| C1 Rac. | 4 | 0.78 | 10 | 2 | 3 | 50.0 | 5 | 5 | 100.0 |

TABLE 14-continued

Trial 3 Activity against Mosquitoes in Ingestion Assay

| | | | | 6 horus | | | 24 hours | | |
|---|---|---|---|---|---|---|---|---|---|
| | | Dose | Total # | | | Mortality % | | | |
| Cmpnd | Vial # | ppm | Fed | Rep1 | Rep2 | R1 + R2 | Rep1 | Rep2 | R1 + R2 |
| C1 Rac. | 5 | 0.20 | 6 | 0 | 0 | 0.0 | 2 | 4 | 100.0 |
| C1 Rac. | 6 | 0.049 | 7 | 0 | 0 | 0.0 | 3 | 2 | 71.4 |

*cmpnd = compound;
C1 (R) = C1 (R) enantiomer;
C1 (S) = C1 (S) enantiomer;
C1 Rac. = C1 Racemate;
R1 + R2 is the total mortality between two separate replicate experiments.

Results

No significant mortality was observed in the negative controls (solvent-only treated vials). Therefore, mortality correction was not performed in the assays. Calculation of $EC_{50}$ and $EC_{90}$ values was performed using XLfit. Both $EC_{50}$ and $EC_{90}$ values were calculated using the average of the two replicates for each Trial.

Based on the results of Trial 1 and 2, time point selection was altered for testing the high-purity enantiomers in Trial 3.

For the mosquito contact and ingestion assays, each replicate contained 5 mosquitoes. For ease of calculation, the two replicates were added to equal a total of 10 mosquitoes.

SUMMARY AND CONCLUSIONS

The C1 (R) enantiomer, C1 (S) enantiomer, and the C1 racemate were successfully evaluated against flea, tick, and mosquito contact and ingestion in vitro screening assays. The results of Trial 1 and Trial 2, in conjunction with the >99% purity enantiomer data in Trial 3, suggest that the C1 (S) enantiomer is the active enantiomer of the C1 racemate.

All publications, patents and patent applications cited in this specification are incorporated herein by reference for the teaching to which such citation is used.

Test compounds for the experiments described herein were employed in free or salt form.

The specific responses observed may vary according to and depending on the particular active compound selected or whether there are present carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

The invention claimed is:

1. A compound of Formula (I), substantially free of an alternate stereoisomer, or a pesticidal, veterinary, or pharmaceutically acceptable salt thereof:

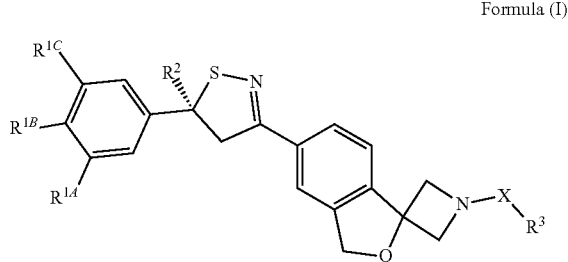

Formula (I)

wherein:
each $R^{1A}$, $R^{1B}$, and $R^{1C}$ individually is hydrogen, alkyl, halogen, or haloalkyl;
$R^2$ is haloalkyl;
X is bond, C(O), $SO_2$, or C(O)NH;
$R^3$ is hydrogen, optionally substituted alkyl, optionally substituted haloalkyl, optionally substituted cycloalkyl, optionally substituted heterocyclyl, optionally substituted aryl, and optionally substituted heteroaryl.

2. The compound of claim 1, wherein:
each $R^{1A}$, $R^{1B}$, and $R^{1C}$ individually is halogen, haloalkyl, or alkyl;
$R^2$ is haloalkyl;
X is a bond, C(O), $SO_2$, or C(O)NH; and
$R^3$ is alkyl, haloalkyl, or aryl.

3. The compound of claim 1, wherein:
each $R^{1A}$, $R^{1B}$, and $R^{1C}$ individually is halogen;
$R^2$ is perfluoroalkyl;
X is —C(O)—, —$SO_2$—, or —C(O)NH—; and
$R^3$ is haloalkyl.

4. The compound of claim 1, wherein:
each $R^{1A}$ and $R^{1C}$ is a halogen and $R^{1B}$ is a different halogen;
$R^2$ is haloalkyl;
X is —C(O)—; and
$R^3$ is haloalkyl.

5. The compound of claim 1 wherein:
each $R^{1A}$ and $R^{1C}$ is —Cl and $R^{1B}$ is —F;
$R^2$ is —$CF_3$;
X is —C(O)—; and
$R^3$ is —$CH_2CF_3$.

6. The compound of claim 1, wherein:
each $R^{1A}$ and $R^{1C}$ is —Cl and $R^{1B}$ is —F;
$R^2$ is —$CF_3$;
X is a bond, C(O), $SO_2$, or C(O)NH; and
$R^3$ is hydrogen, optionally substituted alkyl, optionally substituted haloalkyl, optionally substituted cycloalkyl, optionally substituted heterocyclyl, optionally substituted aryl, and optionally substituted heteroaryl.

7. The compound of claim 1, wherein R³ is alkyl; alkyl substituted with one or more alkoxy, alkylsulfonyl, cyano, or aryl; haloalkyl; cycloalkyl; cycloalkyl substituted with one or more alkyl, alkenyl, haloalkyl, haloalkenyl, alkoxy, or carbonyl; heterocyclyl; aryl; aryl substituted with one or more halogen; or heteroaryl.

8. A compound, substantially free of an alternate stereoisomer, wherein the compound is selected from:
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one;
- (S)-6-[5-(3,5-dichloro-4-fluoro-phenyl)-5-(trifluoromethyl)-4H-isothiazol-3-yl]-N-(2,2,2-trifluoroethyl)spiro[1H-isobenzofuran-3,3'-azetidine]-1'-carboxamide;
- (S)-6-[5-(3,5-dichloro-4-fluoro-phenyl)-5-(trifluoromethyl)-4H-isothiazol-3-yl]-1'-(4-fluorophenyl)sulfonyl-spiro[1H-isobenzofuran-3,3'-azetidine];
- (S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-phenyl-methanone;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methyl sulfonyl-ethanone;
- (S)-6-[5-(3,5-dichloro-4-fluoro-phenyl)-5-(trifluoromethyl)-4H-isothiazol-3-yl]spiro[1H-isobenzofuran-3,3'-azetidine];
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3-dimethyl-butan-1-one;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]butan-1-one;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-phenyl-ethanone;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-4,4,4-trifluoro-butan-1-one;
- (S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-(1-naphthyl)methanone;
- (S)-[(3Z,4Z)-4-allylidene-3-ethylidene-cyclohexa-1,5-dien-1-yl]-[6-[5-(3,5-dichloro-4-fluoro-phenyl)-5-(trifluoromethyl)-4H-isothiazol-3-yl]spiro[1H-isobenzofuran-3,3'-azetidine]-1'-yl]methanone;
- (S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-(4-morpholinophenyl)methanone;
- (S)-6-[5-(3,5-dichloro-4-fluoro-phenyl)-5-(trifluoromethyl)-4H-isothiazol-3-yl]-1'-propylsulfonyl-spiro[1H-isobenzofuran-3,3'-azetidine];
- (S)-6-[5-(3,5-dichloro-4-fluoro-phenyl)-5-(trifluoromethyl)-4H-isothiazol-3-yl]-1'-(3,3,3-trifluoropropylsulfonyl)spiro[1H-isobenzofuran-3,3'-azetidine];
- (S)-6-[5-(3,5-dichloro-4-fluoro-phenyl)-5-(trifluoromethyl)-4H-isothiazol-3-yl]-N-ethyl-spiro[1H-isobenzofuran-3,3'-azetidine]-1'-carboxamide;
- (S)-6-[5-(3,5-dichloro-4-fluoro-phenyl)-5-(trifluoromethyl)-4H-isothiazol-3-yl]-N-phenyl-spiro[1H-isobenzofuran-3,3'-azetidine]-1'-carboxamide;
- (S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-[3-(2,2-dichlorovinyl)-2,2-dimethyl-cyclopropyl]methanone;
- (S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-tetrahydropyran-4-yl-methanone;
- (S)-1'-butyl-6-[5-(3,5-dichloro-4-fluoro-phenyl)-5-(trifluoromethyl)-4H-isothiazol-3-yl]spiro[1H-isobenzofuran-3,3'-azetidine];
- (S)-6-[5-(3,5-dichloro-4-fluoro-phenyl)-5-(trifluoromethyl)-4H-isothiazol-3-yl]-1'-(3,3-dimethylbutyl)spiro[1H-isobenzofuran-3,3'-azetidine];
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methoxy-ethanone;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-isopropoxy-ethanone;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-ethoxy-ethanone;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methyl-propan-1-one;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]propan-1-one;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]ethanone;
- (S)-3-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-4-ethoxy-cyclobut-3-ene-1,2-dione;
- (S)-3-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3-oxo-propanenitrile;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2,2,3,3,3-pentafluoro-propan-1-one;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2,2-difluoro-propan-1-one;
- (S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-[1-(trifluoromethyl)cyclopropyl]methanone;
- (S)-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-[1-(trifluoromethyl)cyclobutyl]methanone;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-2,2-dimethyl-propan-1-one;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]pentan-1-one;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]hexan-1-one;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]heptan-1-one;
- (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]octan-1-one;

(S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]nonan-1-one;

(S)-6-[5-(3,5-dichloro-4-fluoro-phenyl)-5-(trifluoromethyl)-4H-isothiazol-3-yl]-1'-pyrimidin-2-yl-spiro[1H-isobenzofuran-3,3'-azetidine]; and (S)-6-[5-(3,5-dichloro-4-fluoro-phenyl)-5-(trifluoromethyl)-4H-isothiazol-3-yl]-N-methyl-spiro[1H-isobenzofuran-3,3'-azetidine]-1'-carboxamide, or a pesticidal, veterinary, or pharmaceutically acceptable salt thereof.

9. A compound, substantially free of an alternate stereoisomer, wherein the compound is (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one according to the structure:

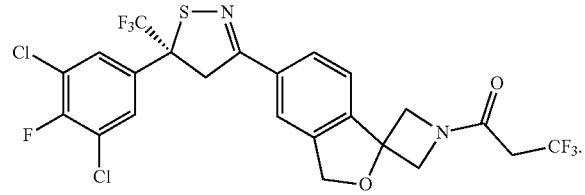 [SMILES: O=C(CC(F)(F)F)N1CC2(C1)OCc1cc(C3=NS[C@@](c4cc(Cl)c(F)c(Cl)c4)(C(F)(F)F)C3)ccc12]

10. A compound according to claim 1, wherein the compound is designated as the (S) enantiomer and is about 90%, 91%, 92%, 93%, 94%, 95%, 96%, 97%, 98%, 99%, 99.5%, 99.8%, 99.9%, or 100% free of (R) enantiomer.

11. A composition comprising a compound according to claim 1, and a pesticidally acceptable carrier.

12. A combination comprising a compound according to claim 1, and one or more other pesticidally active substances.

13. A composition comprising a compound (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof and one or more pesticidal, veterinary, or pharmaceutically acceptable carriers, wherein the composition is substantially free of a compound (R)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof.

14. A method for controlling one or more of fleas, ticks, helminthes and mosquitos at a locus in need thereof comprising: applying to the locus an effective amount of a compound according to claim 1.

15. A method of treating or preventing infection or infestation from one or more of fleas, ticks, helminthes and mosquitos in a subject in need thereof comprising: administering to the subject an effective amount of a compound according to claim 1.

16. The method of claim 14, wherein the method is to control fleas is a flea, tick, or mosquito.

17. The method of claim 14, wherein the flea or tick is *Ctenocephalides felis, R. sanguineus, D. variablis, A. americanum,* or *I. scapularis.*

18. The method of claim 14, wherein the method is to control a helminth.

19. The method of claim 14, wherein the mosquito is *Dirofilaria immitis.*

20. A method for making the compound of claim 9, the method comprising (a) preparing a mixture comprising 1-(5'-acetyl-3'H-spiro[azetidine-3,1'-isobenzofuran]-1-yl)-3,3,3-trifluoropropan-1-one and 1-(3,5-dichloro-4-fluorophenyl)-2,2,2-trifluoroethan-1-one and performing a reaction comprising reacting the mixture to obtain a compound (Z)-3-(3,5-dichloro-4-fluorophenyl)-4,4,4-trifluoro-1-(1-(3,3,3-trifluoropropanoyl)-3'H-spiro[azetidine-3,1'-isobenzofuran]-5'-yl)but-2-en-1-one according to the structure:

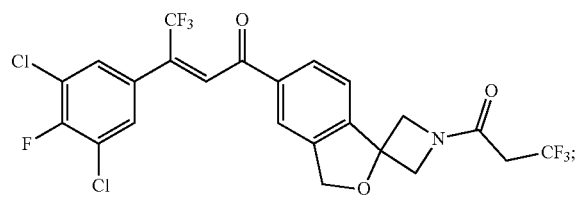 [SMILES: O=C(/C=C(/c1cc(Cl)c(F)c(Cl)c1)C(F)(F)F)c1ccc2c(c1)COC21CN(C(=O)CC(F)(F)F)C1]

(b) preparing a mixture comprising (Z)-3-(3,5-dichloro-4-fluorophenyl)-4,4,4-trifluoro -1-(1-(3,3,3-trifluoropropanoyl)-3'H-spiro[azetidine-3,1'-isobenzofuran]-5'-yl)but-2-en-1-one, an enantioselective catalyst, and a thiol donor and performing a reaction comprising reacting the mixture to form a thiol ether compound of formula (Ia):

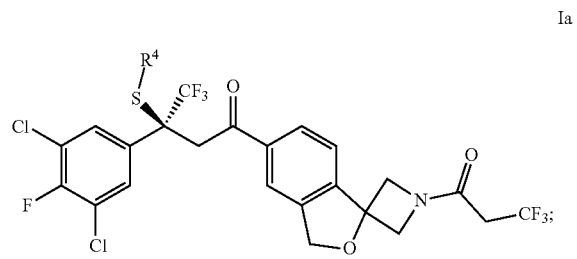

wherein $R^4$ is selected from hydrogen, optionally substituted $C_1$-$C_{10}$ alkyl, optionally substituted phenyl, and optionally substituted benzyl;

(c) cleaving the thiol ether of formula Ia to form a compound (S)-3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5'-yl)butan-1-one according to the structure:

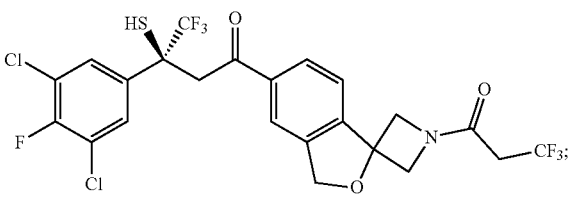 [SMILES: O=C(C[C@](S)(c1cc(Cl)c(F)c(Cl)c1)C(F)(F)F)c1ccc2c(c1)COC21CN(C(=O)CC(F)(F)F)C1]

and (d) preparing a mixture comprising (S)-3-(3,5-dichloro-4-fluorophenyl)-4,4,4-trifluoro-3-mercapto-1-(1-(3,3,3-trifluoropropanoyl)-3'H-spiro[azetidine-3,1'-isobenzofuran]-5'-yl)butan-1-one and hydroxylamine-O-sulfonic acid and performing a reaction comprising reacting the mixture to form a compound (S)-1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one according to the structure:

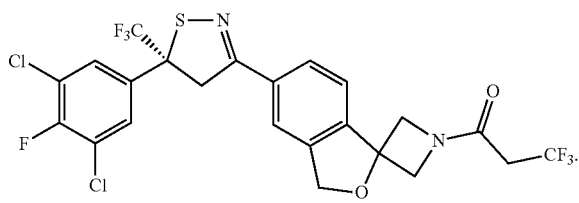 [SMILES: O=C(CC(F)(F)F)N1CC2(C1)OCc1cc(C3=NS[C@@](c4cc(Cl)c(F)c(Cl)c4)(C(F)(F)F)C3)ccc12]

21. The method of claim 20, wherein the reaction of (a) further comprises adding a base to the mixture.

22. The method of claim 21, wherein the base has a pKb of about −2 to about 9.

23. The method of claim 22, wherein the base is selected from potassium hydroxide, sodium hydroxide, calcium hydroxide, Hunig's Base, 1,8diazabicyclo[5.4.0]undec-7ene, N-methylmorpholine, pyridine, 2,6-di-tert-butylpyridine, 2,6-lutidine, N,N,N',N'-Tetramethylethylenediamine, (1,4-diazabicyclo[2.2.2]octane), 2,2,6,6-tetramethylpiperidine, trimethylamine, and cesium carbonate.

24. The method of claim 20 wherein the enantioselective catalyst is selected from a secondary amine, a thiourea, and a squaramide enantioselective catalyst.

25. The method of claim 24, wherein the squaramide enantioselective catalyst is 3-((3,5-bis(trifluoromethyl)phenyl)amino)-4-(((R)-(6-methoxyquinolin-4-yl)((1S,2R,4S,5R)-5-vinylquinuclidin-2-yl)methyl)amino)cyclobut-3-ene-1,2-dione according to the structure:

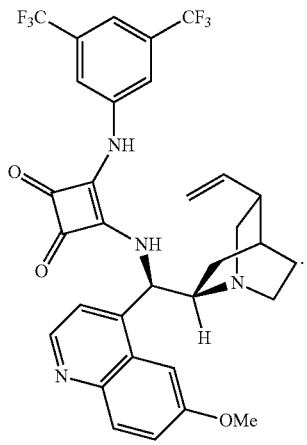 [SMILES: C=CC1CN2CCC1C[C@@H]2[C@H](Nc1c(Nc2cc(C(F)(F)F)cc(C(F)(F)F)c2)c(=O)c1=O)c1ccnc2ccc(OC)cc12]

26. The method of claim 20, wherein the thiol donor is selected from benzyl mercaptan and 4-methoxybenzyl mercaptan.

27. The method of claim 20, wherein the thiol ether compound of formula (Ia) is (S)-3-(3,5-dichloro-4-fluorophenyl)-4,4,4-trifluoro-3-((4-methoxybenzyl)thio)-1-(1-(3,3,3-trifluoropropanoyl)-3'H-spiro[azetidine-3,1'-isobenzofuran]-5'-yl)butan-1-one according to the structure:

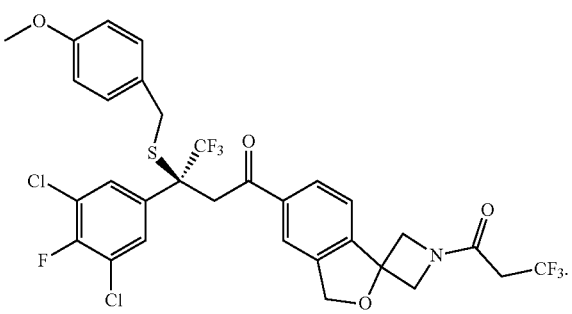 [SMILES: COc1ccc(CS[C@@](CC(=O)c2ccc3c(c2)COC32CN(C(=O)CC(F)(F)F)C2)(c2cc(Cl)c(F)c(Cl)c2)C(F)(F)F)cc1]

28. The method of claim 20, wherein the cleaving (c) is an acid based cleavage comprising preparing a mixture comprising the thiol ether of formula Ia and adding an acid.

29. The method of claim 28, wherein the acid has a pKa of less than 1.

30. The method of claim 29, wherein the acid is selected from hydrochloric acid, trifluoroacetic acid and triflic acid.

31. The method of claim 20, wherein the reaction of (d) further comprises adding a base and quenching the reaction with an acid.

32. A compound according to claim 8, wherein the compound is designated as the (S) enantiomer and is about 90%, 91%, 92%, 93%, 94%, 95%, 96%, 97%, 98%, 99%, 99.5%, 99.8%, 99.9%, or 100% free of (R) enantiomer.

33. A compound according to claim 9, wherein the compound is designated as the (S) enantiomer and is about 90%, 91%, 92%, 93%, 94%, 95%, 96%, 97%, 98%, 99%, 99.5%, 99.8%, 99.9%, or 100% free of (R) enantiomer.

* * * * *